(12) United States Patent
Ikeda et al.

(10) Patent No.: US 9,428,470 B2
(45) Date of Patent: Aug. 30, 2016

(54) HETEROCYCLIC COMPOUND

(71) Applicant: Takeda Pharmaceutical Company Limited, Chuo-ku, Osaka-shi, Osaka (JP)

(72) Inventors: Zenichi Ikeda, Kanagawa (JP); Minoru Sasaki, Kanagawa (JP); Keiko Kakegawa, Kanagawa (JP); Fumiaki Kikuchi, Kanagawa (JP); Yoichi Nishikawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/619,464

(22) Filed: Feb. 11, 2015

(65) Prior Publication Data

US 2015/0225354 A1 Aug. 13, 2015

(30) Foreign Application Priority Data

Feb. 13, 2014 (JP) ................................. 2014-025944

(51) Int. Cl.
*C07D 261/04* (2006.01)
*C07D 413/10* (2006.01)

(52) U.S. Cl.
CPC ........... *C07D 261/04* (2013.01); *C07D 413/10* (2013.01)

(58) Field of Classification Search
CPC .................................................. C07D 261/04
See application file for complete search history.

(56) References Cited

U.S. PATENT DOCUMENTS

| 5,116,985 | A | 5/1992 | Takeshita et al. |
| 6,388,122 | B1 | 5/2002 | Kido et al. |
| 2008/0009537 | A1 | 1/2008 | Sakai |
| 2010/0311690 | A1 | 12/2010 | Harosh et al. |
| 2012/0283222 | A1 | 11/2012 | Konishi et al. |
| 2013/0338132 | A1 | 12/2013 | Koshiba et al. |
| 2014/0094489 | A1 | 4/2014 | Suzuki et al. |

FOREIGN PATENT DOCUMENTS

| EP | 2511271 A1 | 10/2012 |
| EP | 2757093 A1 | 7/2014 |
| JP | 03-200764 A | 9/1991 |
| JP | 09-124571 A | 5/1997 |
| JP | 10-101556 A | 4/1998 |
| JP | 10-251239 A | 9/1998 |
| WO | WO 97/37969 A1 | 10/1997 |
| WO | WO 2006/050999 A2 | 5/2006 |
| WO | WO 2006/057152 A1 | 6/2006 |
| WO | WO 2006/057551 A1 | 6/2006 |
| WO | WO 2007/087130 A2 | 8/2007 |
| WO | WO 2009/071601 A1 | 6/2009 |
| WO | WO 2011/071048 A1 | 6/2011 |
| WO | WO 2012/169579 A1 | 12/2012 |
| WO | WO 2013/039187 A1 | 3/2013 |
| WO | WO 2013/102899 A1 | 7/2013 |
| WO | WO 2013/187533 A1 | 12/2013 |
| WO | WO 2014/106846 A2 | 7/2014 |
| WO | WO 2014/142219 A1 | 9/2014 |

OTHER PUBLICATIONS

International Search Report dated May 13, 2015, in PCT/JP2015/000640.
International Search Report dated May 13, 2015, in PCT/JP2015/000639.
Naleway et al., "Synthesis and Use of New Fluorogenic Precipitating Substrates," Tetrahedron Letters, Nov. 14, 1994, 35(46):8569-8572.
Zlatoidsky et al., "Synthesis and structure-activity relationship study of the new set of trypsin-like proteinase inhibitors," Eur. J. Med. Chem., Dec. 1, 1999, 34(12):1023-1034.
Notice of Allowance dated Feb. 10, 2016, in U.S. Appl. No. 14/619,489.

*Primary Examiner* — Samantha Shterengarts
(74) *Attorney, Agent, or Firm* — Foley & Lardner LLP

(57) ABSTRACT

A fused heterocyclic compound having an enteropeptidase inhibitory action and use of the compound as a medicament for treatment or prophylaxis of obesity, diabetes mellitus, etc., are provided.
Specifically, a compound represented by the following formula (I):

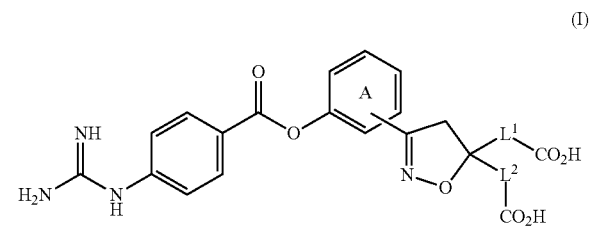

wherein each symbol is as defined herein,
or a salt thereof and use of the compound as a medicament for treatment or prophylaxis of obesity, diabetes mellitus, etc., are provided.

3 Claims, No Drawings

HETEROCYCLIC COMPOUND

RELATED APPLICATION

The present application claims a priority right based on Japanese Patent Application No. 2014-25944 (filed Feb. 13, 2014), the content of which is incorporated herein by reference.

TECHNICAL FIELD

The present invention relates to a heterocyclic compound that has an enteropeptidase inhibitory action and is useful in the treatment or prophylaxis of obesity, diabetes mellitus, etc., and a medicament comprising the same.

BACKGROUND OF THE INVENTION

Enteropeptidase is a serine protease that converts trypsinogen, which is secreted from the pancreas after a meal, into trypsin. Trypsin in a state activated by enteropeptidase then activates protease precursors such as chymotrypsinogen, procarboxypeptidase, and proelastase. These active forms of proteases degrade dietary proteins into amino acid units, and the resulting amino acids are absorbed from the small intestine. Thus, enteropeptidase inhibitors are capable of suppressing protein degradation and absorption and are useful as therapeutic drugs for obesity.

Examples of heterocyclic compounds include the following:

(1) A compound that has a trypsin inhibitory action and is useful in the treatment or prophylaxis of renal diseases and diseases involving trypsin, the compound being represented by the following formula:

[Chem. 1]

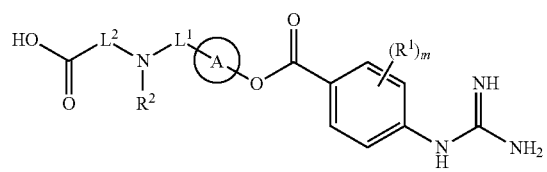

wherein
ring A represents

[Chem. 2]

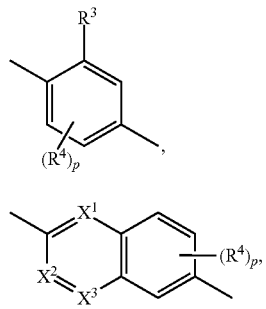

(a)

(b)

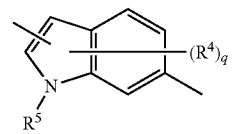

(c)

$R^1$ represents H, halogen, lower alkyl, or OH;
$R^2$ represents H, optionally substituted cycloalkyl, optionally substituted aryl, an optionally substituted aromatic heterocyclic ring, an optionally substituted non-aromatic heterocyclic ring, —C(O)-lower alkylene-optionally substituted aryl, or optionally substituted lower alkyl;
$L^1$ represents —$Y^1$-lower alkylene-$Y^2$— or —C(O)—N($R^6$)—;
$Y^1$ represents a bond or —C(O)—;
$Y^2$ represents a bond, —N($R^6$)—, or —C(O)—N($R^6$)—;
$L^2$ represents -(lower alkylene optionally substituted by $CO_2H$ or the like)-, —$Y^3$-cyclohexanediyl-$Y^4$—, or —$Y^3$-phenylene-$Y^4$—, or $L^2$ may form optionally substituted cyclic amino together with $R^2$;
$Y^3$ represents a bond or lower alkylene;
$Y^4$ represents a bond, lower alkylene, or —C(O)—;
$R^3$ represents H, lower alkyl optionally substituted by halogen, halogen, OH, —O-lower alkyl, cycloalkyl, aryl, or the like;
$R^4$ represents lower alkyl optionally substituted by halogen, halogen, OH, —O-lower alkyl, cycloalkyl, aryl, or the like;
$R^5$ and $R^6$ each represent H or lower alkyl;
$X^1$, $X^2$, and $X^3$ each represent CH or N, provided that at least one of $X^1$, $X^2$, and $X^3$ is N;
m represents an integer of 0 to 4;
p represents an integer of 0 to 3; and
q represents an integer of 0 to 4
(Patent Literature 1).

(2) A compound that has a serine protease inhibitory action and is useful in the treatment or prophylaxis of obesity, hyperlipidemia, diabetes mellitus, diabetic complications, and metabolic syndrome, the compound being represented by the following formula:

[Chem. 3]

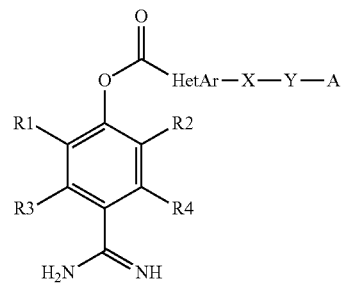

wherein
R1, R2, R3, and R4 each represent H or the like;
HetAr represents an optionally substituted heteroaromatic ring;
X represents optionally substituted lower alkylene or the like;
Y represents carbonyl or the like;

A represents

or the like; and

R6 and R7 each represent H, optionally substituted lower alkyl, or the like (Patent Literature 2).

(3) A compound that has a serine protease inhibitory action and is useful in the treatment or prophylaxis of obesity, hyperlipidemia, diabetes mellitus, diabetic complications, and metabolic syndrome, the compound being represented by the following formula:

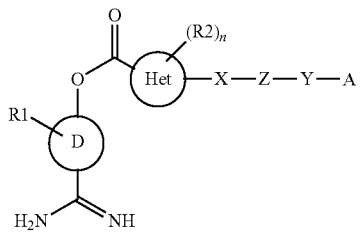

wherein

D represents a benzene ring, a naphthalene ring, or a pyridine ring;

Het represents a heterocyclic ring;

R1 represents H or the like;

R2 represents nitro, lower alkyl, or the like;

X represents optionally substituted lower alkylene;

Z represents —N(R3)- (wherein R3 represents H, optionally substituted lower alkyl, optionally substituted lower cycloalkyl, or the like);

Y represents a single bond or —(CH$_2$)p-C(R4a) (R4b)-(CH$_2$)q- (wherein R4a and R4b each represent H, lower alkyl, or aralkyl, and p and q each represent an integer of 0 to 5); and A represents —CO$_2$R6 (wherein R6 represents H or lower alkyl) or

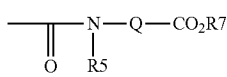

(wherein Q represents optionally substituted lower alkylene, and R7 represents H or lower alkyl)

(Patent Literature 3).

(4) A compound that has an enteropeptidase inhibitory action and is useful in the treatment or prophylaxis of obesity and diseases associated with abnormal fat metabolism, the compound being represented by the following formula:

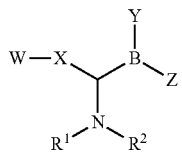

wherein

B represents boron;

W represents a nitrogen-containing functional group

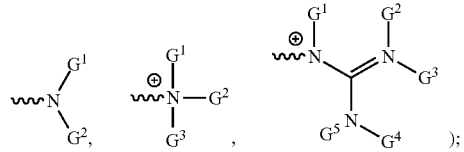

X represents a linker (CX$^1$X$^2$)p;

Y and Z each represent OH, OR (wherein R represents alkyl), a homocyclic ring, a heterocyclic ring, or the like;

R$^1$ represents aminoacyl, acyl, or the like; and

R$^2$ represents H, alkyl, or OR (wherein R represents H or alkyl)

(Patent Literature 4).

(5) A compound that has a serine protease inhibitory action and is useful in the treatment or prophylaxis of obesity, diabetes mellitus, etc., the compound being represented by the following formula:

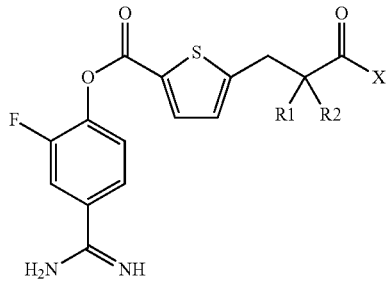

wherein

R$^1$ and R$^2$ each represent alkyl or the like; and

X represents —OR$^3$, —NR$^4$R$^5$, or the like (Patent Literature 5).

CITATION LIST

Patent Literature

[PTL 1]
WO2013/039187
[PTL 2]
WO2011/071048
[PTL 3]
WO2012/169579
[PTL 4]
WO2009/071601
[PTL 5]
WO2013/187533

SUMMARY OF INVENTION

Technical Problem

An object of the present invention is to provide a heterocyclic compound that has a superior enteropeptidase inhibitory action and is useful in the treatment or prophylaxis of obesity, diabetes mellitus, etc., and a medicament comprising the same.

Solution to Problem

The present inventors have conducted diligent studies to attain the object and consequently completed the present invention by finding that a compound represented by the formula (I) shown below has a superior enteropeptidase inhibitory action.

Accordingly, the present invention is as follows:

[1] A compound represented by the formula (I):

[Chem. 10]

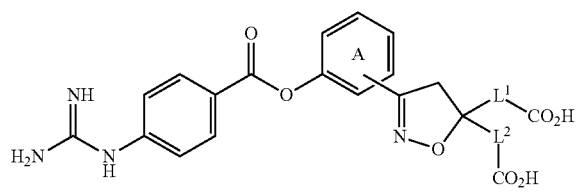

(I)

wherein ring A represents an optionally further substituted benzene ring; and $L^1$ and $L^2$ each independently represent a bond or an optionally substituted linear $C_{1-3}$ alkylene group, or a salt thereof (hereinafter sometimes to be referred to as compound (I)).

[2] The compound according to the above-mentioned [1] or a salt thereof, wherein ring A represents a benzene ring optionally further substituted by 1 to 3 substituents selected from (1) a $C_{1-6}$ alkyl group optionally substituted by 1 to 3 substituents selected from (i) a carboxy group, (ii) a mono- or di-$C_{1-6}$ alkyl-carbamoyl group optionally substituted by 1 to 3 substituents selected from: a carboxy group; a $C_{1-6}$ alkylsulfonyl group; a carbamoyl group; and a sulfo group, and (iii) a 3- to 14-membered non-aromatic heterocyclylcarbonyl group optionally substituted by a carboxy group(s), (2) a 3- to 14-membered non-aromatic heterocyclic group optionally substituted by 1 to 3 substituents selected from (i) a $C_{1-6}$ alkyl-carbonyl group optionally substituted by 1 to 3 substituents selected from: a carboxy group; and a mono or di-$C_{1-6}$ alkyl-carbamoyl group optionally substituted by 1 to 3 carboxy groups, and (ii) a $C_{1-6}$ alkyl group optionally substituted by 1 to 3 carboxy groups, (3) a $C_{3-10}$ cycloalkyl group optionally substituted by 1 to 3 $C_{1-6}$ alkyl groups, and (4) a $C_{6-14}$ aryl group.

[3] The compound according to the above-mentioned [1] or [2] or a salt thereof, wherein $L^1$ and $L^2$ each independently represent a bond or a linear $C_{1-3}$ alkylene group.

[4] The compound according to the above-mentioned [1] or a salt thereof, wherein ring A represents a benzene ring optionally further substituted by 1 to 3 substituents selected from (1) a $C_{1-6}$ alkyl group optionally substituted by 1 to 3 substituents selected from (i) a carboxy group, (ii) a mono- or di-$C_{1-6}$ alkyl-carbamoyl group optionally substituted by 1 to 3 substituents selected from: a carboxy group; a $C_{1-6}$ alkylsulfonyl group; a carbamoyl group; and a sulfo group, and (iii) a 3- to 14-membered non-aromatic heterocyclylcarbonyl group optionally substituted by a carboxy group(s), (2) a 3- to 14-membered non-aromatic heterocyclic group optionally substituted by 1 to 3 substituents selected from (i) a $C_{1-6}$ alkyl-carbonyl group optionally substituted by 1 to 3 substituents selected from a carboxy group; and a mono or di-$C_{1-6}$ alkyl-carbamoyl group optionally substituted by 1 to 3 carboxy groups, (ii) a $C_{1-6}$ alkyl group optionally substituted by 1 to 3 carboxy groups, (3) a $C_{3-10}$ cycloalkyl group optionally substituted by 1 to 3 $C_{1-6}$ alkyl groups, and (4) a $C_{6-14}$ aryl group, and $L^1$ and $L^2$ each independently represent a bond or a linear $C_{1-3}$ alkylene group.

[5] (5R)-3-(3-((4-Carbamimidamidobenzoyl)oxy)phenyl)-5-(carboxymethyl)-4,5-dihydro-1,2-oxazole-5-carboxylic acid or a salt thereof.

[6] (5S)-3-(3-((4-Carbamimidamidobenzoyl)oxy)phenyl)-5-(carboxymethyl)-4,5-dihydro-1,2-oxazole-5-carboxylic acid or a salt thereof.

[7] 2,2'-(3-(3-((4-Carbamimidamidobenzoyl)oxy)phenyl)-4,5-dihydro-1,2-oxazole-5,5-diyl)diacetic acid or a salt thereof.

[8] A medicament comprising the compound of the above-mentioned [1] or a salt thereof.

[9] The medicament of the above-mentioned [8], which is an enteropeptidase inhibitor.

[10] The medicament of the above-mentioned [8], which is an agent for the prophylaxis or treatment of obesity.

[11] The medicament of the above-mentioned [8], which is an agent for the prophylaxis or treatment of diabetes mellitus.

[12] A method for preventing or treating obesity in a mammal, comprising administering to the mammal an effective amount of the compound according to the above-mentioned [1] or a salt thereof.

[13] A method for preventing or treating diabetes mellitus in a mammal, comprising administering to the mammal an effective amount of the compound according to the above-mentioned [1] or a salt thereof.

[14] A method for inhibiting an enteropeptidase in a mammal, comprising administering to the mammal an effective amount of the compound according to the above-mentioned [1] or a salt thereof.

[15] Use of the compound according to the above-mentioned [1] or a salt thereof in the production of an agent for the prophylaxis or treatment of obesity.

[16] Use of the compound according to the above-mentioned [1] or a salt thereof in the production of an agent for the prophylaxis or treatment of diabetes mellitus.

[17] The compound according to the above-mentioned [1] or a salt thereof for use in the prophylaxis or treatment of obesity.

[18] The compound according to the above-mentioned [1] or a salt thereof for use in the prophylaxis or treatment of diabetes mellitus.

Advantageous Effects of Invention

Compound (I) has a superior enteropeptidase inhibitory action and is useful in the treatment or prophylaxis of obesity, diabetes mellitus, etc.

DETAILED DESCRIPTION OF THE INVENTION

The present invention is described in detail in the following.

The definition of each substituent used in the present specification is described in detail in the following. Unless otherwise specified, each substituent has the following definition.

In the present specification, examples of the "halogen atom" include fluorine, chlorine, bromine and iodine. In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl. In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl. In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "C$_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated C$_{1-6}$ alkylsulfonyl group" include a C$_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl. In the present specification, examples of the "C$_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a C$_{1-6}$ alkyl group, a C$_{2-6}$ alkenyl group, a C$_{2-6}$ alkynyl group, a C$_{3-10}$ cycloalkyl group, a C$_{3-10}$ cycloalkenyl group, a C$_{6-14}$ aryl group and a C$_{7-16}$ aralkyl group.

In the present specification, examples of the "optionally substituted hydrocarbon group" include a hydrocarbon group optionally having substituent(s) selected from the following substituent group A.

{Substituent Group A}
(1) a halogen atom,
(2) a nitro group,
(3) a cyano group,
(4) an oxo group,
(5) a hydroxy group,
(6) an optionally halogenated C$_{1-6}$ alkoxy group,
(7) a C$_{6-14}$ aryloxy group (e.g., phenoxy, naphthoxy),
(8) a C$_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a C$_{1-6}$ alkyl-carbonyloxy group (e.g., acetoxy, propanoyloxy),
(12) a C$_{6-14}$ aryl-carbonyloxy group (e.g., benzoyloxy, 1-naphthoyloxy, 2-naphthoyloxy),
(13) a C$_{1-6}$ alkoxy-carbonyloxy group (e.g., methoxycarbonyloxy, ethoxycarbonyloxy, propoxycarbonyloxy, butoxycarbonyloxy),
(14) a mono- or di-C$_{1-6}$ alkyl-carbamoyloxy group (e.g., methylcarbamoyloxy, ethylcarbamoyloxy, dimethylcarbamoyloxy, diethylcarbamoyloxy),
(15) a C$_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated C$_{1-6}$ alkylsulfonyloxy group (e.g., methylsulfonyloxy, trifluoromethylsulfonyloxy),
(19) a C$_{6-14}$ arylsulfonyloxy group optionally substituted by a C$_{1-6}$ alkyl group (e.g., phenylsulfonyloxy, toluenesulfonyloxy),
(20) an optionally halogenated C$_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated C$_{1-6}$ alkyl-carbonyl group,
(26) a C$_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a C$_{1-6}$ alkoxy-carbonyl group,
(30) a C$_{6-14}$ aryloxy-carbonyl group (e.g., phenyloxycarbonyl, 1-naphthyloxycarbonyl, 2-naphthyloxycarbonyl),
(31) a C$_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-C$_{1-6}$ alkyl-carbamoyl group,
(35) a C$_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated C$_{1-6}$ alkylsulfonyl group,
(39) a C$_{6-14}$ arylsulfonyl group,
(40) a 5- to 14-membered aromatic heterocyclylsulfonyl group (e.g., pyridylsulfonyl, thienylsulfonyl),
(41) an optionally halogenated C$_{1-6}$ alkylsulfinyl group,
(42) a C$_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-C$_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-C$_{6-14}$ arylamino group (e.g., phenylamino),
(47) a 5- to 14-membered aromatic heterocyclylamino group (e.g., pyridylamino),
(48) a C$_{7-16}$ aralkylamino group (e.g., benzylamino),
(49) a formylamino group,
(50) a C$_{1-6}$ alkyl-carbonylamino group (e.g., acetylamino, propanoylamino, butanoylamino),
(51) a (C$_{1-6}$ alkyl)(C$_{1-6}$ alkyl-carbonyl)amino group (e.g., N-acetyl-N-methylamino),
(52) a C$_{6-14}$ aryl-carbonylamino group (e.g., phenylcarbonylamino, naphthylcarbonylamino),
(53) a C$_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a C$_{7-16}$ aralkyloxy-carbonylamino group (e.g., benzyloxycarbonylamino),
(55) a C$_{1-6}$ alkylsulfonylamino group (e.g., methylsulfonylamino, ethylsulfonylamino),
(56) a C$_{6-14}$ arylsulfonylamino group optionally substituted by a C$_{1-6}$ alkyl group (e.g., phenylsulfonylamino, toluenesulfonylamino),

(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, beta-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-beta-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "one or two substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a monoor di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "one or two substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di- (optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di- (optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "one or two substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "one or two substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "one or two substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxy-carbonyloxy), a 5- to 14-membered aromatic heterocycly-loxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group. Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

Hereinafter, each symbol of the formula (I) is described in the following.

Ring A represents an optionally further substituted benzene ring.

Examples of the "optionally further substituted benzene ring" represented by ring A include a benzene ring optionally further having substituent(s) selected from the substituent group A. The number of the additional substituents in the "optionally further substituted benzene ring" is, for example, 1 to 3. When the number of the substituents is two or more, the respective substituents may be the same or different.

Preferably, ring A is a benzene ring optionally further substituted by 1 to 3 (preferably 1) substituents selected from (1) an optionally substituted $C_{1-6}$ alkyl group, (2) an optionally substituted 3- to 14-membered non-aromatic heterocyclic group, (3) an optionally substituted $C_{3-10}$ cycloalkyl group, and (4) an optionally substituted $C_{6-14}$ aryl group.

More preferably, ring A is a benzene ring optionally further substituted by 1 to 3 (preferably 1) substituents selected from (1) a $C_{1-6}$ alkyl group (e.g., methyl, ethyl) optionally substituted by 1 to 3 (preferably 1) substituents selected from (i) a carboxy group, and (ii) a mono- or di-$C_{1-6}$ alkyl-carbamoyl group (e.g., methylcarbamoyl, dimethylcarbamoyl, ethylcarbamoyl, propylcarbamoyl) optionally substituted by 1 to 3 substituents selected from: a carboxy group; a $C_{1-6}$ alkylsulfonyl group; a carbamoyl group; and a sulfo group, and (iii) a 3- to 14-membered non-aromatic heterocyclylcarbonyl group (e.g., morpholinylcarbonyl, piperidinylcarbonyl, 1,1-dioxidothiomorpholinylcarbonyl) optionally substituted by a carboxy group(s), (2) a 3- to 14-membered non-aromatic heterocyclic group (e.g., piperidyl) optionally substituted by 1 to 3 (preferably 1) substituents selected from (i) a $C_{1-6}$ alkyl-carbonyl group (e.g., propionyl) optionally substituted by 1 to 3 substituents selected from: a carboxy group; and a mono or di-$C_{1-6}$ alkyl-carbamoyl group optionally substituted by 1 to 3 carboxy groups, and, (ii) a $C_{1-6}$ alkyl groups (e.g., ethyl) optionally substituted by 1 to 3 carboxy groups, (3) a $C_{3-10}$ cycloalkyl group (e.g., cyclohexyl) optionally substituted by 1 to 3 (preferably 1) $C_{1-6}$ alkyl groups (e.g., tert-butyl), and (4) a $C_{6-14}$ aryl group (e.g., phenyl).

Among them, ring A is preferably a benzene ring optionally further substituted by 1 to 3 (preferably 1) substituents selected from (1) a $C_{1-6}$ alkyl group (e.g., methyl, ethyl) optionally substituted by 1 to 3 (preferably 1) substituents selected from
  (i) a carboxy group, and
  (ii) a mono- or di-$C_{1-6}$ alkyl-carbamoyl group (e.g., ethylcarbamoyl) optionally substituted by 1 to 3 carboxy groups,
(2) a 3- to 14-membered non-aromatic heterocyclic group (e.g., piperidyl) optionally substituted by 1 to 3 (preferably 1) substituents selected from a $C_{1-6}$ alkyl-carbonyl group (e.g., propionyl) optionally substituted by 1 to 3 carboxy groups,
(3) a $C_{3-10}$ cycloalkyl group (e.g., cyclohexyl) optionally substituted by 1 to 3 $C_{1-6}$ alkyl groups (e.g., tert-butyl), and
(4) a $C_{6-14}$ aryl group (e.g., phenyl).

Further preferably, ring A is a benzene ring.

Examples of the above-mentioned "optionally substituted $C_{1-6}$ alkyl group" include $C_{1-6}$ alkyl groups optionally having substituent(s) selected from the substituent group A. The number of the substituents in the "optionally substituted $C_{1-6}$ alkyl group" is, for example, 1 to 5, preferably 1 to 3. When the number of the substituents is two or more, the respective substituents may be the same or different.

Examples of the above-mentioned "optionally substituted 3- to 14-membered non-aromatic heterocyclic group" include 3- to 14-membered non-aromatic heterocyclic groups optionally having substituent(s) selected from the substituent group A and an oxo group. The number of the substituents in the "optionally substituted 3- to 14-membered non-aromatic heterocyclic group" is, for example, 1 to 5, preferably 1 to 3. When the number of the substituents is two or more, the respective substituents may be the same or different.

Examples of the above-mentioned "optionally substituted $C_{3-10}$ cycloalkyl group" include $C_{3-10}$ cycloalkyl groups optionally having substituent(s) selected from the substituent group A and an oxo group. The number of the substituents in the "optionally substituted $C_{3-10}$ cycloalkyl group" is, for example, 1 to 5, preferably 1 to 3. When the number of the substituents is two or more, the respective substituents may be the same or different.

Examples of the above-mentioned "optionally substituted $C_{6-14}$ aryl group" include $C_{6-14}$ aryl groups optionally having substituent(s) selected from the substituent group A. The number of the substituents in the "optionally substituted $C_{6-14}$ aryl group" is, for example, 1 to 5, preferably 1 to 3. When the number of the substituents is two or more, the respective substituents may be the same or different.

$L^1$ and $L^2$ each independently represent a bond or an optionally substituted linear $C_{1-3}$ alkylene group.

The "linear $C_{1-3}$ alkylene group" represented by $L^1$ or $L^2$ means —$CH_2$—, —$(CH_2)_2$—, or —$(CH_2)_3$—.

Examples of the "optionally substituted linear $C_{1-3}$ alkylene group" represented by $L^1$ or $L^2$ include linear $C_{1-3}$ alkylene groups optionally having substituent(s) selected from the substituent group A. The number of the substituents in the "optionally substituted linear $C_{1-3}$ alkylene group" is, for example, 1 to 3. When the number of the substituents is two or more, the respective substituents may be the same or different.

Preferably, each of $L^1$ and $L^2$ is independently a bond or a linear $C_{1-3}$ alkylene group (e.g., —$CH_2$—, —$(CH_2)_2$—). More preferably, $L^1$ is a linear $C_{1-3}$ alkylene group (e.g., —$CH_2$—, —$(CH_2)_2$—), and $L^2$ is a bond or a linear $C_{1-3}$ alkylene group (e.g., —$CH_2$—, —$(CH_2)_2$—).

Further preferably, $L^1$ is a linear $C_{1-3}$ alkylene group (e.g., —$CH_2$—), and $L^2$ is a bond.

In the formula (I), the partial structure represented by the formula (II):

[Chem. 11]

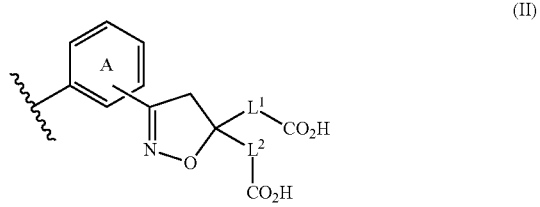

(II)

is preferably a structure represented by the formula (III) or (IV):

[Chem. 12]

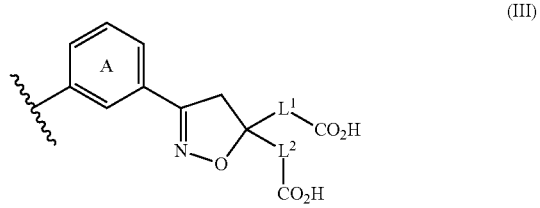

(III)

[Chem. 13]

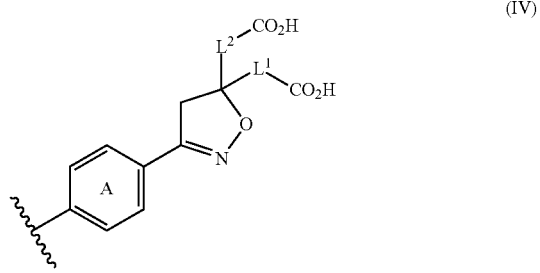

(IV)

More preferably, in the formula (I), the partial structure represented by the formula (II):

[Chem. 14]

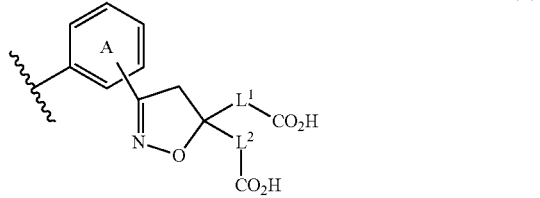

(II)

is a structure represented by the formula (III):

[Chem. 15]

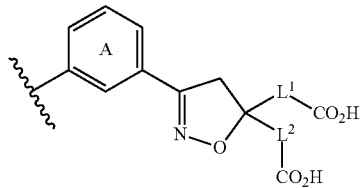

(III)

Specific examples of preferable compound (I) include the following.

[Compound X]
Compound (I) wherein
ring A is a benzene ring optionally further substituted by 1 to 3 (preferably 1) substituents selected from
(1) a $C_{1-6}$ alkyl group (e.g., methyl, ethyl) optionally substituted by 1 to 3 (preferably 1) substituents selected from
  (i) a carboxy group, and
  (ii) a mono- or di-$C_{1-6}$ alkyl-carbamoyl group (e.g., methylcarbamoyl, dimethylcarbamoyl, ethylcarbamoyl, propylcarbamoyl) optionally substituted by 1 to 3 substituents selected from: a carboxy group; a $C_{1-6}$ alkylsulfonyl group; a carbamoyl group; and a sulfo group, and
  (iii) a 3- to 14-membered non-aromatic heterocyclylcarbonyl group (e.g., morpholinylcarbonyl, piperidinylcarbonyl, 1,1-dioxidothiomorpholinylcarbonyl) optionally substituted by a carboxy group(s),
(2) a 3- to 14-membered non-aromatic heterocyclic group (e.g., piperidyl) optionally substituted by 1 to 3 (preferably 1) substituents selected from
  (i) a $C_{1-6}$ alkyl-carbonyl group (e.g., propionyl) optionally substituted by 1 to 3 substituents selected from: a carboxy group; and a mono or di-$C_{1-6}$ alkyl-carbamoyl group optionally substituted by 1 to 3 carboxy groups, and,
  (ii) a $C_{1-6}$ alkyl group (e.g., ethyl) optionally substituted by 1 to 3 carboxy groups,
(3) a $C_{3-10}$ cycloalkyl group (e.g., cyclohexyl) optionally substituted by 1 to 3 (preferably 1) $C_{1-6}$ alkyl groups (e.g., tert-butyl), and
(4) a $C_{6-14}$ aryl group (e.g., phenyl); and each of $L^1$ and $L^2$ is independently a bond or a linear $C_{1-3}$ alkylene group (e.g., —$CH_2$—, —($CH_2$)$_2$—).

[Compound A]
Compound (I) wherein
ring A is a benzene ring optionally further substituted by 1 to 3 (preferably 1) substituents selected from
(1) a $C_{1-6}$ alkyl group (e.g., methyl, ethyl) optionally substituted by 1 to 3 (preferably 1) substituents selected from
  (i) a carboxy group, and
  (ii) a mono- or di-$C_{1-6}$ alkyl-carbamoyl group (e.g., ethylcarbamoyl) optionally substituted by 1 to 3 carboxy groups,
(2) a 3- to 14-membered non-aromatic heterocyclic group (e.g., piperidyl) optionally substituted by 1 to 3 (preferably 1) substituents selected from
  a $C_{1-6}$ alkyl-carbonyl group (e.g., propionyl) optionally substituted by 1 to 3 carboxy groups,
(3) a $C_{3-10}$ cycloalkyl group (e.g., cyclohexyl) optionally substituted by 1 to 3 $C_{1-6}$ alkyl groups (e.g., tert-butyl), and (4) a $C_{6-14}$ aryl group (e.g., phenyl); and each of $L^1$ and $L^2$ is independently a bond or a linear $C_{1-3}$ alkylene group (e.g., —$CH_2$—, —($CH_2$)$_2$—).

[Compound B]
Compound (I) wherein
ring A is a benzene ring; and
$L^1$ is a linear $C_{1-3}$ alkylene group (e.g., —$CH_2$—), and $L^2$ is a bond.

Examples of the salt of the compound represented by the formula (I) include metal salts, ammonium salts, salts with organic bases, salts with inorganic acids, salts with organic acids, salts with basic or acidic amino acids, and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

Among the above-mentioned salts, a pharmaceutically acceptable salt is preferable.

Compound (I) may be a prodrug.

A prodrug of compound (I) is a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include: a compound wherein an amino of compound (I) is acylated, alkylated or phosphorylated (e.g., compound wherein an amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy of compound (I) is acylated, alkylated, phosphorylated or borated (e.g., a compound wherein a hydroxy of compound (I) is acetylated, palmitoylated, propanoylated, pivaloylated, succinylated, fumarylated, alanylated or dimethylaminomethylcarbonylated); a compound wherein a carboxy of compound (I) is esterified or amidated (e.g., a compound wherein a carboxy of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated); and the like. Among them, compounds in which carboxy of compound (I) is esterified with $C_{1-6}$ alkyl such as methyl, ethyl, tert-butyl and the like are preferably used. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, the prodrug may form a salt. Examples of such a salt include those exemplified as the above-mentioned salt of the compound represented by the formula (I).

Methods for producing the compound of the present invention are described in the following.

In production methods given below, starting materials or reagents used in each step and obtained compounds may each form a salt. Examples of such salt include the same as the above-mentioned salt of the compound of the present invention and the like.

When the compound obtained in each step is a free compound, it can be converted to a salt of interest by a method known per se. On the contrary, when the compound obtained in each step is a salt, it can be converted to a free form or a different type of salt of interest by a method known per se.

The compound obtained in each step may be used in subsequent reaction directly in the form of a reaction solution thereof or after being obtained as a crude product. Alternatively, the compound obtained in each step can be isolated and/or purified from the reaction mixture by separation means such as concentration, crystallization, recrystallization, distillation, solvent extraction, fractionation, chromatography, and the like according to a conventional method.

When compounds of starting materials or reagents for each step are commercially available, these commercially available products can be used directly.

For reaction in each step, the reaction time may differ depending on the reagent or solvent used and is usually 1 minute to 48 hours, preferably 10 minutes to 8 hours, unless otherwise specified.

For reaction in each step, the reaction temperature may differ depending on the reagent or solvent used and is usually −78 C ("C" represents "degrees Celsius") to 300 C, preferably −78 C to 150 C, unless otherwise specified.

For reaction in each step, the pressure may differ depending on the reagent or solvent used and is usually 1 atm to 20 atm, preferably 1 atm to 3 atm, unless otherwise specified.

For reaction in each step, for example, a microwave synthesis apparatus such as Initiator manufactured by Biotage Japan Ltd. and the like may be used. The reaction temperature may differ depending on the reagent or solvent used and is usually room temperature to 300 C, preferably 50 C to 250 C, unless otherwise specified. The reaction time may differ depending on the reagent or solvent used and is usually 1 minute to 48 hours, preferably 1 minute to 8 hours, unless otherwise specified.

For reaction in each step, a reagent is used at 0.5 equivalents to 20 equivalents, preferably 0.8 equivalents to 5 equivalents, relative to a substrate, unless otherwise specified. When a reagent is used as a catalyst, the reagent is used at 0.001 equivalents to 1 equivalent, preferably 0.01 equivalents to 0.2 equivalents, relative to a substrate. When a reagent also serves as a reaction solvent, the reagent is used in the amount of the solvent.

For reaction in each step, the reaction is performed without a solvent or after dissolution or suspension in an appropriate solvent, unless otherwise specified. Specific examples of the solvent include the solvents described in Examples and the following: Alcohols: methanol, ethanol, tert-butyl alcohol, 2-methoxyethanol, etc.;

Ethers: diethyl ether, diphenyl ether, tetrahydrofuran, 1,2-dimethoxyethane, etc.;

Aromatic hydrocarbons: chlorobenzene, toluene, xylene, etc.;

Saturated hydrocarbons: cyclohexane, hexane, etc.;

Amides: N,N-dimethylformamide, N-methylpyrrolidone, etc.;

Halogenated hydrocarbons: dichloromethane, carbon tetrachloride, etc.;

Nitriles: acetonitrile, etc.;

Sulfoxides: dimethyl sulfoxide, etc.;

Aromatic organic bases: pyridine, etc.;

Acid anhydrides: acetic anhydride, etc.;

Organic acids: formic acid, acetic acid, trifluoroacetic acid, etc.;

Inorganic acids: hydrochloric acid, sulfuric acid, etc.;

Esters: ethyl acetate, etc.;

Ketones: acetone, methyl ethyl ketone, etc.; and

Water.

These solvents may be used as a mixture of two or more thereof at an appropriate ratio.

When a base is used for reaction in each step, any of the following bases or the bases described in Examples, for example, is used.

Inorganic bases: sodium hydroxide, magnesium hydroxide, etc.;

Basic salts: sodium carbonate, calcium carbonate, sodium bicarbonate, etc.;

Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.;

Metal alkoxides: sodium ethoxide, potassium tert-butoxide, etc.;

Alkali metal hydrides: sodium hydride, etc.;

Metal amides: sodium amide, lithium diisopropylamide, lithium hexamethyldisilazide, etc.; and Organic lithiums: n-butyllithium, etc.

When an acid or acidic catalyst is used for reaction in each step, any of the following acids or acidic catalysts or the acids or acidic catalysts described in Examples, for example, is used.

Inorganic acids: hydrochloric acid, sulfuric acid, nitric acid, hydrobromic acid, phosphoric acid, etc.;

Organic acids: acetic acid, trifluoroacetic acid, citric acid, p-toluenesulfonic acid, 10-camphorsulfonic acid, etc.; and Lewis acids: boron trifluoride-diethyl ether complex, zinc iodide, anhydrous aluminum chloride, anhydrous zinc chloride, anhydrous iron chloride, etc.

Reaction in each step is performed in accordance with a method known per se, for example, the method described in Jikken Kagaku Koza (Encyclopedia of Experimental Chemistry in English), 5th Ed., Vol. 13-19 (edited by The Chemical Society of Japan); Shin Jikken Kagaku Koza (New Encyclopedia of Experimental Chemistry in English), Vol. 14-15 (edited by The Chemical Society of Japan); Reactions and Syntheses in the Organic Chemistry Laboratory, Revised, 2nd Ed. (L. F. Tietze, Th. Eicher, Nankodo Co., Ltd.); Revised Organic Name Reactions; The Reaction Mechanism and Essence (Hideo Togo, Kodansha Ltd.); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY Press); Comprehensive Heterocyclic Chemistry III, Vol. 1-14 (Elsevier B.V.); Strategic Applications of Named Reactions in Organic Synthesis (translated by Kiyoshi Tomioka, published by Kagaku-Dojin Publishing Company, INC); Comprehensive Organic Transformations (VCH Publishers Inc.) (1989), etc., or the method described in Examples, unless otherwise specified.

The protection or deprotection reaction of a functional group in each step is performed in accordance with a method known per se, for example, the method described in "Protective Groups in Organic Synthesis, 4th Ed." (Theodora W. Greene, Peter G. M. Wuts), Wiley-Interscience (2007); "Protecting Groups 3rd Ed." (P. J. Kocienski), Thieme Medical Publishers (2004), etc., or the method described in Examples. Examples of protecting groups for the hydroxyl group or phenolic hydroxyl group of an alcohol or the like include ether type protecting groups such as methoxymethyl ether, benzyl ether, t-butyldimethylsilyl ether, tetrahydropyranyl ether, and the like; carboxylic acid ester type protecting groups such as acetic acid ester and the like; sulfonic acid ester type protecting groups such as methanesulfonic acid ester and the like; carbonic acid ester type protecting groups such as t-butyl carbonate and the like; etc. Examples of protecting groups for the carbonyl group of an aldehyde include acetal type protecting groups such as dimethyl acetal and the like; cyclic acetal type protecting groups such as cyclic 1,3-dioxane and the like; etc.

Examples of protecting groups for the carbonyl group of a ketone include ketal type protecting groups such as dimethyl ketal and the like; cyclic ketal type protecting groups such as cyclic 1,3-dioxane and the like; oxime type protecting groups such as O-methyloxime and the like; hydrazone type protecting groups such as N,N-dimethylhydrazone and the like; etc.

Examples of protecting groups for the carboxyl group include ester type protecting groups such as methyl ester and the like; amide type protecting groups such as N,N-dimethylamide and the like; etc.

Examples of protecting groups for thiol include ether type protecting groups such as benzylthio ether and the like; ester type protecting groups such as thioacetic acid ester, thiocarbonate, thiocarbamate, and the like; etc.

Examples of protecting groups for the amino group or an aromatic heterocyclic ring such as imidazole, pyrrole, indole, or the like include carbamate type protecting groups such as benzyl carbamate and the like; amide type protecting groups such as acetamide and the like; alkylamine type protecting groups such as N-triphenylmethylamine and the like; sulfonamide type protecting groups such as methanesulfonamide and the like; etc.

A protecting group can be removed by a method known per se, for example, a method using acid, base, ultraviolet light, hydrazine, phenylhydrazine, sodium N-methyldithiocarbamate, tetrabutylammonium fluoride, palladium acetate, or trialkylsilyl halide (e.g., trimethylsilyl iodide, trimethylsilyl bromide), a reduction method, or the like.

In the case of performing reduction reaction in each step, examples of the reducing agent used include metal hydrides such as lithium aluminum hydride, sodium triacetoxy borohydride, sodium cyanoborohydride, diisobutyl aluminum hydride (DIBAL-H), sodium borohydride, tetramethylammonium triacetoxy borohydride, and the like; boranes such as borane-tetrahydrofuran complex and the like; Raney nickel; Raney cobalt; hydrogen; formic acid; etc. A catalyst such as palladium-carbon, a Lindlar's catalyst, or the like may be used in a method for reducing a carbon-carbon double bond or triple bond.

In the case of performing oxidation reaction in each step, examples of the oxidizing agent used include peracids such as m-chloroperbenzoic acid (MCPBA), hydrogen peroxide, t-butyl hydroperoxide, and the like; perchlorates such as tetrabutylammonium perchlorate and the like; chlorates such as sodium chlorate and the like; chlorites such as sodium chlorite and the like; periodates such as sodium periodate and the like; high-valent iodine reagents such as iodosylbenzene and the like; manganese-containing reagents such as manganese dioxide, potassium permanganate, and the like; leads such as lead tetraacetate and the like; chromium-containing reagents such as pyridinium chlorochromate (PCC), pyridinium dichromate (PDC), Jones reagents, and the like; halogen compounds such as N-bromosuccinimide (NBS) and the like; oxygen; ozone; sulfur trioxide-pyridine complex; osmium tetraoxide; selenium dioxide; 2,3-dichloro-5,6-dicyano-1,4-benzoquinone (DDQ); etc.

In the case of performing radical cyclization reaction in each step, examples of the radical initiator used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide; etc. Examples of the radical reagent used include tributylstannane, tristrimethylsilylsilane, 1,1,2,2-tetraphenyldisilane, diphenylsilane, samarium iodide, and the like.

In the case of performing Wittig reaction in each step, examples of the Wittig reagent used include alkylidene phosphoranes. The alkylidene phosphoranes can be prepared by a method known per se, for example, the reaction of a phosphonium salt with a strong base.

In the case of performing Horner-Emmons reaction in each step, examples of the reagent used include phosphonoacetic acid esters such as methyl dimethylphosphonoacetate, ethyl diethylphosphonoacetate, and the like; and bases such as alkali metal hydrides, organic lithiums, and the like.

In the case of performing Friedel-Crafts reaction in each step, examples of the reagent used include a Lewis acid and an acid chloride or an alkylating agent (e.g., alkyl halides, alcohols, olefins, etc.). Alternatively, an organic or inorganic acid may be used instead of the Lewis acid, and an acid anhydride such as acetic anhydride or the like may be used instead of the acid chloride.

In the case of aromatic nucleophilic substitution reaction in each step, a nucleophile (e.g., amines, imidazole, etc.) and a base (e.g., basic salts, organic bases, etc.) are used as reagents.

In the case of performing carbanion-mediated nucleophilic addition reaction, carbanion-mediated nucleophilic 1,4-addition reaction (Michael addition reaction), or carbanion-mediated nucleophilic substitution reaction in each step, examples of the base used for generating a carbanion include organic lithiums, metal alkoxides, inorganic bases, organic bases, and the like.

In the case of performing Grignard reaction in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, the reaction of alkyl halide or aryl halide with metal magnesium in the presence of ether or tetrahydrofuran as a solvent.

In the case of performing Knoevenagel condensation reaction in each step, an active methylene compound flanked by two electron withdrawing groups (e.g., malonic acid, diethyl malonate, malononitrile, etc.) and a base (e.g., organic bases, metal alkoxides, inorganic bases) are used as reagents.

In the case of performing Vilsmeier-Haack reaction in each step, phosphoryl chloride and an amide derivative (e.g., N,N-dimethylformamide, etc.) are used as reagents.

In the case of performing the azidation reaction of alcohols, alkyl halides, or sulfonic acid esters in each step, examples of the azidation agent used include diphenylphosphorylazide (DPPA), trimethylsilyl azide, sodium azide, and the like. For the azidation of alcohols, for example, a method using diphenylphosphorylazide and 1,8-diazabicyclo[5,4,0]undec-7-ene (DBU), a method using trimethylsilyl azide and a Lewis acid, or the like is used.

In the case of performing reductive amination reaction in each step, examples of the reducing agent used include sodium triacetoxy borohydride, sodium cyanoborohydride, hydrogen, formic acid, and the like. When a substrate is an amine compound, examples of the carbonyl compound used include paraformaldehyde as well as aldehydes such as acetaldehyde and the like and ketones such as cyclohexanone and the like. When a substrate is a carbonyl compound, examples of the amines used include primary amines such as ammonia, methylamine, and the like; secondary amines such as dimethylamine and the like; etc.

In the case of performing Mitsunobu reaction in each step, azodicarboxylic acid esters (e.g., diethyl azodicarboxylate (DEAD), diisopropyl azodicarboxylate (DIAD), etc.) and triphenylphosphine are used as reagents.

In the case of performing esterification reaction, amidation reaction, or urea formation reaction in each step, examples of the reagent used include acyl halides such as acid chloride, acid bromide, and the like; acid anhydrides, active esters, and activated carboxylic acids such as sulfuric acid ester and the like. Examples of the activator for carboxylic acids include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonic acid ester condensing agents such as 1,1'-carbonyldiimidazole (CDI) and the like; diphenylphosphorylazide (DPPA); benzotriazol-1-yloxy-trisdimethylamino phosphonium salt (BOP reagent); 2-chloro-1-methyl-pyridinium iodide (Mukaiyama reagent); thionyl chloride; lower alkyl halo-formates such as ethyl chloroformate and the like; O-(7-azabenzotriazol-1-yl)-N,N,N',N'-tetramethyluronium hexafluorophosphate (HATU); sulfuric acid; combinations thereof; etc. In the case of using a carbodiimide condensing agent, an additive such as 1-hydroxybenzotriazole (HOBt), N-hydroxysuccinimide (HOSu), dimethylaminopyridine (DMAP), or the like may be further added to the reaction.

In the case of performing coupling reaction in each step, examples of the metal catalyst used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, and the like; platinum compounds; etc. A base may be further added to the reaction. Examples of such a base include inorganic bases, basic salts, and the like.

In the case of performing thiocarbonylation reaction in each step, typically, diphosphorus pentasulfide is used as a thiocarbonylation agent. In addition to diphosphorus pentasulfide, a reagent having a 1,3,2,4-dithiadiphosphetane-2,4-disulfide structure, such as 2,4-bis(4-methoxyphenyl-1,3,2,4-dithiadiphosphetane-2,4-disulfide (Lawesson's reagent) or the like may be used.

In the case of performing Wohl-Ziegler reaction in each step, examples of the halogenating agent used include N-iodosuccinimide, N-bromosuccinimide (NBS), N-chlorosuccinimide (NCS), bromine, sulfuryl chloride, and the like. Heat, light, or a radical initiator such as benzoyl peroxide, azobisisobutyronitrile, or the like can be added to the reaction to thereby accelerate the reaction.

In the case of performing the halogenation reaction of a hydroxy group in each step, examples of the halogenating agent used include a hydrohalic acid and an acid halide of an inorganic acid, specifically, hydrochloric acid, thionyl chloride, phosphorus oxychloride, or the like for chlorination, and 48% hydrobromic acid or the like for bromination. Also, a method for obtaining an alkyl halide from an alcohol by the action of triphenylphosphine and carbon tetrachloride or carbon tetrabromide, etc. may be used. Alternatively, a method for synthesizing an alkyl halide through two reaction steps involving the conversion of an alcohol to sulfonic acid ester and subsequent reaction with lithium bromide, lithium chloride, or sodium iodide, may be used.

In the case of performing Arbuzov reaction in each step, examples of the reagent used include alkyl halides such as ethyl bromoacetate and the like; and phosphites such as triethylphosphite, tri(isopropyl)phosphite, and the like.

In the case of performing sulfone esterification reaction in each step, examples of the sulfonating agent used include methanesulfonyl chloride, p-toluenesulfonyl chloride, methanesulfonic anhydride, p-toluenesulfonic anhydride, and the like.

In the case of performing hydrolysis reaction in each step, an acid or a base is used as a reagent. For the acid hydrolysis reaction of t-butyl ester, formic acid, triethylsilane, or the like may be added in order to reductively trap t-butyl cation by-products.

In the case of performing dehydration reaction in each step, examples of the dehydrating agent used include sulfuric acid, diphosphorus pentaoxide, phosphorus oxychloride, N,N'-dicyclohexylcarbodiimide, alumina, polyphosphoric acid, and the like.

Compound (1) can be produced from compound (2) by a method mentioned below.

[Chem. 16]

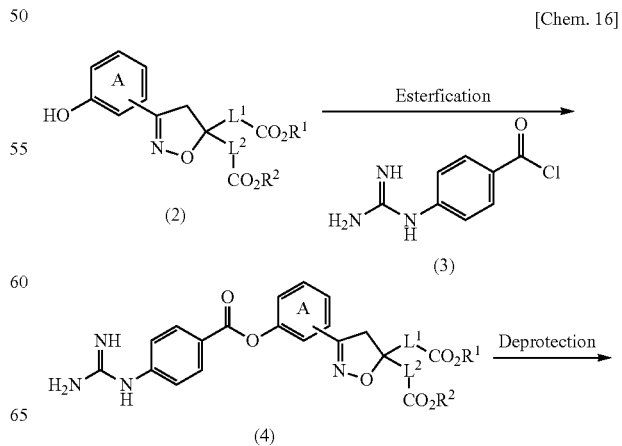

27

-continued

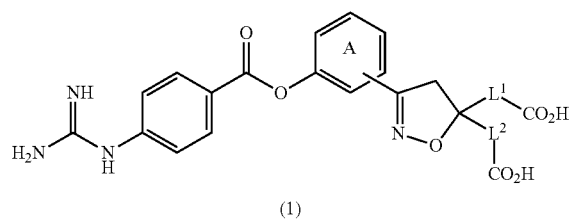

(1)

wherein $R^1$ and $R^2$ each represent a protecting group for the carboxyl group, and other symbols are as defined above.

Compound (1) can also be produced from compound (2-1) by the following method.

[Chem. 17]

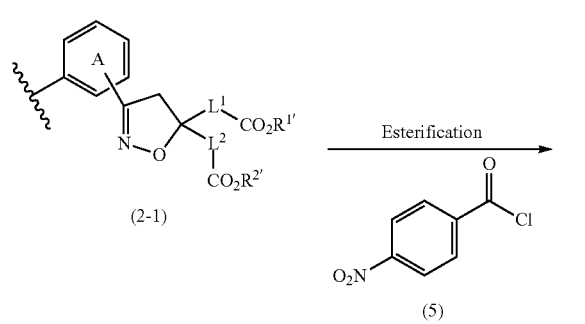

28

-continued

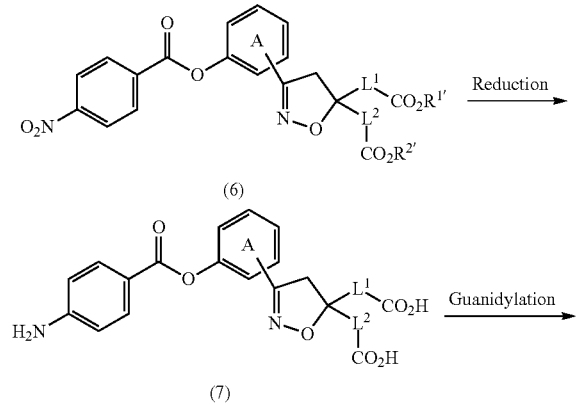

wherein $R^{1'}$ and $R^{2'}$ each represent a protecting group for the carboxyl group that can be deprotected by reduction reaction, and other symbols are as defined above.

Compound (1) can be produced by reaction of (7) with cyanamide under an acidic condition.

Compounds (2) and (2-2) can be produced from compound (8) by a method mentioned below.

[Chem. 18]

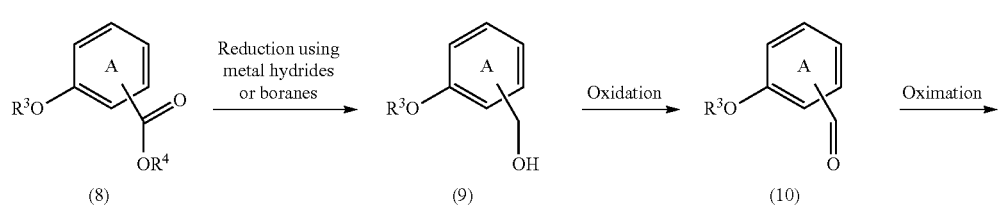

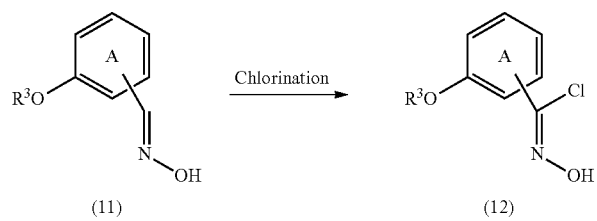

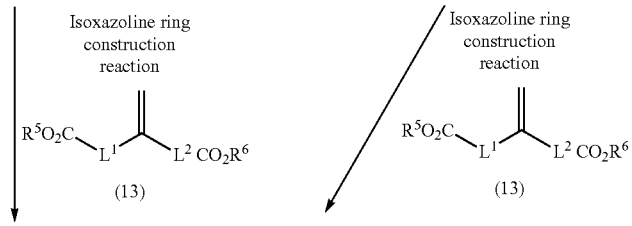

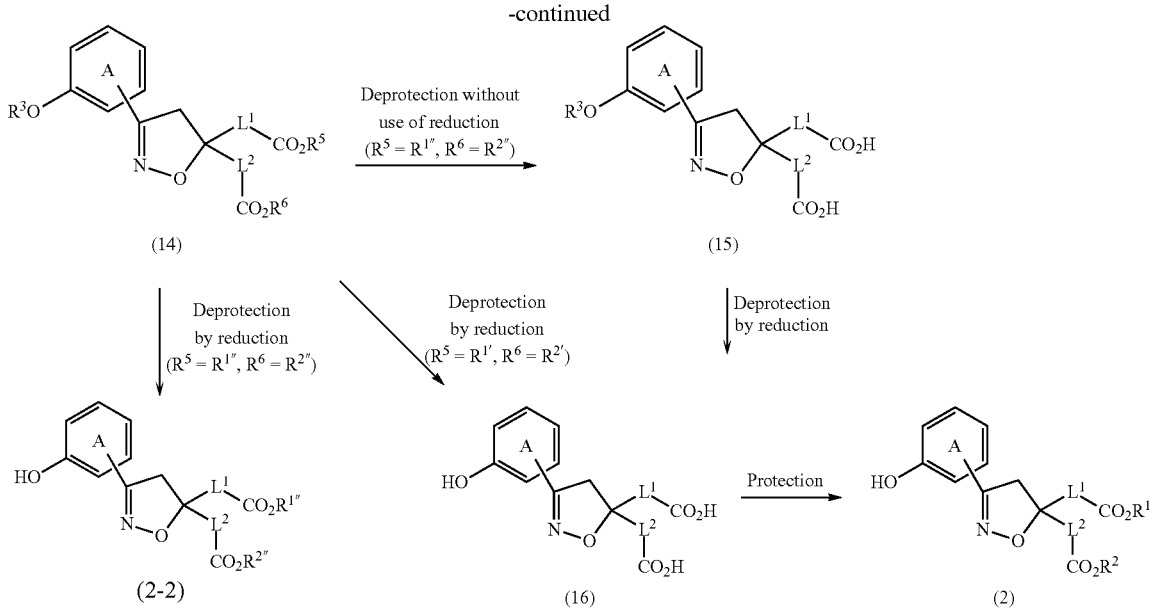

wherein $R^{1''}$ and $R^{2''}$ each represent a protecting group for the carboxyl group that is not deprotected by reduction reaction; $R^3$ represents a protecting group for the phenolic hydroxyl group that can be deprotected by reduction reaction (provided that the protecting group is not deprotected by reduction reaction using metal hydrides or boranes); $R^4$ represents hydrogen or an optionally substituted $C_{1-6}$ alkyl group; $R^5$ and $R^6$ each represent a protecting group for the carboxyl group; and other symbols are as defined above.

Compound (11) can be produced by the reaction of compound (10) with hydroxyl ammonium chloride in the presence of a base.

Compound (12) can be produced by the chlorination reaction of compound (11) using a chlorinating agent. Examples of the chlorinating agent include N-chlorosuccinimide and the like.

Compound (14) can be produced by the cyclization reaction of compound (11) with compound (13) in the presence of an oxidizing agent. Examples of the oxidizing agent include sodium hypochlorite and the like.

Compound (14) can also be produced by the cyclization reaction of compound (12) with compound (13) in the presence of a base.

Compound (13-1) can be produced from compound (17) or compound (18) by a method mentioned below.

[Chem. 19]

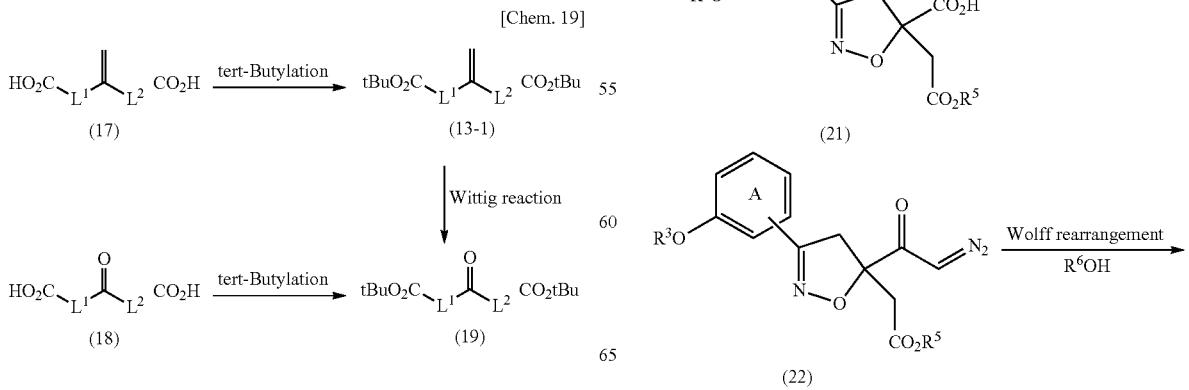

wherein all the symbols are as defined above.

Compound (13-1) can be produced by the tert-butylation reaction of compound (17) using a tert-butylating agent. Examples of the tert-butylating agent include 2-methylprop-1-ene, 1,1-di-tert-butoxy-N,N-dimethylmethanamine and the like. If necessary, this reaction may be performed in the presence of an acid.

Compound (19) can be produced by the tert-butylation reaction of compound (18) using a tert-butylating agent. Examples of the tert-butylating agent include 2-methylprop-1-ene, 1,1-di-tert-butoxy-N,N-dimethylmethanamine and the like. If necessary, this reaction may be performed in the presence of an acid.

Compound (14-1) can be produced from compound (11) by a method mentioned below.

[Chem. 20]

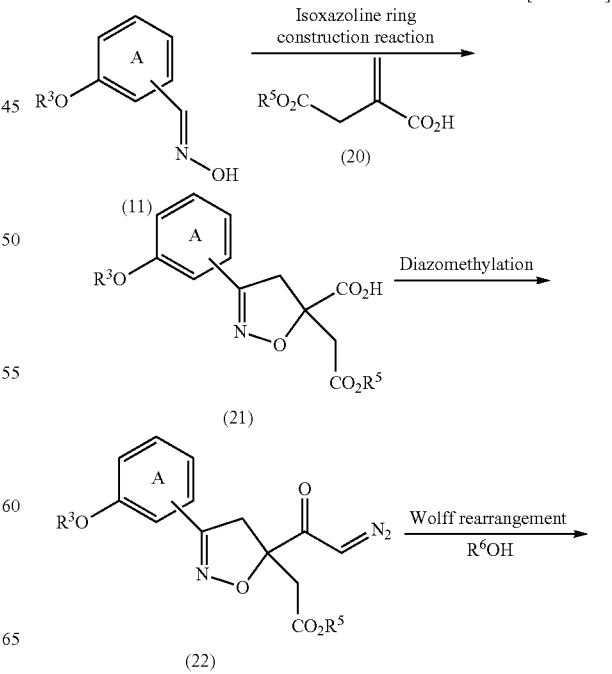

-continued

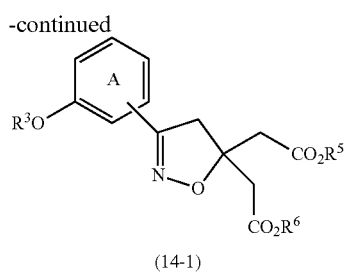

(14-1)

wherein all the symbols are as defined above.

Compound (22) can be produced by the conversion of compound (21) to acid chloride using oxalyl dichloride or the like followed by reaction with a diazomethylating agent. Examples of the diazomethylating agent include diazomethane, trimethylsilyldiazomethane and the like.

Compound (14-1) can be produced by the Wolff rearrangement reaction of compound (22) in the presence of a silver catalyst and an alcohol represented by $R^6OH$. Examples of the silver catalyst include silver benzoate, silver oxide and the like.

Compounds (2-3), (2-4), (2-5), and (2-6) can be produced from compound (14-2) by a method mentioned below.

[Chem. 21]

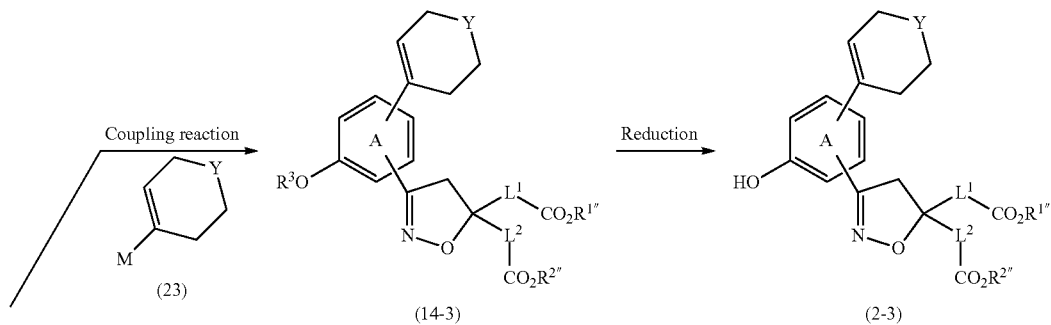

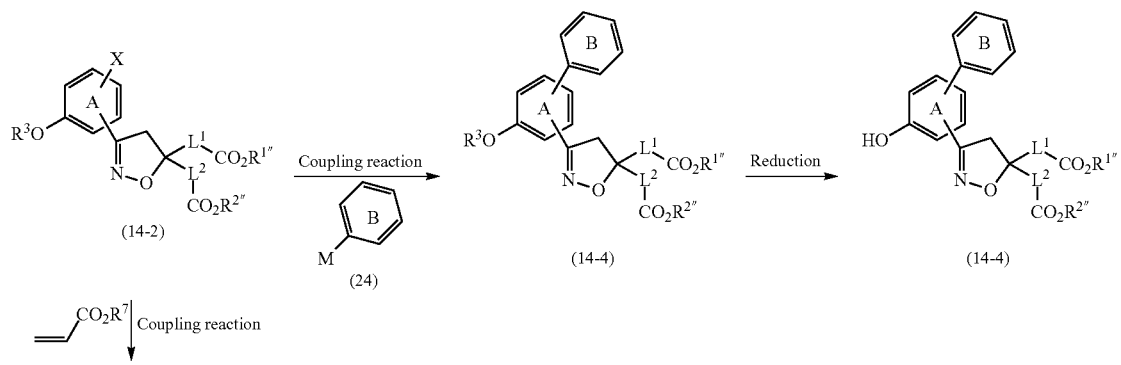

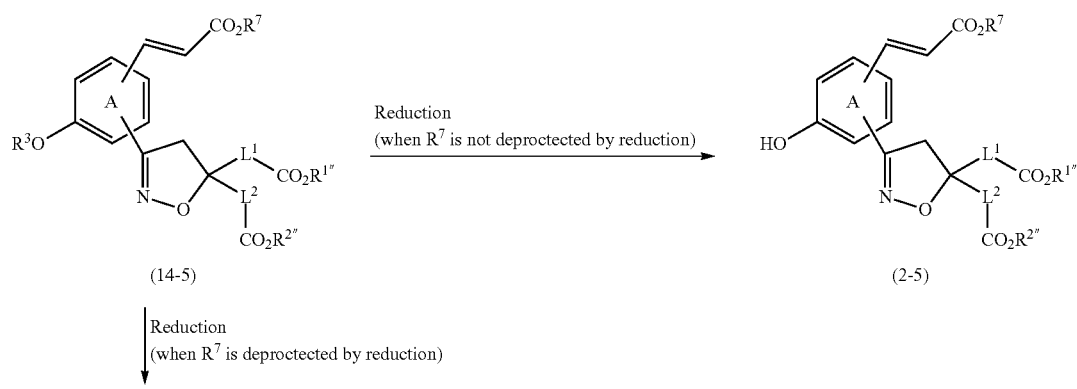

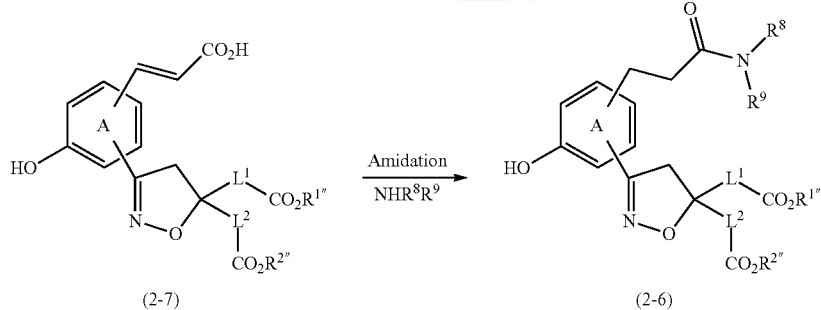

(2-7) → Amidation NHR⁸R⁹ → (2-6)

wherein $R^7$ represents a protecting group for the carboxyl group; $R^8$ and $R^9$ each represent a substituent; ring B represents a benzene ring or pyridine ring, each of which is optionally substituted; X represents chlorine, bromine, iodine, or triflate; Y represents optionally substituted carbon, nitrogen, oxygen, or optionally oxidized sulfur; M represents an optionally substituted metal; and other symbols are as defined above.

Compound (23-1) can be produced from compound (23-2) by a method mentioned below.

[Chem. 22]

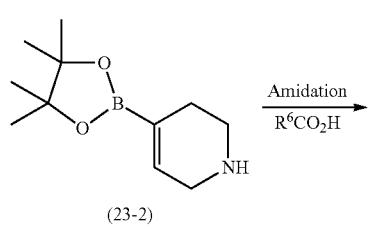

(23-2) → Amidation R⁶CO₂H → (23-1)

wherein all the symbols are as defined above.

Compound (23-3) can be produced from compound (23-2) by a method mentioned below.

[Chem. 23]

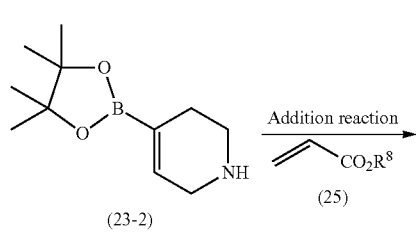

(23-2) → Addition reaction (25) → (23-3)

wherein all the symbols are as defined above.

Compound (23-3) can be produced by the addition reaction of compound (23-2) and compound (25) in the presence of a base.

Compound (4-3) can be produced from compound (2-7) by a method mentioned below.

[Chem. 24]

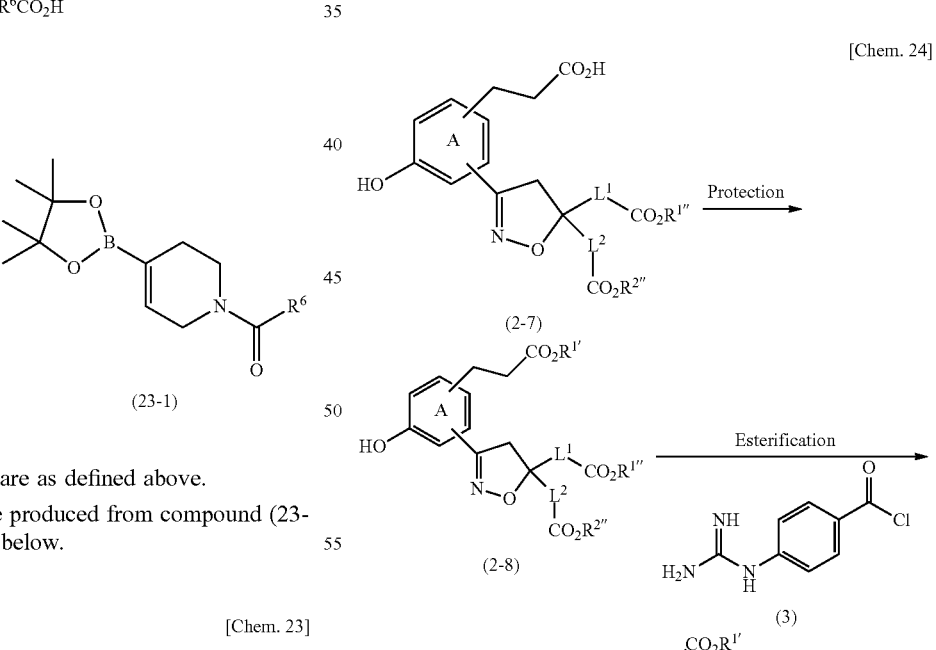

(2-7) → Protection → (2-8) → Esterification (3) → (4-1) → Deprotection by reduction →

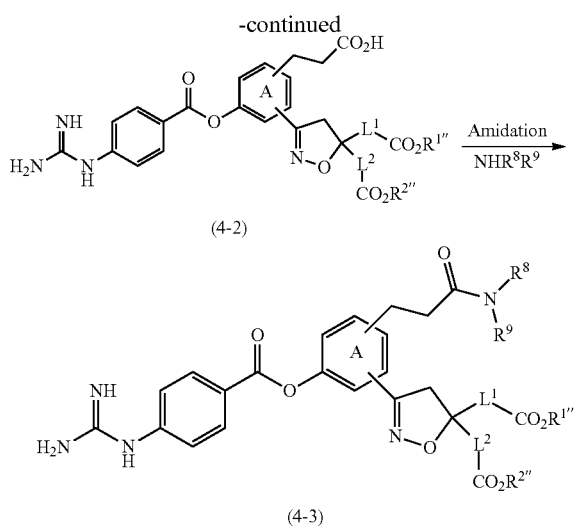

(4-2)

(4-3)

wherein all the symbols are as defined above.

Compound (2-2) can also be produced from compound (15) by a method mentioned below.

[Chem. 25]

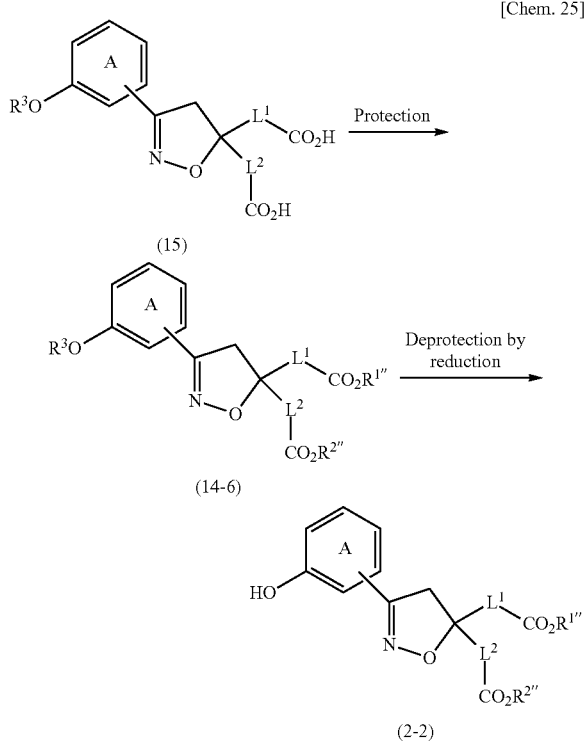

(15)

(14-6)

(2-2)

wherein all the symbols are as defined above.

Compound (I) may have isomers such as optical isomers, stereoisomers, positional isomers, rotational isomers and the like. In such a case, all of these isomers and mixtures thereof are also included in compound (I). For example, when compound (I) has optical isomers, optical isomers resolved from a racemate are also included in compound (I). These isomers can each be obtained as a single compound by synthesis approaches, separation approaches (e.g., concentration, solvent extraction, column chromatography, recrystallization, etc.), optical resolution approaches (e.g., frac- tional crystallization method, chiral column method, diastereomer method, etc.) and the like known per se.

Compound (I) may be crystals. Single crystal forms and polymorphic mixtures are both included in compound (I). The crystals can be produced by crystallizing compound (I) by the application of a crystallization method known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

In the present specification, a melting point means a melting point that is measured using, for example, a micro melting point apparatus (Yanaco model MP-500D or Buchi model B-545) or a DSC (differential scanning calorimetry) apparatus (SEIKO EXSTAR6000), etc.

In general, melting points may vary depending on a measurement apparatus, measurement conditions, etc. In the present specification, the crystals may be crystals that exhibit a value different from the melting points described herein, as long as the value falls within a margin of error.

The crystals of the present invention are excellent in physicochemical properties (e.g., melting point, solubility, stability) and biological properties (e.g., disposition (absorption property, distribution, metabolism, excretion), manifestation of efficacy) and are very useful as a medicament.

Compound (I) may be a solvate (e.g., a hydrate, etc.) or may be non-solvate (e.g., a non-hydrate, etc.). All of them are included in compound (I).

A compound labeled with an isotope (e.g., $^3$H, $^{13}$C, $^{14}$C, $^{18}$F, $^{35}$S, $^{125}$I, etc.) or the like is also included in compound (I).

A deuterium conversion form wherein $^1$H is converted to $^2$H(D) is also included in compound (I).

Compound (I) labeled or substituted with an isotope can be used as, for example, a tracer (PET tracer) for use in Positron Emission Tomography (PET), and is useful in the fields of medical diagnosis and the like.

Compound (I) or a prodrug thereof (hereinafter to be abbreviated collectively as the compound of the present invention) has a superior enteropeptidase inhibitory action, particularly, in vivo, and is useful as an enteropeptidase inhibitor.

Also, the compound of the present invention has a feeding suppressive action and a body weight-lowering action.

The compound of the present invention has low toxicity (e.g., acute toxicity, chronic toxicity, genetic toxicity, reproductive toxicity, cardiac toxicity, carcinogenicity). Thus, the compound of the present invention can be prepared into a pharmaceutical composition alone or in admixture with a pharmacologically acceptable carrier or the like and thereby administered safely in a mammal (e.g., mouse, rat, hamster, rabbit, cat, dog, bovine, sheep, monkey, human).

The compound of the present invention is useful as an agent for the prophylaxis or treatment of disease states or diseases caused by enteropeptidase.

Also, the compound of the present invention is low absorbable orally and is excellent in metabolic stability.

Specifically, the compound of the present invention can be used as an agent for the prophylaxis or treatment of obesity based on symptomatic obesity or simple obesity, disease states or diseases associated with obesity, eating disorder, diabetes mellitus (e.g., type 1 diabetes mellitus, type 2 diabetes mellitus, gestational diabetes mellitus, obese diabetes mellitus), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia, reflux esophagitis and the like.

The compound of the present invention is particularly useful as an agent for the prophylaxis or treatment of obesity or an agent for the prophylaxis or treatment of diabetes mellitus on the basis of its enteropeptidase inhibitory action.

Examples of the symptomatic obesity include endocrine obesity (e.g., Cushing syndrome, hypothyroidism, insulinoma, obese type II diabetes mellitus, pseudohypoparathyroidism, hypogonadism), central obesity (e.g., hypothalamic obesity, frontal lobe syndrome, Kleine-Levin syndrome), genetic obesity (e.g., Prader-Willi syndrome, Laurence-Moon-Biedl syndrome), drug-induced obesity (e.g., obesity caused by steroids, phenothiazines, insulins, sulfonylurea (SU) agents, beta-blockers) and the like.

Examples of the disease states or diseases associated with obesity include impaired glucose tolerance, diabetes mellitus (particularly, type 2 diabetes mellitus, obese diabetes mellitus), abnormal lipid metabolism (which has the same meaning as that of the hyperlipidemia mentioned above), hypertension, cardiac failure, hyperuricemia/gout, fatty liver (including non-alcoholic steato-hepatitis), coronary diseases (myocardial infarction, angina pectoris), cerebral infarction (cerebral thrombosis, transient ischemic attack), bone or joint diseases (knee osteoarthritis, hip osteoarthritis, spondylosis deformans, lumbago), sleep apnea syndrome/Pickwick syndrome, menstruation disorder (disorder of menstrual cycle, abnormality of the amount of blood lost at menstrual period and menstrual cycle, amenorrhea, abnormality of menstruation-related symptoms), metabolic syndrome and the like.

The Japan Diabetes Society reported the diagnostic criteria of diabetes mellitus in 1999.

According to this report, diabetes mellitus refers to a state that meets any of a fasting blood glucose level (glucose concentration in venous plasma) of 126 mg/dl or more, a 2-hr value (glucose concentration in venous plasma) of 200 mg/dl or more in the 75 g oral glucose tolerance test (75 g OGTT), and a casual blood glucose level (glucose concentration in venous plasma) of 200 mg/dl or more. Also, a state that does not apply to the above-mentioned diabetes mellitus, and is not a state exhibiting "a fasting blood glucose level (glucose concentration in venous plasma) less than 110 mg/dl or a 2-hr value (glucose concentration in venous plasma) less than 140 mg/dl in the 75 g oral glucose tolerance test (75 g OGTT)" (normal type) is called "borderline type".

Also, the diagnostic criteria of diabetes mellitus were reported in 1997 by ADA (American Diabetes Association) and in 1998 by WHO (World Health Organization).

According to these reports, diabetes mellitus refers to a state that meets a fasting blood glucose level (glucose concentration in venous plasma) of 126 mg/dl or more and a 2-hr value (glucose concentration in venous plasma) of 200 mg/dl or more in the 75 g oral glucose tolerance test According to the above-mentioned reports of ADA and WHO, impaired glucose tolerance (IGT) refers to a state that meets a fasting blood glucose level (glucose concentration in venous plasma) less than 126 mg/dl and a 2-hr value (glucose concentration in venous plasma) of 140 mg/dl or more and less than 200 mg/dl in the 75 g oral glucose tolerance test. According to the report of ADA, a state exhibiting a fasting blood glucose level (glucose concentration in venous plasma) of 110 mg/dl or more and less than 126 mg/dl is called IFG (Impaired Fasting Glucose). On the other hand, according to the report of WHO, a state of IFG (Impaired Fasting Glucose) exhibiting a 2-hr value (glucose concentration in venous plasma) less than 140 mg/dl in the 75 g oral glucose tolerance test is called IFG (Impaired Fasting Glucose).

The compound of the present invention is also used as an agent for the prophylaxis or treatment of diabetes mellitus, borderline type diabetes mellitus, impaired glucose tolerance, IFG (Impaired Fasting Glucose) and IFG (Impaired Fasting Glycemia) determined according to the above-mentioned diagnostic criteria. Moreover, the compound of the present invention can prevent progress of borderline type, impaired glucose tolerance, IFG (Impaired Fasting Glucose) or IFG Impaired Fasting Glycemia) into diabetes mellitus.

The compound of the present invention has an action of suppressing body weight gain and as such, can be used as an agent for suppressing body weight gain in a mammal. The mammal to which the compound of the present invention is to be applied can be a mammal desired to avoid body weight gain and may be a mammal genetically having a risk of body weight gain or may be a mammal affected by a lifestyle-related disease such as diabetes mellitus, hypertension and/or hyperlipidemia, etc. The body weight gain may be caused by excessive dietary intakes or nutritionally unbalanced diets or may be derived from concomitant drugs (e.g., insulin sensitizers and the like having a PPAR-gamma agonist-like action, such as troglitazone, rosiglitazone, englitazone, ciglitazone, pioglitazone and the like). Also, the body weight gain may be body weight gain before reaching obesity or may be body weight gain in an obesity patient. In this context, the obesity is defined as having BMI (body mass index: Body weight (kg)/[Height (m)]$^2$) of 25 or more (according to the criteria of the Japan Society for the Study of Obesity (JASSO)) for Japanese or having BMI of 30 or more (according to the criteria of WHO) for Westerners.

The compound of the present invention is also useful as an agent for the prophylaxis or treatment of metabolic syndrome. The incidence of cardiovascular disease is significantly high in metabolic syndrome patients, compared with patients with a single lifestyle-related disease. Thus, the prophylaxis or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL) and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for the prophylaxis or treatment of, for example, osteoporosis, cachexia (e.g., cancerous cachexia, tuberculous cachexia, diabetic cachexia, cachexia associated with blood disease, cachexia associated with endocrine disease, cachexia associated with infectious disease or cachexia caused by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disease), muscular dystrophy, myocardial infarction, angina pectoris, cerebrovascular disorder (e.g., cerebral infarction, stroke), Alzheimer's disease, Parkinson's disease, anxiety disorder, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, gastric mucosal injury (including gastric mucosal injury caused by aspirin)), small intestinal mucosal injury, malabsorption, testicular dysfunction, visceral obesity syndrome and sarcopenia.

Moreover, the compound of the present invention can also be used as an agent for the prophylaxis or treatment of various cancers (particularly, breast cancer (e.g., invasive ductal breast cancer, noninvasive ductal breast cancer, inflammatory breast cancer, etc.), prostate cancer (e.g., hormone-dependent prostate cancer, hormone-independent prostate cancer, etc.), pancreatic cancer (e.g., ductal pancreatic cancer, etc.), gastric cancer (e.g., papillary adenocarcinoma, mucous adenocarcinoma, adenosquamous carcinoma, etc.), lung cancer (e.g., non-small cell lung cancer, small-cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small intestinal cancer (e.g., non-Hodgkin's lymphoma, gastrointestinal stromal tumor, etc.), esophageal cancer, duodenal cancer, tongue cancer, pharyngeal cancer (e.g., nasopharyngeal cancer, oropharynx cancer, hypopharyngeal cancer, etc.), salivary gland cancer, brain tumor (e.g., pineal astrocytoma, pilocytic astrocytoma, diffuse astrocytoma, anaplastic astrocytoma, etc.), neurilemmoma, liver cancer (e.g., primary liver cancer, extrahepatic bile duct cancer, etc.), renal cancer (e.g., renal cell cancer, transitional cell cancer of the renal pelvis and ureter, etc.), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential, etc.), bladder cancer, urethral cancer, skin cancer (e.g., intraocular (ocular) melanoma, Merkel cell carcinoma, etc.), hemangioma, malignant lymphoma, malignant melanoma, thyroid cancer (e.g., medullary thyroid cancer, etc.), parathyroid cancer, nasal cavity cancer, sinus cancer, bone tumor (e.g., osteosarcoma, Ewing tumor, uterine sarcoma, soft tissue sarcoma, etc.), angiofibroma, sarcoma of the retina, penis cancer, testicular tumor, pediatric solid tumor (e.g., Wilms' tumor, childhood kidney tumor, etc.), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia, acute lymphoblastic leukemia, etc.), etc.).

The compound of the present invention can also be used for secondary prevention or suppression of progression of the above-mentioned various diseases (e.g., cardiovascular events such as myocardial infarction and the like).

A medicament comprising the compound of the present invention can be obtained using the compound of the present invention alone or in admixture with a pharmacologically acceptable carrier according to a method known per se (e.g., a method described in the Japanese Pharmacopoeia, etc.) as a method for producing pharmaceutical preparations, and safely administered orally or parenterally (e.g., administered intravenously, intramuscularly, subcutaneously, into an organ, into a nasal cavity, intracutaneously, through ocular instillation, intracerebrally, rectally, vaginally, intraperitoneally, to the inside of tumor, to the proximity of tumor, and the like, and administered directly to a lesion) to a mammal as, for example, tablets (inclusive of sugar-coated tablets, film-coated tablets, sublingual tablets, orally disintegrating tablets, buccal tablets, and the like), pills, powders, granules, capsules (inclusive of soft capsules, microcapsules), troches, syrups, liquids, emulsions, suspensions, controlled release preparations (e.g., rapid release preparations, sustained release preparations, sustained release microcapsules), aerosols, films, (e.g., orally disintegrating films, patch films for application to the oral mucosa), injections (e.g., subcutaneous injections, intravenous injections, intramuscular injections, intraperitoneal injections), transfusions, dermal preparations, ointments, lotions, patches, suppositories (e.g., rectal suppositories, vaginal suppositories), pellets, nasal preparations, pulmonary preparations (inhalants), eye drops, and the like.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The content of the compound of the present invention in the pharmaceutical preparation is about 0.01 to about 100 wt % of the whole preparation. The dosage differs depending on the subject of administration, administration route, disease, symptom and the like. For example, when the compound of the present invention is orally administered to a diabetes mellitus patient (body weight: about 60 kg), a daily dose is about 0.01 to about 30 mg/kg body weight, preferably about 0.1 to about 20 mg/kg body weight, more preferably about 1 to about 20 mg/kg body weight, of the active ingredient [compound of the present invention]. This dose can be administered at once or in several portions per day (e.g., in one to three portions per day).

Examples of the pharmacologically acceptable carrier mentioned above include various organic or inorganic carrier materials that are conventionally used as preparation materials. Examples thereof include: excipients, lubricants, binding agents, and disintegrants for solid preparations; solvents, solubilizing agents, suspending agents, isotonic agents, buffering agents, and soothing agents for liquid preparations; and the like.

Further, if necessary, conventional additives such as preservative, antioxidant, colorant, sweetening agent, adsorbent, wetting agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethyl starch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzethonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include: buffer solutions such as phosphates, acetates, carbonates, citrates and the like; and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, alpha-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., beta-carotene, chlorophyll, ferric oxide red) and the like.

Examples of the sweetening agent include saccharin sodium, dipotassium glycyrrhizinate, aspartame, stevia and the like.

Further, the compound of the present invention can be used in combination with a drug other than the compound of the present invention.

Examples of the drug (hereinafter sometimes to be abbreviated as a concomitant drug) that may be used in combination with the compound of the present invention include antiobesity agents, therapeutic agents for diabetes mellitus, therapeutic agents for diabetic complications, therapeutic agents for hyperlipidemia, antihypertensive agents, diuretics, chemotherapeutic agents, immunotherapeutic agents, anti-inflammatory drugs, antithrombotic agents, therapeutic agents for osteoporosis, vitamins, antidementia drugs, drugs for the amelioration of erectile dysfunction, therapeutic drugs for pollakiuria or urinary incontinence, therapeutic agent for difficulty of urination and the like. Specific examples thereof include the following.

Examples of the antiobesity agent include monoamine uptake inhibitors (e.g., phentermine, sibutramine, mazindol, fluoxetine, tesofensine), serotonin 2 C receptor agonists (e.g., lorcaserin), serotonin 6 receptor antagonists, histamine H3 receptor modulators, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11 beta-hydroxysteroid dehydrogenase inhibitors (e.g., AZD-4017), pancreatic lipase inhibitors (e.g., orlistat, cetilistat), beta 3 agonists (e.g., N-5984), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NF kappa inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized by using *Escherichia. coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57) and the like.

Here, as the therapeutic agent for diabetes mellitus, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), alpha-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof), dipeptidyl peptidase IV inhibitors (e.g., Alogliptin or a salt thereof (preferably, benzoate), Trelagliptin or a salt thereof (preferably, succinate), Vildagliptin, Sitagliptin, Saxagliptin, BI1356, GRC8200, MP-513, PF-00734200, PHX1149, SK-0403, ALS2-0426, TA-6666, TS-021, KRP-104, beta-3 agonists (e.g., N-5984), GPR40 agonists (e.g., fasiglifam, compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1 MR preparations, liraglutide, exenatide, AVE-0010, BIM-51077, Aib(8, 35)hGLP-1(7,37)NH$_2$, CJC-1131, albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Dapagliflozin, AVE2268, TS-033, YM543, TA-7284, Remogliflozin, ASP1941), SGLT1 inhibitors, 11 beta-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonist (e.g. PSN821, MBX-2982, APD597), FGF21, FGF analog and the like can be mentioned.

As the therapeutic agent for diabetic complications, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxyl)propyl] oxazole), compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (gamma-oryzanol)), cholesterol absorption inhibitors (e.g., zechia), CETP inhibitors (e.g., dalcetrapib, anacetrapib), omega-3 fatty acid preparations (e.g., omega-3-fatty acid ethyl esters 90 (omega-3-acid ethyl esters 90)) and the like can be mentioned.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine, etc.), beta blockers (e.g., metoprolol, atenolol, propranolol, carvedilol, pindolol, etc.), clonidine and the like.

As the diuretic, for example, xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, benzylhydrochlorothiazide, penfluthiazide, poly 5 thiazide, methyclothiazide, etc.), antialdosterone preparations (e.g., spironolactone, triamterene, etc.), carbonic anhydrase inhibitors (e.g., acetazolamide, etc.), chlorobenzenesulfonamide agents (e.g., chlortalidone, mefruside, indapamide, etc.), azosemide, isosorbide, ethacrynic acid, piretanide, bumetanide, furosemide and the like can be mentioned.

Examples of the chemotherapeutic agent include alkylating agents (e.g., cyclophosphamide, ifosfamide), antimetabolites (e.g., methotrexate, 5-fluorouracil), anticancer antibiotics (e.g., mitomycin, adriamycin), plant-derived anticancer agents (e.g., vincristine, vindesine, Taxol), cisplatin, carboplatin, etoposide and the like. Among others, a 5-fluorouracil derivative Furtulon or Neofurtulon or the like is preferable.

Examples of the immunotherapeutic agent include microbial or bacterial components (e.g., muramyl dipeptide derivative, Picibanil), polysaccharides having immunoenhancing activity (e.g., lentinan, sizofiran, Krestin), cytokines obtained by genetic engineering approaches (e.g., interferon, interleukin (IL)), colony-stimulating factors (e.g., granulocyte colony-stimulating factor, erythropoietin) and the like. Among others, interleukins such as IL-1, IL-2, IL-12 and the like are preferable.

Examples of the anti-inflammatory drug include non-steroidal anti-inflammatory drugs such as aspirin, acetaminophen, indomethacin and the like.

As the antithrombotic agent, heparin (e.g., heparin sodium, heparin calcium, enoxaparin sodium, dalteparin sodium), warfarin (e.g., warfarin potassium), anti-thrombin drugs (e.g., aragatroban, dabigatran), Fxa inhibitors (e.g., rivaroxaban, apixaban, edoxaban, YM150, compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like can be mentioned.

Examples of the therapeutic agent for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamin include vitamin $B_1$, vitamin $B_{12}$ and the like.

Examples of the antidementia drug include tacrine, donepezil, rivastigmine, galanthamine and the like.

Examples of the drug for the amelioration of erectile dysfunction include apomorphine, sildenafil citrate and the like.

Examples of the therapeutic drug for pollakiuria or urinary incontinence include flavoxate hydrochloride, oxybutynin hydrochloride, propiverine hydrochloride and the like.

Examples of the therapeutic agent for difficulty of urination include acetylcholine esterase inhibitors (e.g., distigmine) and the like.

Moreover, a drug confirmed to have a cachexia-ameliorating action either in animal models or clinically, i.e., a cyclooxygenase inhibitor (e.g., indomethacin), a progesterone derivative (e.g., megestrol acetate), glucocorticoid (e.g., dexamethasone), a metoclopramide drug, a tetrahydrocannabinol drug, an agent for improving fat metabolism (e.g., eicosapentaenoic acid), growth hormone, IGF-1, or an antibody against a cachexia-inducing factor TNF-alpha, LIF, IL-6 or oncostatin M or the like can also be used in combination with the compound of the present invention.

Alternatively, a glycation inhibitor (e.g., ALT-711), a nerve regeneration-promoting drug (e.g., Y-128, VX853, prosaptide), an antidepressant (e.g., desipramine, amitriptyline, imipramine), an antiepileptic drug (e.g., lamotrigine, Trileptal, Keppra, Zonegran, Pregabalin, Harkoseride, carbamazepine), an antiarrhythmic drug (e.g., mexiletine), an acetylcholine receptor ligand (e.g., ABT-594), an endothelin receptor antagonist (e.g., ABT-627), a monoamine uptake inhibitor (e.g., tramadol), a narcotic analgesic (e.g., morphine), a GABA receptor agonist (e.g., gabapentin, MR preparation of gabapentin), an alpha 2 receptor agonist (e.g., clonidine), a local analgesic (e.g., capsaicin), an antianxiety drug (e.g., benzothiazepine), a phosphodiesterase inhibitor (e.g., sildenafil), a dopamine receptor agonist (e.g., apomorphine), midazolam, ketoconazole or the like may be used in combination with the compound of the present invention.

In the case of using the compound of the present invention and a concomitant drug in combination, the respective amounts of the drugs can be reduced within safe ranges in consideration of the side effects of the drugs. In addition, the dosage of the concomitant drug can be reduced. As a result, side effects that might be caused by the concomitant drug can be effectively prevented.

By combining the compound of the present invention and a concomitant drug, superior effects can be achieved, such as:

(1) the dose of the compound of the present invention or a concomitant drug can be reduced as compared to single administration of the compound of the present invention or a concomitant drug;

(2) the period of treatment can be set longer by selecting a concomitant drug having a different mechanism of action from that of the compound of the present invention;

(3) a sustained therapeutic effect can be designed by selecting a concomitant drug having a different mechanism of action from that of the compound of the present invention;

(4) a synergistic effect can be afforded by a combined use of the compound of the present invention and a concomitant drug;

and the like.

In the case of using the compound of the present invention and a concomitant drug in combination, the time of administration of the compound of the present invention and that of the concomitant drug are not limited, and the compound of the present invention and the concomitant drug may be administered simultaneously or in a staggered manner to the administration subject. The dose of the concomitant drug can conform to the dose employed in clinical situations and can be appropriately determined depending on the administration subject, administration route, disease, combination and the like.

Examples of the administration mode of the compound of the present invention and the concomitant drug include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

EXAMPLES

The present invention is explained in detail in the following by referring to the following Examples, Experimental Examples and Formulation Examples, which are not to be construed as limitative. In addition, the present invention may be modified without departing from the scope of invention.

The term "room temperature" in the following Examples indicates the range of generally from about 10 C to about 35 C. A ratio used for a mixed solvent indicates a volume ratio, unless otherwise specified. % indicates wt %, unless otherwise specified.

The term "NH" in silica gel column chromatography indicates that an aminopropylsilane-bound silica gel was used. The term "C18" in HPLC (high-performance liquid chromatography) indicates that an octadecyl-bound silica gel was used. A ratio used for elution solvents indicates a volume ratio, unless otherwise specified. Abbreviations described below are used in the following Examples.

mp: melting point
MS: mass spectrum
[M+H]$^+$, [M+Na]$^+$, [M−H]$^−$: molecular ion peak
M: molar concentration
N: normal
CDCl$_3$: deuterated chloroform
DMSO-d$_6$: deuterated dimethyl sulfoxide
$^1$H NMR: proton nuclear magnetic resonance
LC/MS: liquid chromatograph mass spectrometer
ESI: ElectroSpray Ionization
APCI: Atmospheric Pressure Chemical Ionization
THF: tetrahydrofuran
DME: 1,2-dimethoxyethane
DMF: N,N-dimethylformamide
DMA: N,N-dimethylacetamide
NMP: 1-methyl-2-pyrrolidone
TFA: trifluoroacetic acid
HATU: 2-(7-azabenzotriazol-1-yl)-1,1,3,3-tetramethyluronium hexafluorophosphate
HOBt: 1-hydroxybenzotriazole
WSC: 1-ethyl-3-(3-dimethylaminopropyl)carbodiimide $^1$H NMR was measured by Fourier transform type NMR. ACD/SpecManager (trade name) or the like was used in analysis. No mention was made about the very broad peaks of protons of a hydroxyl group, an amino group, and the like.

MS was measured using LC/MS. ESI or APCI was used as an ionization method. Data was indicated by actual measurement value (found). In general, molecular ion peaks are observed. In the case of a compound having a tert-butoxycarbonyl group, a fragment ion peak derived from the elimination of the tert-butoxycarbonyl group or the tert-butyl group may be observed. In the case of a compound having a hydroxyl group, a fragment ion peak derived from the elimination of H$_2$O may be observed. In the case of salt, a molecular ion peak or fragment ion peak of a free form is generally observed.

The unit of sample concentration (c) in optical rotation ([alpha]$_D$) is g/100 mL.

Element analysis values (Anal.) were indicated by calculation value (Calcd) and actual measurement value (Found).

Example 1

(5R)-3-(3-((4-Carbamimidamidobenzoyl)oxy)phenyl)-5-(carboxymethyl)-4,5-dihydro-1,2-oxazole-5-carboxylic acid A) 3-(3-(Benzyloxy)phenyl)-5-(carboxymethyl)-4,5-dihydro-1,2-oxazole-5-carboxylic acid An aqueous sodium hypochlorite solution (5%, 1081 g) was added dropwise to a solution of (E)-1-(3-(benzyloxy)phenyl)-N-hydroxymethanimine (150 g) and dimethyl 2-methylenesuccinate (104 g) in THF (1500 mL) at 5 C (internal temperature: 30 C or lower) over 1 hour, and then, the obtained mixture was stirred at 5 C for 1 hour. To the reaction mixture, methanol (750 mL) was added, and then, a 2 M aqueous sodium hydroxide solution (750 mL) was added dropwise at 5 C (internal temperature: 20 C or lower) over 40 minutes. The obtained mixture was gradually warmed to room temperature and stirred overnight at room temperature. The reaction mixture was concentrated into half the volume under reduced pressure, and then, water (5000 mL) and ethyl acetate (1500 mL) were added to the residue. The aqueous layer was washed with ethyl acetate (1500 mL), then 6 M hydrochloric acid (250 mL) was added thereto, and the obtained mixture was subjected to extraction with ethyl acetate (1500 mL×2). The extract was washed with brine (1500 mL) and dried over anhydrous magnesium sulfate, and then, the solvent was distilled off under reduced pressure. The residue was washed with diethyl ether (10 mL) and hexane (1000 mL) to obtain the title compound (217 g).

MS: [M+H]$^+$ 356.2.

B) (5R)-3-(3-(Benzyloxy)phenyl)-5-(carboxymethyl)-4,5-dihydro-1,2-oxazole-5-carboxylic acid cinchonidine salt 3-(3-(Benzyloxy)phenyl)-5-(carboxymethyl)-4,5-dihydro-1,2-oxazole-5-carboxylic acid (5 g) was added to a suspension of cinchonidine (3.73 g) in ethanol (50 mL) and acetonitrile (50 mL) at 50 C. The obtained suspension was stirred at 45 C to 50 C for 1 hour and subsequently at room temperature for 1 hour, and then, the solid was collected by filtration and washed with acetonitrile/ethanol (2/1) to obtain a crude product (4.4 g). The obtained crude product (4.4 g) was dissolved in DMSO (44 mL) at 70 C, and ethyl acetate (66 mL) and heptane (22 mL) were added in this order to the solution. The obtained suspension was stirred at 50 C for 30 minutes and at room temperature for 1 hour, and the solid was collected by filtration and washed with DMSO/ethyl acetate (1/5) and ethyl acetate in this order to obtain crude crystals (3.5 g). The obtained crude crystals (3.0 g) were dissolved in DMSO (30 mL) at 70 C, and ethyl acetate (45 mL) and heptane (15 mL) were added in this order to the solution. The obtained suspension was stirred at 50 C for 30 minutes and at room temperature for 1 hour, and the solid was collected by filtration and washed with DMSO/ethyl acetate (1/5) and ethyl acetate in this order to obtain the title compound (2.4 g).

$^1$H-NMR (300 MHz, DMSO-d$_6$) delta 1.47-1.65 (1H, m), 1.65-1.84 (1H, brs), 1.86-2.07 (3H, m), 2.51-2.68 (2H, m), 2.95-3.16 (2H, m), 3.16-3.58 (6H, m), 3.66-3.82 (1H, m), 3.82-3.96 (1H, m), 4.92-5.22 (4H, m), 5.70-5.92 (2H, m), 6.29 (1H, brs), 7.03-7.15 (1H, m), 7.19-7.52 (8H, m), 7.62-7.73 (2H, m), 7.73-7.86 (1H, m), 8.07 (1H, dd), 8.28 (1H, d), 8.91 (1H, d).

C) (5R)-3-(3-(Benzyloxy)phenyl)-5-(carboxymethyl)-4,5-dihydro-1,2-oxazole-5-carboxylic acid 1 N hydrochloric acid (5500 mL) was added to an suspension of (5R)-3-(3-(benzyloxy)phenyl)-5-(carboxymethyl)-4,5-dihydro-1,2-oxazole-5-carboxylic acid cinchonidine salt (553.3 g) in ethyl acetate (5500 mL) at room temperature. The obtained mixture was stirred at room temperature for 30 minutes. Then, the organic layer was separated, washed with brine, and dried over anhydrous sodium sulfate, and then, the solvent was distilled off under reduced pressure. The residue was washed with diisopropyl ether to obtain the title compound (303 g).

MS: [M+H]$^+$ 356.1.

D) Benzyl (5R)-5-(2-(benzyloxy)-2-oxoethyl)-3-(3-hydroxyphenyl)-4,5-dihydro-1,2-oxazole-5-carboxylate A mixture of (5R)-3-(3-(benzyloxy)phenyl)-5-(carboxymethyl)-4,5-dihydro-1,2-oxazole-5-carboxylic acid (75.0 g), 10% Pd/C (containing about 55% water, 7.5 g), and THF (750 mL) was stirred at room temperature for 15 hours under a hydrogen atmosphere. To the reaction mixture, methanol (150 mL) was added, then the catalyst was filtered and washed with methanol (375 mL). The filtrate was concentrated under reduced pressure to obtain (5R)-5-(carboxymethyl)-3-(3-hydroxyphenyl)-4,5-dihydro-1,2-oxazole-5-carboxylic acid as a crude product.

This crude product was combined with a crude product of (5R)-5-(carboxymethyl)-3-(3-hydroxyphenyl)-4,5-dihydro-1,2-oxazole-5-carboxylic acid obtained from (5R)-3-(3-(benzyloxy)phenyl)-5-(carboxymethyl)-4,5-dihydro-1,2-oxazole-5-carboxylic acid (75.5 g) by the same operation as above, and mixed with N,N-diisopropylethylamine (244 mL) and DMF (1100 mL). To the obtained solution, (bromomethyl)benzene (111 mL) was added at room temperature, and the mixture was stirred overnight at room temperature. The reaction mixture was added to 0.1 M hydrochloric acid (1100 mL), followed by extraction with ethyl acetate (1100 mL×2). The extract was washed with brine (1100 mL) and dried over anhydrous sodium sulfate, and then, the solvent was distilled off under reduced pressure. The residue was purified by silica gel column chromatography (ethyl acetate/hexane), and then, the obtained residue was washed with diisopropyl ether/hexane to obtain the title compound (131 g).

MS: $[M+H]^+$ 446.2.

E) Benzyl (5R)-5-(2-(benzyloxy)-2-oxoethyl)-3-(3-((4-nitrobenzoyl)oxy)phenyl)-4,5-dihydro-1,2-oxazole-5-carboxylate 4-Nitrobenzoyl chloride (105 g) was added in small portions to a solution of benzyl (5R)-5-(2-(benzyloxy)-2-oxoethyl)-3-(3-hydroxyphenyl)-4,5-dihydro-1,2-oxazole-5-carboxylate (126 g) in pyridine (380 mL) at 20 C. The obtained mixture was stirred at room temperature for 1.5 hours. To the reaction mixture, ethyl acetate (650 mL) and 1 M hydrochloric acid (1300 mL) were added at 0 C, and then, ethyl acetate (1300 mL) and water (260 mL) were added. The organic layer was separated, and the aqueous layer was subjected to extraction with ethyl acetate (1300 mL). Combined organic layers were washed with diluted aqueous ammonia ((28% aqueous ammonia (26 mL)/water (1300 mL))×2), 1 M hydrochloric acid (1300 mL×2), and brine (1300 mL) and dried over anhydrous sodium sulfate, and then, the solvent was distilled off under reduced pressure. The residue was washed with diisopropyl ether (1500 mL) to obtain the title compound (165 g).

MS: $[M+H]^+$ 595.3.

F) (5R)-3-(3-((4-Carbamimidamidobenzoyl)oxy) phenyl)-5-(carboxymethyl)-4,5-dihydro-1,2-oxazole-5-carboxylic acid A mixture of benzyl (5R)-5-(2-(benzyloxy)-2-oxoethyl)-3-(3-((4-nitrobenzoyl)oxy)phenyl)-4,5-dihydro-1,2-oxazole-5-carboxylate (77.5 g), 10% Pd/C (containing about 55% water, 7.8 g), and THF (780 mL) was stirred at room temperature for 3 hours under a hydrogen atmosphere. The catalyst was filtered off, and then, the filtrate was concentrated under reduced pressure to obtain (5R)-3-(3-((4-aminobenzoyl)oxy)phenyl)-5-(carboxymethyl)-4,5-dihydro-1,2-oxazole-5-carboxylic acid as a crude product.

This crude product was combined with a crude product of (5R)-3-(3-((4-aminobenzoyl)oxy)phenyl)-5-(carboxymethyl)-4,5-dihydro-1,2-oxazole-5-carboxylic acid obtained from benzyl (5R)-5-(2-(benzyloxy)-2-oxoethyl)-3-(3-((4-nitrobenzoyl)oxy)phenyl)-4,5-dihydro-1,2-oxazole-5-carboxylate (77.5 g) by the same operation as above, and mixed with cyanamide (40.7 g) and tert-butyl alcohol (2500 mL). To the obtained mixture, a 4 M hydrogen chloride/cyclopropyl methyl ether solution (242 mL) was added at room temperature. After stirring overnight at 50 C, the reaction mixture was concentrated under reduced pressure. A mixture of the obtained residue and water (350 mL) was added dropwise at room temperature to an aqueous solution prepared from ammonium acetate (74.6 g) and water (900 mL), then acetonitrile (130 mL) was added, and the obtained mixture was stirred at room temperature for 1 hour. The solid was collected by filtration and washed with acetonitrile (500 mL). Then, water (1000 ml) was added to the solid, and the obtained mixture was stirred at room temperature for 1 hour. The solid was collected by filtration and washed with water (1000 mL) and acetonitrile (500 mL) to obtain a crude product (111 g).

A mixture of the crude product (106.5 g) obtained by the above-mentioned method and acetic acid/water (9/1) (1600 mL) was heated to 70 C. The insoluble precipitate was filtered off, and the filtrate was cooled to 60 C, followed by dropwise addition of 2-butanone (1100 mL) at 60 C. The obtained suspension was stirred at 60 C for 1.5 hours, then 2-butanone (1020 mL) was added thereto, and the obtained mixture was cooled to 10 C and stirred at 10 C for 30 minutes. The solid was collected by filtration and washed with acetic acid/2-butanone (1/2) (530 mL) and 2-butanone (530 mL) to obtain crude crystals (72.1 g) of the title compound.

The crude crystals (30.0 g) of the title compound obtained by the above-mentioned method were dissolved in 1 M hydrochloric acid (900 mL) and purified by column chromatography (acetonitrile/1 M hydrochloric acid, subsequently acetonitrile/water) using a resin (HP20). Then, the obtained fraction was concentrated under reduced pressure, and a mixture of ammonium acetate (300 g) and water (600 mL) was added to the residue at room temperature. The solid was collected by filtration and washed with water (900 mL) and acetonitrile (300 mL) to obtain the title compound (28.8 g).

The title compound (126.8 g) obtained by repeating the above-mentioned method several times was suspended in water (3200 mL), and acetic acid (1000 mL) was added to the suspension at 60 C. The obtained mixture was heated to 85 C, and acetic acid (1040 mL) was added dropwise thereto at 85 C. The insoluble precipitate was filtered and washed with water/acetic acid (5/1) (720 mL). The filtrate was heated to 85 C, and acetic acid (60 mL) was added thereto. The obtained mixture was cooled to 70 C, stirred at 70 C for 1 hour, then gradually cooled to room temperature, and stirred overnight at room temperature. The solid was collected by filtration, washed with water/acetic acid (5/1) (480 mL), water (2600 mL), and acetone (3000 mL), and then dried under reduced pressure at 45 C for 1 hour to obtain the title compound (114 g).

$^1$H NMR (300 MHz, DMSO-$d_6$) delta 2.63-2.98 (2H, m), 3.17-3.45 (1H, m), 3.91 (1H, d, J=17.0 Hz), 7.28-7.47 (3H, m), 7.49-7.66 (3H, m), 7.72-8.28 (6H, m).

Optical purity: 99.6% ee

Eluted at a shorter retention time under the following optical analysis conditions.

Column: CHIROBIOTIC R (trade name) 4.6 mm ID×250 mm L Mobile phase: water/acetonitrile/tritylamine/acetic acid=900/100/1.25/3.75 (v/v/v/v)

Example 3

3-(5-((4-Carbamimidamidobenzoyl)oxy)-2-methylphenyl)-5-(carboxymethyl)-4,5-dihydro-1,2-oxazole-5-carboxylic acid trifluoroacetate

A) (E)-1-(5-(Benzyloxy)-2-methylphenyl)-N-hydroxymethanimine

A mixture of 5-(benzyloxy)-2-methylbenzaldehyde (15.9 g), hydroxyl ammonium chloride (5.37 g), sodium bicarbonate (6.49 g), and ethanol (150 mL) was stirred at room temperature for 6 hours. The precipitate was filtered off, and then, the filtrate was concentrated under reduced pressure. The residue was purified by silica gel column chromatography (ethyl acetate/hexane) to obtain the title compound (16.7 g).
MS: [M+H]$^+$ 242.1.

B) 5-(Benzyloxy)-N-hydroxy-2-methylbenzenecarboximidoyl chloride

N-Chlorosuccinimide (3.72 g) was added in small portions to a solution of (E)-1-(5-(benzyloxy)-2-methylphenyl)-N-hydroxymethanimine (6.40 g) in DMF (60 mL) at room temperature, and the obtained mixture was stirred at room temperature for 2 hours. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (6.05 g).
MS: [M+H]$^+$ 276.1.

C) Methyl 3-(5-(benzyloxy)-2-methylphenyl)-5-(2-methoxy-2-oxoethyl)-4,5-dihydro-1,2-oxazole-5-carboxylate Triethylamine (3.06 mL) was added to a mixture of 5-(benzyloxy)-N-hydroxy-2-methylbenzenecarboximidoyl chloride (6.05 g), dimethyl 2-methylenesuccinate (3.09 mL), and THF (100 mL) at room temperature, and the obtained mixture was stirred at 70 C for 2 hours. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (6.80 g).
MS: [M+H]$^+$ 398.1.

D) 3-(5-(Benzyloxy)-2-methylphenyl)-5-(carboxymethyl)-4,5-dihydro-1,2-oxazole-5-carboxylic acid A mixture of methyl 3-(5-(benzyloxy)-2-methylphenyl)-5-(2-methoxy-2-oxoethyl)-4,5-dihydro-1,2-oxazole-5-carboxylate (6.80 g), THF (70 mL), methanol (70 mL), and a 1 M aqueous sodium hydroxide solution (70 mL) was stirred at room temperature for 30 minutes. The reaction mixture was rendered acidic using 6 M hydrochloric acid at 0 C, followed by extraction with ethyl acetate. The extract was washed with water and saturated saline and dried over anhydrous magnesium sulfate, and then, the solvent was distilled off under reduced pressure to obtain the title compound (6.30 g).
MS: [M+H]$^+$ 370.1.

E) tert-Butyl 3-(5-(benzyloxy)-2-methylphenyl)-5-(2-tert-butoxy-2-oxoethyl)-4,5-dihydro-1,2-oxazole-5-carboxylate A mixture of 3-(5-(benzyloxy)-2-methylphenyl)-5-(carboxymethyl)-4,5-dihydro-1,2-oxazole-5-carboxylic acid (6.30 g), 1,1-di-tert-butoxy-N,N-dimethylmethanamine (27.7 g), and toluene (60 mL) was heated to reflux for 45 minutes. The reaction mixture was concentrated under reduced pressure, and then, the residue was purified by silica gel column chromatography (ethyl acetate/hexane, subsequently methanol/ethyl acetate) to obtain the title compound (3.93 g).
MS: [M+Na]$^+$ 504.2.

F) tert-Butyl 5-(2-tert-butoxy-2-oxoethyl)-3-(5-hydroxy-2-methylphenyl)-4,5-dihydro-1,2-oxazole-5-carboxylate A mixture of tert-butyl 3-(5-(benzyloxy)-2-methylphenyl)-5-(2-tert-butoxy-2-oxoethyl)-4,5-dihydro-1,2-oxazole-5-carboxylate (3.93 g), 10% Pd/C (containing about 55% water, 400 mg), and methanol (40 mL) was stirred at room temperature for 75 minutes in a hydrogen atmosphere. The catalyst was filtered off, and then, the filtrate was concentrated under reduced pressure. The residue was purified by silica gel column chromatography (ethyl acetate/hexane) to obtain the title compound (2.29 g).
MS: [M+Na]$^+$ 414.2.

G) tert-Butyl 5-(2-tert-butoxy-2-oxoethyl)-3-(5-((4-carbamimidamidobenzoyl)oxy)-2-methylphenyl)-4,5-dihydro-1,2-oxazole-5-carboxylate 4-Carbamimidamidobenzoyl chloride hydrochloride (173 mg) was added to a mixture of tert-butyl 5-(2-tert-butoxy-2-oxoethyl)-3-(5-hydroxy-2-methylphenyl)-4,5-dihydro-1,2-oxazole-5-carboxylate (290 mg), pyridine (1 mL), and NMP (3 mL) at 50 C, and the obtained mixture was stirred at 50 C for 20 minutes. Further, 4-carbamimidamidobenzoyl chloride hydrochloride (173 mg) was added thereto, and the obtained mixture was stirred at 50 C for 20 minutes. Further, 4-carbamimidamidobenzoyl chloride hydrochloride (173 mg) was added thereto, and the obtained mixture was stirred at 50 C for 3 hours. Further, 4-carbamimidamidobenzoyl chloride hydrochloride (173 mg) was added thereto, and the obtained mixture was stirred overnight at 50 C. The reaction mixture was purified by silica gel column chromatography (NH, ethyl acetate/hexane, subsequently methanol/ethyl acetate) and then further fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (210 mg).
MS: [M+H]$^+$ 553.3.

H) 3-(5-((4-Carbamimidamidobenzoyl)oxy)-2-methylphenyl)-5-(carboxymethyl)-4,5-dihydro-1,2-oxazole-5-carboxylic acid trifluoroacetate A mixture of tert-butyl 5-(2-tert-butoxy-2-oxoethyl)-3-(5-((4-carbamimidamidobenzoyl)oxy)-2-methylphenyl)-4,5-dihydro-1,2-oxazole-5-carboxylate (210 mg) and TFA (3 mL) was stirred at room temperature for 1 hour. The reaction mixture was concentrated under reduced pressure, and then, the residue was washed with diethyl ether to obtain the title compound (146 mg).

$^1$H NMR (400 MHz, DMSO-$d_6$) delta 2.42-2.60 (3H, m), 3.01 (2H, s), 3.62 (1H, d, J=17.1 Hz), 3.91 (1H, d, J=17.6 Hz), 7.20-7.34 (1H, m), 7.36-7.59 (4H, m), 7.80 (4H, brs), 8.17 (2H, d, J=8.2 Hz), 10.21 (1H, brs), 12.57 (1H, brs), 13.27 (1H, brs).

Example 5

(5S)-3-(3-((4-Carbamimidamidobenzoyl)oxy)phenyl)-5-(carboxymethyl)-4,5-dihydro-1,2-oxazole-5-carboxylic acid A) tert-Butyl 3-(3-(benzyloxy)phenyl)-5-(2-tert-butoxy-2-oxoethyl)-4,5-dihydro-1,2-oxazole-5-carboxylate 1,1-Di-tert-butoxy-N,N-dimethylmethanamine (49.9 mL) was added dropwise to a mixture of 3-(3-(benzyloxy)phenyl)-5-(carboxymethyl)-4,5-dihydro-1,2-oxazole-5-carboxylic acid (14.8 g) and toluene (150 mL) at 110 C, and the obtained mixture was heated to reflux for 30 minutes. Further, 1,1-di-tert-butoxy-N,N-dimethylmethanamine (12.48 mL) was added thereto, and the obtained mixture was heated to reflux for 30 minutes. The reaction mixture was concentrated under reduced pressure, and then, the residue was purified by silica gel column chromatography (ethyl acetate/hexane) to obtain the title compound (16.2 g).

MS: [M+Na]$^+$ 490.2.

B) tert-Butyl 5-(2-tert-butoxy-2-oxoethyl)-3-(3-hydroxyphenyl)-4,5-dihydro-1,2-oxazole-5-carboxylate A mixture of tert-butyl 3-(3-(benzyloxy)phenyl)-5-(2-tert-butoxy-2-oxoethyl)-4,5-dihydro-1,2-oxazole-5-carboxylate (58.4 g), 10% Pd/C (containing about 55% water, 5.8 g), and methanol (500 mL) was stirred at room temperature for 45 minutes under a hydrogen atmosphere. The catalyst was filtered off, and then, the filtrate was concentrated under reduced pressure. The obtained residue was purified by silica gel column chromatography (ethyl acetate/hexane) to obtain the title compound (34.5 g).

MS: [M+Na]$^+$ 400.2.

C) tert-Butyl (5S)-5-(2-tert-butoxy-2-oxoethyl)-3-(3-hydroxyphenyl)-4,5-dihydro-1,2-oxazole-5-carboxylate A racemate of tert-butyl 5-(2-tert-butoxy-2-oxoethyl)-3-(3-hydroxyphenyl)-4,5-dihydro-1,2-oxazole-5-carboxylate (49.5 g) was fractionated by HPLC (column: CHIRALPAK AD (trade name), 50 mm ID×500 mm L, mobile phase: hexane/ethanol=850/150) to obtain the title compound (24.3 g) eluted at a larger retention time.

MS: [M+Na]$^+$ 400.2.

Optical purity: >99.9% ee

Eluted at a longer retention time under the following optical analysis conditions.

Column: CHIRALPAK AD (trade name) 4.6 mm ID×250 mm L

Mobile phase: hexane/ethanol=850/150 (v/v)

D) tert-Butyl (5S)-5-(2-tert-butoxy-2-oxoethyl)-3-(3-((4-carbamimidamidobenzoyl)oxy)phenyl)-4,5-dihydro-1,2-oxazole-5-carboxylate 4-Carbamimidamidobenzoyl chloride hydrochloride (2.158 g) was added to a mixture of tert-butyl (5S)-5-(2-tert-butoxy-2-oxoethyl)-3-(3-hydroxyphenyl)-4,5-dihydro-1,2-oxazole-5-carboxylate (1.74 g), pyridine (2.2 mL), and DMA (2.2 mL) at 50 C, and the obtained mixture was stirred at 50 C for 3 hours. Further, 4-carbamimidamidobenzoyl chloride hydrochloride (2.158 g), DMA (1.1 mL), and pyridine (1.1 mL) were added thereto, and the obtained mixture was stirred at 50 C for 2 hours. To the reaction mixture, water was added, followed by extraction with ethyl acetate and ethyl acetate/THF (1/1). The extract was washed with brine and dried over anhydrous magnesium sulfate, and then, the solvent was distilled off under reduced pressure. The residue was purified by silica gel column chromatography (ethyl acetate, subsequently acetonitrile/acetic acid), and then, the obtained fraction was concentrated under reduced pressure. The residue was added to a saturated aqueous solution of sodium bicarbonate, followed by extraction with ethyl acetate. The extract was dried over anhydrous magnesium sulfate, and the solvent was distilled off under reduced pressure to obtain the title compound (1.40 g).

MS: [M+H]$^+$ 539.3.

E) (5S)-3-(3-((4-Carbamimidamidobenzoyl)oxy)phenyl)-5-(carboxymethyl)-4,5-dihydro-1,2-oxazole-5-carboxylic acid trifluoroacetate A mixture of tert-butyl (5S)-5-(2-tert-butoxy-2-oxoethyl)-3-(3-((4-carbamimidamidobenzoyl)oxy)phenyl)-4,5-dihydro-1,2-oxazole-5-carboxylate (3.29 g) and TFA (30 mL) was stirred at room temperature for 2 hours. The reaction mixture was concentrated under reduced pressure, and then, the residue was washed with diethyl ether to obtain the title compound (3.01 g).

MS: [M+H]$^+$ 427.1.

F) (5S)-3-(3-((4-Carbamimidamidobenzoyl)oxy)phenyl)-5-(carboxymethyl)-4,5-dihydro-1,2-oxazole-5-carboxylic acid (5S)-3-(3-((4-Carbamimidamidobenzoyl)oxy)phenyl)-5-(carboxymethyl)-4,5-dihydro-1,2-oxazole-5-carboxylic acid trifluoroacetate (4.27 g) was suspended in water (126 mL), and the obtained suspension was heated to 80 C and then sonicated at room temperature. To the obtained mixture, diethyl ether (84 mL) was added, and the mixture was stirred overnight at room temperature. The precipitate was collected by filtration and washed with water (1 mL) to obtain the title compound (2.69 g).

$^1$H NMR (400 MHz, DMSO-$d_6$) delta 2.66-2.97 (2H, m), 3.22-3.38 (1H, m), 3.91 (1H, d, J=17.2 Hz), 7.14-11.06 (12H, m).

Optical purity: >99% ee

Eluted at a longer retention time under the following optical analysis conditions.

Column: CHIROBIOTIC R (trade name) 4.6 mm ID×250 mm L Mobile phase: water/acetonitrile/tritylamine/acetic acid=900/100/1/1 (v/v/v/v)

Example 6

2,2'-(3-(3-((4-Carbamimidamidobenzoyl)oxy)phenyl)-4,5-dihydro-1,2-oxazole-5,5-diyl)diacetic acid A) 3-(3-(Benzyloxy)phenyl)-5-(2-butoxy-2-oxoethyl)-4,5-dihydro-1,2-oxazole-5-carboxylic acid A mixture of (E)-1-(3-(benzyloxy)phenyl)-N-hydroxymethanimine (9.85 g), N-chlorosuccinimide (6.08 g), and DMF (100 mL) was stirred at room temperature for 4 hours. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane), and the obtained 3-(benzyloxy)-N-hydroxybenzene carboximidoyl chloride (10.0 g, containing impurities) was combined with 4-butoxy-2-methylene-4-oxobutanoic acid (4.27 g) and THF (100 mL). To the obtained mixture, triethylamine (7.99 mL) was added at room temperature. The mixture was stirred overnight at 70 C, and then, 1 M hydrochloric acid was added thereto, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) and then suspended in diethyl ether and hexane, and the solvent was distilled off under reduced pressure. The obtained residue was washed with hexane to obtain the title compound (4.92 g).

MS: [M+H]$^+$ 412.2.

B) Butyl (3-(3-(benzyloxy)phenyl)-5-(diazoacetyl)-4,5-dihydro-1,2-oxazol-5-yl)acetate Oxalyl dichloride (2.86 mL) and DMF (3 drops) were added to a mixture of 3-(3-(benzyloxy)phenyl)-5-(2-butoxy-2-oxoethyl)-4,5-dihydro-1,2-oxazole-5-carboxylic acid (4.50 g) and THF (50 mL). The obtained mixture was stirred at room temperature for 2 hours, and then, the solvent was distilled off under reduced pressure. A mixture of the obtained residue and THF (50 mL) was added to a mixture of (diazomethyl)trimethylsilane (0.6 M hexane solution, 1.823 mL), triethylamine (1.829 mL), and acetonitrile (50 mL) at 0 C. The obtained mixture was stirred at 0 C for 2 hours, and then, the solvent was distilled off under reduced pressure. Ethyl acetate and water were added to the residue, and the obtained mixture was subjected to extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (2.14 g).

MS: [M+Na]$^+$ 458.2.

C) Butyl methyl 2,2'-(3-(3-(benzyloxy)phenyl)-4,5-dihydro-1,2-oxazole-5,5-diyl)diacetate Silver benzoate (0.393 g) was added to a mixture of butyl (3-(3-(benzyloxy)phenyl)-5-(diazoacetyl)-4,5-dihydro-1,2-oxazol-5-yl)acetate (1.87 g), triethylamine (1.496 mL), methanol (40 mL), and THF (20 mL) at 50 C, and the obtained mixture was stirred at 50 C for 20 minutes. The precipitate was filtered off, and then, the filtrate was concentrated under reduced pressure. The residue was purified by silica gel column chromatography (ethyl acetate/hexane) to obtain the title compound (0.919 g).

MS: [M+H]$^+$ 440.2.

D) 2,2'-(3-(3-(Benzyloxy)phenyl)-4,5-dihydro-1,2-oxazole-5,5-diyl)diacetic acid A mixture of butyl methyl 2,2'-(3-(3-(benzyloxy)phenyl)-4,5-dihydro-1,2-oxazole-5,5-diyl)diacetate (1.02 g), THF (15 mL), methanol (15 mL), and a 1 M aqueous sodium hydroxide solution (15 mL) was stirred overnight at room temperature. The reaction mixture was neutralized with 1 M hydrochloric acid at 0 C, followed by extraction with ethyl acetate. The extract was washed with brine and dried over anhydrous magnesium sulfate, and then, the solvent was distilled off under reduced pressure to obtain the title compound (0.786 g).

MS: [M+H]$^+$ 370.1.

E) Di-tert-butyl 2,2'-(3-(3-(benzyloxy)phenyl)-4,5-dihydro-1,2-oxazole-5,5-diyl)diacetate A mixture of 2,2'-(3-(3-(benzyloxy)phenyl)-4,5-dihydro-1,2-oxazole-5,5-diyl)diacetic acid (786 mg), 1,1-di-tert-butoxy-N,N-dimethylmethanamine (4327 mg), and toluene (10 mL) was heated to reflux for 30 minutes. Further, 1,1-di-tert-butoxy-N,N-dimethylmethanamine (865 mg) was added thereto, and the obtained mixture was heated to reflux for 30 minutes. The reaction mixture was concentrated under reduced pressure, and then, the residue was purified by silica gel column chromatography (ethyl acetate/hexane) to obtain the title compound (765 mg).

MS: [M+Na]$^+$ 504.2.

F) Di-tert-butyl 2,2'-(3-(3-hydroxyphenyl)-4,5-dihydro-1,2-oxazole-5,5-diyl)diacetate A mixture of di-tert-butyl 2,2'-(3-(3-(benzyloxy)phenyl)-4,5-dihydro-1,2-oxazole-5,5-diyl)diacetate (765 mg), a palladium carbon-ethylenediamine complex (38 mg), THF (10 mL), and methanol (10 mL) was stirred at room temperature for 30 hours under a hydrogen atmosphere. The catalyst was filtered off, and then, the filtrate was concentrated under reduced pressure. The residue was purified by silica gel column chromatography (ethyl acetate/hexane) to obtain the title compound (611 mg).

MS: [M+Na]$^+$ 414.2.

G) 3-(5,5-Bis(2-tert-butoxy-2-oxoethyl)-4,5-dihydro-1,2-oxazol-3-yl)phenyl 4-carbamimidamidobenzoate 4-Carbamimidamidobenzoyl chloride hydrochloride (317 mg) was added to a mixture of di-tert-butyl 2,2'-(3-(3-hydroxyphenyl)-4,5-dihydro-1,2-oxazole-5,5-diyl)diacetate (265 mg), pyridine (0.3 mL), and NMP (0.3 mL) at 50 C, and the obtained mixture was stirred overnight at 50 C. To the reaction mixture, acetonitrile was added. The precipitate was filtered off, and then, the filtrate was concentrated under reduced pressure. The residue was purified by silica gel column chromatography (ethyl acetate, subsequently acetonitrile/acetic acid) and then further fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (94 mg).

MS: [M+H]$^+$ 553.3.

H) 2,2'-(3-(3-((4-Carbamimidamidobenzoyl)oxy)phenyl)-4,5-dihydro-1,2-oxazole-5,5-diyl)diacetic acid trifluoroacetate A mixture of 3-(5,5-bis(2-tert-butoxy-2-oxoethyl)-4,5-dihydro-1,2-oxazol-3-yl)phenyl 4-carbamimidamidobenzoate (94.1 mg) and TFA (1 mL) was stirred at room temperature for 2 hours. The reaction mixture was concentrated under reduced pressure, and then, the residue was washed with diethyl ether to obtain the title compound (63.3 mg).
MS: [M+H]$^+$ 441.1.

I) 2,2'-(3-(3-((4-Carbamimidamidobenzoyl)oxy) phenyl)-4,5-dihydro-1,2-oxazole-5,5-diyl)diacetic acid 2,2'-(3-(3-((4-Carbamimidamidobenzoyl)oxy)phenyl)-4,5-dihydro-1,2-oxazole-5,5-diyl)diacetic acid trifluoroacetate (40.9 mg) was suspended in water (1 mL), and an aqueous solution prepared from ammonium acetate (17.06 mg) and water (1 mL) was added to the suspension at room temperature. The obtained mixture was stirred at room temperature for 1 hour, and then, the solid was collected by filtration and washed with water and acetone to obtain the title compound (28.4 mg).
$^1$H NMR (400 MHz, DMSO-d$_6$) delta 2.60 (2H, d, J=13.8 Hz), 2.73 (2H, d, J=13.8 Hz), 3.47 (2H, s), 7.27-7.40 (3H, m), 7.50-7.64 (3H, m), 7.87 (4H, brs), 8.07 (2H, d, J=8.5 Hz).

Example 7

4-(4-(2-(5,5-Bis(carboxymethyl)-4,5-dihydro-1,2-oxazol-3-yl)-4-((4-carbamimidamidobenzoyl)oxy) phenyl)piperidin-1-yl)-4-oxobutanoic acid trifluoroacetate A) (E)-1-(5-(Benzyloxy)-2-bromophenyl)-N-hydroxymethanimine A mixture of 5-(benzyloxy)-2-bromobenzaldehyde (29.5 g), hydroxyl ammonium chloride (7.75 g), sodium bicarbonate (9.36 g), water (30 mL), and ethanol (270 mL) was stirred overnight at room temperature. To the reaction mixture, water (150 mL) was added, and the mixture was concentrated into half the volume under reduced pressure. Then, the residue was subjected to extraction with ethyl acetate. The extract was washed with brine and dried over anhydrous magnesium sulfate, and then, the solvent was distilled off under reduced pressure. The residue was washed with hexane to obtain the title compound (27.2 g)
$^1$H NMR (400 MHz, DMSO-d$_6$) delta 5.14 (2H, s), 7.04 (1H, d, J=8.8 Hz), 7.24-7.62 (7H, m), 8.26 (1H, s), 11.69 (1H, s).

B) 3-(5-(Benzyloxy)-2-bromophenyl)-5-(2-methoxy-2-oxoethyl)-4,5-dihydro-1,2-oxazole-5-carboxylic acid An aqueous sodium hypochlorite solution (5%, 146 g) was added to a mixture of (E)-1-(5-(benzyloxy)-2-bromophenyl)-N-hydroxymethanimine (27.2 g), 4-methoxy-2-methylene-4-oxobutanoic acid (12.8 g), and THF (270 mL) at 0 C. The obtained mixture was stirred at 0 C for 1 hour and at room temperature overnight. To the reaction mixture, 1 M hydrochloric acid was added, followed by extraction with ethyl acetate. The extract was washed with bline and dried over anhydrous magnesium sulfate, and then, the solvent was distilled off under reduced pressure. The residue was purified by silica gel column chromatography (ethyl acetate/hexane), and then, the obtained residue was washed with hexane/diethyl ether to obtain the title compound (26.4 g).

$^1$H NMR (400 MHz, DMSO-d$_6$) delta 2.94-3.20 (2H, m), 3.50-3.73 (4H, m), 3.95 (1H, d, J=17.6 Hz), 5.15 (2H, s), 7.08 (1H, dd, J=8.8, 2.9 Hz), 7.23 (1H, d, J=3.0 Hz), 7.29-7.52 (5H, m), 7.63 (1H, d, J=8.9 Hz), 13.45 (1H, brs).

C) Methyl (3-(5-(benzyloxy)-2-bromophenyl)-5-(diazoacetyl)-4,5-dihydro-1,2-oxazol-5-yl)acetate Oxalyl dichloride (15.41 mL) was added dropwise to a solution of 3-(5-(benzyloxy)-2-bromophenyl)-5-(2-methoxy-2-oxoethyl)-4,5-dihydro-1,2-oxazole-5-carboxylic acid (26.4 g) in THF (270 mL) at 0 C. The obtained mixture was warmed to room temperature. DMF (3 drops) was added thereto, and the mixture was stirred at room temperature for 4 hours and then concentrated under reduced pressure. A mixture of the obtained residue and THF (150 mL) was added to a mixture of (diazomethyl)trimethylsilane (2 M hexane solution, 35.3 mL), triethylamine (24.63 mL), and THF (150 mL) at 0 C. The obtained mixture was stirred at 0 C for 1.5 hours, and then, water was added thereto, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (20.4 g).
$^1$H NMR (400 MHz, DMSO-d$_6$) delta 3.00 (1H, d, J=16.4 Hz), 3.20 (1H, d, J=16.4 Hz), 3.61 (3H, s), 3.64-3.81 (2H, m), 5.14 (2H, s), 6.33 (1H, brs), 7.09 (1H, dd, J=8.8, 2.8 Hz), 7.24 (1H, d, J=2.8 Hz), 7.31-7.50 (5H, m), 7.63 (1H, d, J=8.9 Hz).

D) Dimethyl 2,2'-(3-(5-(benzyloxy)-2-bromophenyl)-4,5-dihydro-1,2-oxazole-5,5-diyl)diacetate Silver benzoate (3.90 g) was added to a mixture of methyl (3-(5-(benzyloxy)-2-bromophenyl)-5-(diazoacetyl)-4,5-dihydro-1,2-oxazol-5-yl)acetate (20.1 g), triethylamine (14.83 mL), and methanol (200 mL) at 40 C, and the obtained mixture was stirred at 40 C for 1.5 hours. The precipitate was filtered off, and then, the filtrate was concentrated under reduced pressure. The residue was purified by silica gel column chromatography (ethyl acetate/hexane) to obtain the title compound (12.0 g).
$^1$H NMR (400 MHz, DMSO-d$_6$) delta 2.89-3.07 (4H, m), 3.53-3.66 (8H, m), 5.14 (2H, s), 7.02-7.25 (2H, m), 7.31-7.51 (5H, m), 7.62 (1H, d, J=8.7 Hz).

E) 2,2'-(3-(5-(Benzyloxy)-2-bromophenyl)-4,5-dihydro-1,2-oxazole-5,5-diyl)diacetic acid A mixture of dimethyl 2,2'-(3-(5-(benzyloxy)-2-bromophenyl)-4,5-dihydro-1,2-oxazole-5,5-diyl)diacetate (12.0 g), THF (120 mL), methanol (120 mL), and a 1 M aqueous sodium hydroxide solution (120 mL) was stirred at room temperature for 3 hours. The reaction mixture was rendered acidic using 6 M hydrochloric acid at 0 C, and brine was added thereto, followed by extraction with ethyl acetate. The extract was washed with water and saturated saline and dried over anhydrous magnesium sulfate, and then, the solvent was distilled off under reduced pressure to obtain the title compound (9.75 g).
$^1$H NMR (400 MHz, DMSO-d$_6$) delta 2.70-3.04 (4H, m), 3.54 (2H, s), 5.14 (2H, s), 7.06 (1H, d, J=8.9 Hz), 7.19 (1H, brs), 7.31-7.48 (5H, m), 7.61 (1H, d, J=8.9 Hz), 12.60 (2H, brs).

F) Di-tert-butyl 2,2'-(3-(5-(benzyloxy)-2-bromophenyl)-4,5-dihydro-1,2-oxazole-5,5-diyl)diacetate 1,1-Di-tert-butoxy-N,N-dimethylmethanamine (22.11 g) was added dropwise to a mixture of 2,2'-(3-(5-(benzyloxy)-2-bromophenyl)-4,5-dihydro-1,2-oxazole-5,5-diyl)diacetic acid (9.75 g) and toluene (100 mL) at 100 C, and the obtained mixture was stirred at 100 C for 30 minutes. Further, 1,1-di-tert-butoxy-N,N-dimethylmethanamine (5.53 g) was added thereto, and the obtained mixture was stirred at 100 C for 30 minutes. Further, 1,1-di-tert-butoxy-N,N-dimethylmethanamine (2.211 g) was added thereto, and the obtained mixture was stirred at 100 C for 30 minutes. The reaction mixture was concentrated under reduced pressure, and then, the residue was purified by silica gel column chromatography (ethyl acetate/hexane). The obtained residue was washed with hexane to obtain the title compound (5.73 g).

$^1$H NMR (400 MHz, DMSO-$d_6$) delta 1.40 (18H, s), 2.77-2.90 (4H, m), 3.57 (2H, s), 5.14 (2H, s), 7.01-7.11 (1H, m), 7.20 (1H, brs), 7.31-7.49 (5H, m), 7.62 (1H, d, J=9.3 Hz).

G) tert-Butyl 4-oxo-4-(4-(4,4,5,5-tetramethyl-1,3,2-dioxaborolan-2-yl)-3,6-dihydropyridin-1(2H)-yl)butanoate HATU (3.68 g) was added to a mixture of 4-(4,4,5,5-tetramethyl-1,3,2-dioxaborolan-2-yl)-1,2,3,6-tetrahydropyridine hydrochloride (1.98 g), 4-tert-butoxy-4-oxobutanoic acid (1.686 g), N,N-diisopropylethylamine (3.38 mL), and DMF (20 mL) at 0 C, and the obtained mixture was stirred at room temperature for 3 days. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (NH, ethyl acetate/hexane) to obtain the title compound (1.84 g).

MS: [M+H]$^+$ 366.3.

H) tert-Butyl 4-(4-(4-(benzyloxy)-2-(5,5-bis(2-tert-butoxy-2-oxoethyl)-4,5-dihydro-1,2-oxazol-3-yl)phenyl)-3,6-dihydropyridin-1(2H)-yl)-4-oxobutanoate A mixture of di-tert-butyl 2,2'-(3-(5-(benzyloxy)-2-bromophenyl)-4,5-dihydro-1,2-oxazole-5,5-diyl)diacetate (65.4 mg), tert-butyl 4-oxo-4-(4-(4,4,5,5-tetramethyl-1,3,2-dioxaborolan-2-yl)-3,6-dihydropyridin-1(2H)-yl)butanoate (107 mg), [1,1'-bis(diphenylphosphino)ferrocene]palladium(II) dichloride (8.54 mg), a 2 M aqueous cesium carbonate solution (0.3 mL), and DME (1.2 mL) was stirred at 90 C for 1 hour under microwave irradiation in an argon atmosphere. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (52.1 mg).

MS: [M+H]$^+$ 719.5.

I) tert-Butyl 4-(4-(2-(5,5-bis(2-tert-butoxy-2-oxoethyl)-4,5-dihydro-1,2-oxazol-3-yl)-4-hydroxyphenyl)piperidin-1-yl)-4-oxobutanoate A mixture of tert-butyl 4-(4-(4-(benzyloxy)-2-(5,5-bis(2-tert-butoxy-2-oxoethyl)-4,5-dihydro-1,2-oxazol-3-yl)phenyl)-3,6-dihydropyridin-1(2H)-yl)-4-oxobutanoate (52.1 mg), 10% Pd/C (containing about 55% water, 20 mg), and THF (1 mL) was stirred at room temperature for 6 hours in a hydrogen atmosphere. The catalyst was filtered off, and then, the filtrate was concentrated under reduced pressure. The residue was purified by silica gel column chromatography (ethyl acetate/hexane) to obtain the title compound (35.0 mg).

MS: [M+H]$^+$ 631.4.

J) 3-(5,5-Bis(2-tert-butoxy-2-oxoethyl)-4,5-dihydro-1,2-oxazol-3-yl)-4-(1-(4-tert-butoxy-4-oxobutanoyl)piperidin-4-yl)phenyl 4-carbamimidamidobenzoate 4-Carbamimidamidobenzoyl chloride hydrochloride (12.99 mg) was added to a mixture of tert-butyl 4-(4-(2-(5,5-bis(2-tert-butoxy-2-oxoethyl)-4,5-dihydro-1,2-oxazol-3-yl)-4-hydroxyphenyl)piperidin-1-yl)-4-oxobutanoate (35.0 mg), pyridine (0.1 mL), and NMP (0.1 mL) at 50 C, and the obtained mixture was stirred at 50 C for 10 minutes. Further, 4-carbamimidamidobenzoyl chloride hydrochloride (12.99 mg) was added thereto, and the obtained mixture was stirred at 50 C for 10 minutes. Further, 4-carbamimidamidobenzoyl chloride hydrochloride (12.99 mg) was added thereto, and the obtained mixture was stirred at 50 C for 10 minutes. Further, 4-carbamimidamidobenzoyl chloride hydrochloride (12.99 mg) was added thereto, and the obtained mixture was stirred at 50 C for 10 minutes. Further, 4-carbamimidamidobenzoyl chloride hydrochloride (12.99 mg) was added thereto, and the obtained mixture was stirred overnight at 50 C. To the reaction mixture, acetonitrile was added, and the obtained mixture was purified by silica gel column chromatography (NH, ethyl acetate/hexane, subsequently methanol/ethyl acetate) to obtain the title compound (29.2 mg).

MS: [M+H]$^+$ 792.5.

K) 4-(4-(2-(5,5-Bis(carboxymethyl)-4,5-dihydro-1,2-oxazol-3-yl)-4-((4-carbamimidamidobenzoyl)oxy)phenyl)piperidin-1-yl)-4-oxobutanoic acid trifluoroacetate A mixture of 3-(5,5-bis(2-tert-butoxy-2-oxoethyl)-4,5-dihydro-1,2-oxazol-3-yl)-4-(1-(4-tert-butoxy-4-oxobutanoyl)piperidin-4-yl)phenyl 4-carbamimidamidobenzoate (29.2 mg) and TFA (1 mL) was stirred at room temperature for 2 hours. The reaction mixture was concentrated under reduced pressure, and then, the residue was washed with diethyl ether to obtain the title compound (25.4 mg).

$^1$H NMR (400 MHz, DMSO-$d_6$) delta 1.40-1.85 (4H, m), 2.35-2.63 (6H, m), 2.77-2.98 (4H, m), 3.01-3.18 (1H, m), 3.57 (2H, s), 3.90-4.11 (1H, m), 4.44-4.62 (1H, m), 7.26-7.38 (2H, m), 7.40-7.54 (3H, m), 7.76 (4H, brs), 8.16 (2H, d, J=8.7 Hz), 10.11 (1H, brs), 12.37 (3H, brs).

Example 8

3-(5-((4-Carbamimidamidobenzoyl)oxy)-2-cyclohexylphenyl)-5-(carboxymethyl)-4,5-dihydro-1,2-oxazole-5-carboxylic acid trifluoroacetate

A) Di-tert-butyl 2-methylenesuccinate

2-Methylprop-1-ene (50.3 mL) was added to 2-methylenesuccinic acid (10.0 g) at −78 C, then sulfuric acid (0.819 mL) was added dropwise at −78 C, and then, the obtained mixture was stirred at room temperature at 4.5 to 3.5 atm for 22 hours in a sealed tube. After removal of 2-methylprop- 1-ene at room temperature, the reaction mixture was diluted with ethyl acetate (100 mL) and added to a saturated aqueous solution of sodium bicarbonate (100 mL) at 0 C, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (12.8 g).

$^1$H NMR (400 MHz, DMSO-$d_6$) delta 1.39 (9H, s), 1.42 (9H, s), 3.20 (2H, s), 5.66 (1H, d, J=1.3 Hz), 6.06 (1H, d, J=1.5 Hz).

B) tert-Butyl 3-(5-(benzyloxy)-2-bromophenyl)-5-(2-tert-butoxy-2-oxoethyl)-4,5-dihydro-1,2-oxazole-5-carboxylate An aqueous sodium hypochlorite solution (5%, 16.42 g) was added dropwise to a solution of (E)-1-(5-(benzyloxy)-2-bromophenyl)-N-hydroxymethanimine (3.07 g) and di-tert-butyl 2-methylenesuccinate (2.43 g) in THF (30 mL) at 0 C, and the obtained mixture was stirred at 0 C for 2 hours. The reaction mixture was diluted with ethyl acetate, and 1 M hydrochloric acid was added thereto. The organic layer was washed with brine and dried over anhydrous magnesium sulfate, and then, the solvent was distilled off under reduced pressure. The residue was purified by silica gel column chromatography (ethyl acetate/hexane) to obtain the title compound (4.50 g).

$^1$H NMR (400 MHz, DMSO-$d_6$) delta 1.40 (9H, s), 1.44 (9H, s), 2.84-3.08 (2H, m), 3.56 (1H, d, J=17.8 Hz), 3.94 (1H, d, J=17.8 Hz), 5.15 (2H, s), 7.08 (1H, dd, J=8.9, 3.1 Hz), 7.22 (1H, d, J=3.1 Hz), 7.27-7.50 (5H, m), 7.63 (1H, d, J=8.8 Hz).

C) tert-Butyl 3-(5-(benzyloxy)-2-(cyclohex-1-en-1-yl)phenyl)-5-(2-tert-butoxy-2-oxoethyl)-4,5-dihydro-1,2-oxazole-5-carboxylate A mixture of tert-butyl 3-(5-(benzyloxy)-2-bromophenyl)-5-(2-tert-butoxy-2-oxoethyl)-4,5-dihydro-1,2-oxazole-5-carboxylate (200 mg), 2-(cyclohex-1-en-1-yl)-4,4,5,5-tetramethyl-1,3,2-dioxaborolane (114 mg), [1,1'-bis(diphenylphosphino)ferrocene]palladium(II) dichloride (26.8 mg), a 2 M aqueous cesium carbonate solution (0.366 mL), and DME (2 mL) was stirred overnight at 90 C in a nitrogen atmosphere. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (118 mg).

MS: [M+H]$^+$ 548.3.

D) tert-Butyl 5-(2-tert-butoxy-2-oxoethyl)-3-(2-cyclohexyl-5-hydroxyphenyl)-4,5-dihydro-1,2-oxazole-5-carboxylate A mixture of tert-butyl 3-(5-(benzyloxy)-2-(cyclohex-1-en-1-yl)phenyl)-5-(2-tert-butoxy-2-oxoethyl)-4,5-dihydro-1,2-oxazole-5-carboxylate (118 mg), 10% Pd/C (containing about 55% water, 15 mg), and THF (2 mL) was stirred overnight at room temperature under a hydrogen atmosphere. The catalyst was filtered off, and then, the filtrate was concentrated under reduced pressure. The residue was purified by silica gel column chromatography (ethyl acetate/hexane) to obtain the title compound (54.1 mg).

MS: [M+Na]$^+$ 482.2.

E) tert-Butyl 5-(2-tert-butoxy-2-oxoethyl)-3-(5-((4-carbamimidamidobenzoyl)oxy)-2-cyclohexylphenyl)-4,5-dihydro-1,2-oxazole-5-carboxylate 4-Carbamimidamidobenzoyl chloride hydrochloride (55.1 mg) was added to a mixture of tert-butyl 5-(2-tert-butoxy-2-oxoethyl)-3-(2-cyclohexyl-5-hydroxyphenyl)-4,5-dihydro-1,2-oxazole-5-carboxylate (54.1 mg), pyridine (0.06 mL), and NMP (0.06 mL) at 50 C, and the obtained mixture was stirred at 50 C for 5 days. The reaction mixture was fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (12.7 mg).

MS: [M+H]$^+$ 621.4.

F) 3-(5-((4-Carbamimidamidobenzoyl)oxy)-2-cyclohexylphenyl)-5-(carboxymethyl)-4,5-dihydro-1,2-oxazole-5-carboxylic acid trifluoroacetate A mixture of tert-butyl 5-(2-tert-butoxy-2-oxoethyl)-3-(5-((4-carbamimidamidobenzoyl)oxy)-2-cyclohexylphenyl)-4,5-dihydro-1,2-oxazole-5-carboxylate (12.7 mg) and TFA (1 mL) was stirred at room temperature for 2 hours. The reaction mixture was concentrated under reduced pressure, and then, the residue was washed with diethyl ether to obtain the title compound (5.8 mg).

$^1$H NMR (400 MHz, DMSO-$d_6$) delta 1.17-1.96 (10H, m), 2.73-3.21 (4H, m), 3.87 (1H, d, J=16.7 Hz), 7.25-7.55 (5H, m), 7.72 (4H, brs), 8.16 (2H, d, J=8.4 Hz), 10.09 (1H, brs).

Example 11

3-(3-((4-Carbamimidamidobenzoyl)oxy)-5-methylphenyl)-5-(carboxymethyl)-4,5-dihydro-1,2-oxazole-5-carboxylic acid trifluoroacetate A) (3-(Benzyloxy)-5-methylphenyl)methanol A solution of methyl 3-(benzyloxy)-5-methylbenzoate (1.29 g) in THF (10 mL) was added dropwise to a suspension of lithium aluminum hydride (0.229 g) in THF (10 mL) at 0 C. The obtained mixture was stirred at 0 C for 2 hours, then sodium sulfate decahydrate was added thereto in small portions at 0 C, and the precipitate was filtered off. The filtrate was concentrated under reduced pressure to obtain the title compound (1.01 g).

$^1$H NMR (400 MHz, DMSO-$d_6$) delta 2.25 (3H, s), 4.42 (2H, d, J=5.8 Hz), 5.06 (2H, s), 5.11 (1H, t, J=5.7 Hz), 6.60-6.84 (3H, m), 7.22-7.49 (5H, m).

B) 3-(Benzyloxy)-5-methylbenzaldehyde

A mixture of a sulfur trioxide-pyridine complex (2.113 g) and dimethyl sulfoxide (10 mL) was added dropwise to a mixture of (3-(benzyloxy)-5-methylphenyl)methanol (1.01 g), triethylamine (3.08 mL), and dimethyl sulfoxide (5 mL) at room temperature, and the obtained mixture was stirred overnight at room temperature. To the reaction mixture, water was added, followed by extraction with ethyl acetate. The extract was washed with 1 M hydrochloric acid and brine and dried over anhydrous magnesium sulfate, and then, the solvent was distilled off under reduced pressure to obtain the title compound (0.948 g).

$^1$H NMR (400 MHz, DMSO-$d_6$) delta 2.37 (3H, s), 5.17 (2H, s), 7.03-7.54 (8H, m), 9.93 (1H, s).

C) (E)-1-(3-(Benzyloxy)-5-methylphenyl)-N-hydroxymethanimine

A mixture of 3-(benzyloxy)-5-methylbenzaldehyde (948 mg), hydroxyl ammonium chloride (320 mg), sodium bicarbonate (837 mg), and ethanol (10 mL) was stirred overnight at room temperature. To the reaction mixture, water and brine were added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (804 mg).

MS: [M+H]$^+$ 242.2.

D) tert-Butyl 3-(3-(benzyloxy)-5-methylphenyl)-5-(2-tert-butoxy-2-oxoethyl)-4,5-dihydro-1,2-oxazole-5-carboxylate An aqueous sodium hypochlorite solution (5%, 2715 mg) was added dropwise to a THF (4 mL) solution of (E)-1-(3-(benzyloxy)-5-methylphenyl)-N-hydroxymethanimine (400 mg) and di-tert-butyl 2-methylenesuccinate (402 mg) at 0 C, and the obtained mixture was stirred at 0 C for 2 hours and subsequently at room temperature for 3 days. The reaction mixture was diluted with ethyl acetate, and water was added thereto. The organic layer was washed with brine and dried over anhydrous magnesium sulfate, and then, the solvent was distilled off under reduced pressure. The residue was purified by silica gel column chromatography (ethyl acetate/hexane) to obtain the title compound (674 mg).

MS: [M+Na]$^+$ 504.2.

E) tert-Butyl 5-(2-tert-butoxy-2-oxoethyl)-3-(3-hydroxy-5-methylphenyl)-4,5-dihydro-1,2-oxazole-5-carboxylate A mixture of tert-butyl 3-(3-(benzyloxy)-5-methylphenyl)-5-(2-tert-butoxy-2-oxoethyl)-4,5-dihydro-1,2-oxazole-5-carboxylate (674 mg), 10% Pd/C (containing about 55% water, 67 mg), and THF (7 mL) was stirred overnight at room temperature in a hydrogen atmosphere. The catalyst was filtered off, and then, the filtrate was concentrated under reduced pressure. The residue was purified by silica gel column chromatography (ethyl acetate/hexane) to obtain the title compound (500 mg).

MS: [M+Na]$^+$ 414.2.

F) tert-Butyl 5-(2-tert-butoxy-2-oxoethyl)-3-(3-((4-carbamimidamidobenzoyl)oxy)-5-methylphenyl)-4,5-dihydro-1,2-oxazole-5-carboxylate 4-Carbamimidamidobenzoyl chloride hydrochloride (299 mg) was added to a mixture of tert-butyl 5-(2-tert-butoxy-2-oxoethyl)-3-(3-hydroxy-5-methylphenyl)-4,5-dihydro-1,2-oxazole-5-carboxylate (500 mg), pyridine (0.6 mL), and NMP (0.6 mL) at 50 C, and the obtained mixture was stirred at 50 C for 30 minutes. Further, 4-carbamimidamidobenzoyl chloride hydrochloride (299 mg) was added thereto, and the obtained mixture was stirred at 50 C for 3 hours. The reaction mixture was fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (407 mg).

MS: [M+H]$^+$ 553.3.

G) 3-(3-((4-Carbamimidamidobenzoyl)oxy)-5-methylphenyl)-5-(carboxymethyl)-4,5-dihydro-1,2-oxazole-5-carboxylic acid trifluoroacetate A mixture of tert-butyl 5-(2-tert-butoxy-2-oxoethyl)-3-(3-((4-carbamimidamidobenzoyl)oxy)-5-methylphenyl)-4,5-dihydro-1,2-oxazole-5-carboxylate (407 mg) and TFA (4 mL) was stirred overnight at room temperature. The reaction mixture was concentrated under reduced pressure, and then, the residue was washed with diethyl ether to obtain the title compound (289 mg).

$^1$H NMR (400 MHz, DMSO-$d_6$) delta 2.39 (3H, s), 2.96 (2H, brs), 3.49 (1H, d, J=18.1 Hz), 3.89 (1H, d, J=17.4 Hz), 7.22 (1H, s), 7.33-7.54 (4H, m), 7.79 (4H, brs), 8.16 (2H, d, J=8.5 Hz), 10.20 (1H, brs).

Example 14

3-(3-((4-Carbamimidamidobenzoyl)oxy)-5-(2-carboxyethyl)phenyl)-5-(carboxymethyl)-4,5-dihydro-1,2-oxazole-5-carboxylic acid trifluoroacetate

A) (E)-1-(3-(Benzyloxy)-5-bromophenyl)-N-hydroxymethanimine

A mixture of 3-(benzyloxy)-5-bromobenzaldehyde (5.05 g), hydroxyl ammonium chloride (1.326 g), sodium bicarbonate (1.603 g), and ethanol (50 mL) was stirred overnight at room temperature. To the reaction mixture, water and brine were added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (1.48 g).

$^1$H NMR (400 MHz, DMSO-$d_6$) delta 5.15 (2H, s), 7.13-7.55 (8H, m), 8.10 (1H, s), 11.46 (1H, s).

B) tert-Butyl 3-(3-(benzyloxy)-5-bromophenyl)-5-(2-tert-butoxy-2-oxoethyl)-4,5-dihydro-1,2-oxazole-5-carboxylate An aqueous sodium hypochlorite solution (5%, 7.92 g) was added dropwise to a solution of (E)-1-(3-(benzyloxy)-5-bromophenyl)-N-hydroxymethanimine (1.48 g) and di-tert-butyl 2-methylenesuccinate (1.171 g) in THF (15 mL) at 0 C, and the obtained mixture was stirred at 0 C for 2 hours and subsequently at room temperature for 3 days. The reaction mixture was diluted with ethyl acetate, and water was added thereto. The organic layer was washed with brine and dried over anhydrous magnesium sulfate, and then, the solvent was distilled off under reduced pressure. The residue was purified by silica gel column chromatography (ethyl acetate/hexane) to obtain the title compound (1.67 g).

$^1$H NMR (400 MHz, DMSO-$d_6$) delta 1.40 (9H, s), 1.42 (9H, s), 2.87-3.08 (2H, m), 3.54 (1H, d, J=17.8 Hz), 3.85 (1H, d, J=17.7 Hz), 5.19 (2H, s), 7.16-7.50 (8H, m).

C) tert-Butyl 3-(3-(benzyloxy)-5-((1E)-3-tert-butoxy-3-oxoprop-1-en-1-yl)phenyl)-5-(2-tert-butoxy-2-oxoethyl)-4,5-dihydro-1,2-oxazole-5-carboxylate A mixture of tert-butyl 3-(3-(benzyloxy)-5-bromophenyl)-5-(2-tert-butoxy-2-oxoethyl)-4,5-dihydro-1,2-oxazole-5-carboxylate (500 mg), tert-butyl acrylate (586 mg), palladium acetate (10.27 mg), tris(2-methylphenyl)phosphine (41.8 mg), triethylamine (0.383 mL), and DMF (5 mL) was stirred at 100 C for 2 days under an argon atmosphere. To the reaction mixture, water was added, followed by extraction with ethyl acetate. The extract was washed with brine and dried over anhydrous magnesium sulfate, and then, the solvent was distilled off under reduced pressure to obtain the title compound (272 mg).
MS: [M+Na]$^+$ 616.3.

D) tert-Butyl 5-(2-tert-butoxy-2-oxoethyl)-3-(3-(3-tert-butoxy-3-oxopropyl)-5-hydroxyphenyl)-4,5-dihydro-1,2-oxazole-5-carboxylate A mixture of tert-butyl 3-(3-(benzyloxy)-5-((1E)-3-tert-butoxy-3-oxoprop-1-en-1-yl)phenyl)-5-(2-tert-butoxy-2-oxoethyl)-4,5-dihydro-1,2-oxazole-5-carboxylate (272 mg), 10% Pd/C (containing about 55% water, 27 mg), and THF (3 mL) was stirred at room temperature for 3 hours under a hydrogen atmosphere. The catalyst was filtered off, and then, the filtrate was concentrated under reduced pressure. The residue was combined with 10% Pd/C (containing about 55% water, 54 mg) and THF (3 mL), and the obtained mixture was stirred at room temperature for 2 hours under a hydrogen atmosphere. The catalyst was filtered off, and then, the filtrate was concentrated under reduced pressure. The residue was combined with 10% Pd/C (containing about 55% water, 81 mg) and THF (3 mL), and the obtained mixture was stirred overnight at room temperature under a hydrogen atmosphere. The catalyst was filtered off, and then, the filtrate was concentrated under reduced pressure. The residue was purified by silica gel column chromatography (ethyl acetate/hexane) to obtain the title compound (167 mg).
MS: [M+Na]$^+$ 528.3.

E) tert-Butyl 5-(2-tert-butoxy-2-oxoethyl)-3-(3-(3-tert-butoxy-3-oxopropyl)-5-((4-carbamimidamidobenzoyl)oxy)phenyl)-4,5-dihydro-1,2-oxazole-5-carboxylate 4-Carbamimidamidobenzoyl chloride hydrochloride (77 mg) was added to a mixture of tert-butyl 5-(2-tert-butoxy-2-oxoethyl)-3-(3-(3-tert-butoxy-3-oxopropyl)-5-hydroxyphenyl)-4,5-dihydro-1,2-oxazole-5-carboxylate (167 mg), pyridine (0.16 mL), and NMP (0.16 mL) at 50 C, and the obtained mixture was stirred at 50 C for 30 minutes. Further, 4-carbamimidamidobenzoyl chloride hydrochloride (77 mg) was added thereto, and the obtained mixture was stirred at 50 C for 3 hours. Pyridine (0.16 mL) and NMP (0.16 mL) were added thereto, then 4-carbamimidamidobenzoyl chloride hydrochloride (77 mg) was added, and then, the obtained mixture was stirred at 50 C for 30 minutes. Further, 4-carbamimidamidobenzoyl chloride hydrochloride (77 mg) was added thereto, and the obtained mixture was stirred overnight at 50 C. The reaction mixture was fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (104 mg).
MS: [M+H]$^+$ 667.4.

F) 3-(3-((4-Carbamimidamidobenzoyl)oxy)-5-(2-carboxyethyl)phenyl)-5-(carboxymethyl)-4,5-dihydro-1,2-oxazole-5-carboxylic acid trifluoroacetate A mixture of tert-butyl 5-(2-tert-butoxy-2-oxoethyl)-3-(3-(3-tert-butoxy-3-oxopropyl)-5-((4-carbamimidamidobenzoyl)oxy)phenyl)-4,5-dihydro-1,2-oxazole-5-carboxylate (104 mg) and TFA (2 mL) was stirred overnight at room temperature. The reaction mixture was concentrated under reduced pressure, and then, the residue was washed with diethyl ether to obtain the title compound (70.0 mg).
$^1$H NMR (400 MHz, DMSO-d$_6$) delta 2.61 (2H, t, J=7.5 Hz), 2.82-3.03 (4H, m), 3.50 (1H, d, J=16.3 Hz), 3.90 (1H, d, J=17.6 Hz), 7.27 (1H, s), 7.40-7.47 (3H, m), 7.51 (1H, s), 7.79 (4H, brs), 8.17 (2H, d, J=8.4 Hz), 10.21 (1H, brs), 12.27 (1H, brs), 13.14 (1H, s).

Example 18

N-(3-(4-((4-Carbamimidamidobenzoyl)oxy)-2-(5-carboxy-5-(carboxymethyl)-4,5-dihydro-1,2-oxazol-3-yl)phenyl)propanoyl)-L-aspartic acid trifluoroacetate A) tert-Butyl 3-(5-(benzyloxy)-2-((1E)-3-(benzyloxy)-3-oxoprop-1-en-1-yl)phenyl)-5-(2-tert-butoxy-2-oxoethyl)-4,5-dihydro-1,2-oxazole-5-carboxylate A mixture of tert-butyl 3-(5-(benzyloxy)-2-bromophenyl)-5-(2-tert-butoxy-2-oxoethyl)-4,5-dihydro-1,2-oxazole-5-carboxylate (1.00 g), benzyl acrylate (1.484 g), palladium acetate (0.021 g), tris(2-methylphenyl)phosphine (0.084 g), triethylamine (0.765 mL), and DMF (10 mL) was stirred at 100 C for 2 days in an argon atmosphere. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (0.260 g).
MS: [M+Na]$^+$ 650.3.

B) 3-(2-(5-(tert-Butoxycarbonyl)-5-(2-tert-butoxy-2-oxoethyl)-4,5-dihydro-1,2-oxazol-3-yl)-4-hydroxyphenyl)propanoic acid A mixture of tert-butyl 3-(5-(benzyloxy)-2-((1E)-3-(benzyloxy)-3-oxoprop-1-en-1-yl)phenyl)-5-(2-tert-butoxy-2-oxoethyl)-4,5-dihydro-1,2-oxazole-5-carboxylate (260 mg), 10% Pd/C (containing about 55% water, 26 mg), and THF (3 mL) was stirred overnight at room temperature under a hydrogen atmosphere. The catalyst was filtered off, and then, the filtrate was concentrated under reduced pressure. The residue was combined with 10% Pd/C (containing about 55% water, 52 mg) and THF (3 mL), and the obtained mixture was stirred at room temperature for 3 hours under a hydrogen atmosphere. The catalyst was filtered off, and then, the filtrate was concentrated under reduced pressure to obtain the title compound (214 mg).
MS: [M+Na]$^+$ 472.2.

C) Di-tert-butyl N-(3-(2-(5-(tert-butoxycarbonyl)-5-(2-tert-butoxy-2-oxoethyl)-4,5-dihydro-1,2-oxazol-3-yl)-4-hydroxyphenyl)propanoyl)-L-aspartate A mixture of 3-(2-(5-(tert-butoxycarbonyl)-5-(2-tert-butoxy-2-oxoethyl)-4,5-dihydro-1,2-oxazol-3-yl)-4-hydroxyphenyl)propanoic acid (214 mg), di-tert-butyl L-aspartate hydrochloride (161 mg), WSC (89 mg), HOBt (77 mg), triethylamine (0.080 mL), and DMF (2 mL) was stirred at room temperature for 3 days. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (154 mg).

MS: [M+H]$^+$ 677.3.

D) Di-tert-butyl N-(3-(2-(5-(tert-butoxycarbonyl)-5-(2-tert-butoxy-2-oxoethyl)-4,5-dihydro-1,2-oxazol-3-yl)-4-((4-carbamimidamidobenzoyl)oxy)phenyl)propanoyl)-L-aspartate 4-Carbamimidamidobenzoyl chloride hydrochloride (53.3 mg) was added to a mixture of di-tert-butyl N-(3-(2-(5-(tert-butoxycarbonyl)-5-(2-tert-butoxy-2-oxoethyl)-4,5-dihydro-1,2-oxazol-3-yl)-4-hydroxyphenyl)propanoyl)-L-aspartate (154 mg), pyridine (0.12 mL), and NMP (0.12 mL) at 50 C, and the obtained mixture was stirred at 50 C for 30 minutes. Further, 4-carbamimidamidobenzoyl chloride hydrochloride (53.3 mg) was added thereto, and the obtained mixture was stirred overnight at 50 C. The reaction mixture was fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (44.6 mg).

MS: [M+H]$^+$ 838.5.

E) N-(3-(4-((4-Carbamimidamidobenzoyl)oxy)-2-(5-carboxy-5-(carboxymethyl)-4,5-dihydro-1,2-oxazol-3-yl)phenyl)propanoyl)-L-aspartic acid trifluoroacetate A mixture of di-tert-butyl N-(3-(2-(5-(tert-butoxycarbonyl)-5-(2-tert-butoxy-2-oxoethyl)-4,5-dihydro-1,2-oxazol-3-yl)-4-((4-carbamimidamidobenzoyl)oxy)phenyl)propanoyl)-L-aspartate (44.6 mg) and TFA (1 mL) was stirred overnight at room temperature. The reaction mixture was concentrated under reduced pressure, and then, the residue was washed with diethyl ether to obtain the title compound (25.1 mg).

$^1$H NMR (400 MHz, DMSO-d$_6$) delta 2.36-2.73 (4H, m), 2.99 (2H, brs), 3.07 (2H, t, J=7.0 Hz), 3.57 (1H, d, J=16.9 Hz), 3.92 (1H, d, J=16.8 Hz), 4.42-4.61 (1H, m), 7.18-7.34 (1H, m), 7.37-7.54 (4H, m), 7.74 (4H, brs), 8.01-8.29 (3H, m), 10.09 (1H, brs), 12.82 (4H, s).

Example 22

3-(4-(2-(5,5-Bis(carboxymethyl)-4,5-dihydro-1,2-oxazol-3-yl)-4-((4-carbamimidamidobenzoyl)oxy)phenyl)piperidin-1-yl)propanoic acid ditrifluoroacetate

A) tert-Butyl 3-(4-(4,4,5,5-tetramethyl-1,3,2-dioxaborolan-2-yl)-3,6-dihydropyridin-1(2H)-yl)propanoate A mixture of 4-(4,4,5,5-tetramethyl-1,3,2-dioxaborolan-2-yl)-1,2,3,6-tetrahydropyridine hydrochloride (100 mg), tert-butyl acrylate (0.089 mL), potassium carbonate (169 mg), and acetonitrile (2 mL) was stirred overnight at 70 C. In another reaction vessel, a mixture of 4-(4,4,5,5-tetramethyl-1,3,2-dioxaborolan-2-yl)-1,2,3,6-tetrahydropyridine hydrochloride (1.00 g), tert-butyl acrylate (0.895 mL), potassium carbonate (1.688 g), and acetonitrile (10 mL) was stirred overnight at 70 C. These two reaction mixtures were combined, and water was added thereto, followed by extraction with ethyl acetate. The extract was washed with brine and dried over anhydrous magnesium sulfate, and then, the solvent was distilled off under reduced pressure. The residue was purified by silica gel column chromatography (NH, ethyl acetate/hexane) to obtain the title compound (1.11 g).

MS: [M+H]$^+$ 338.2.

B) tert-Butyl 3-(4-(4-(benzyloxy)-2-(5,5-bis(2-tert-butoxy-2-oxoethyl)-4,5-dihydro-1,2-oxazol-3-yl)phenyl)-3,6-dihydropyridin-1(2H)-yl)propanoate A mixture of di-tert-butyl 2,2'-(3-(5-(benzyloxy)-2-bromophenyl)-4,5-dihydro-1,2-oxazole-5,5-diyl)diacetate (200 mg), tert-butyl 3-(4-(4,4,5,5-tetramethyl-1,3,2-dioxaborolan-2-yl)-3,6-dihydropyridin-1(2H)-yl)propanoate (144 mg), [1,1'-bis(diphenylphosphino)ferrocene]palladium(II) dichloride (26.1 mg), a 2 M aqueous cesium carbonate solution (0.5 mL), and DME (2 mL) was stirred at 90 C for 2 hours under microwave irradiation under an argon atmosphere. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (245 mg).

MS: [M+H]$^+$ 691.4.

C) tert-Butyl 3-(4-(2-(5,5-bis(2-tert-butoxy-2-oxoethyl)-4,5-dihydro-1,2-oxazol-3-yl)-4-hydroxyphenyl)piperidin-1-yl)propanoate A mixture of tert-butyl 3-(4-(4-(benzyloxy)-2-(5,5-bis(2-tert-butoxy-2-oxoethyl)-4,5-dihydro-1,2-oxazol-3-yl)phenyl)-3,6-dihydropyridin-1(2H)-yl)propanoate (245 mg), 10% Pd/C (containing about 55% water, 25 mg), and THF (3 mL) was stirred at room temperature for 3 hours under a hydrogen atmosphere. The catalyst was filtered off, and then, the filtrate was concentrated under reduced pressure. The obtained residue was mixed with 10% Pd/C (containing about 55% water, 50 mg) and THF (3 mL). The obtained mixture was stirred at room temperature for 3 hours under a hydrogen atmosphere. The catalyst was filtered off, and then, the filtrate was concentrated under reduced pressure. The obtained residue was mixed with 10% Pd/C (containing about 55% water, 75 mg) and THF (3 mL). The obtained mixture was stirred overnight at room temperature under a hydrogen atmosphere. The catalyst was filtered off, and then, the filtrate was concentrated under reduced pressure. The residue was purified by silica gel column chromatography (ethyl acetate/hexane) to obtain the title compound (60.7 mg).

MS: [M+H]$^+$ 603.4.

D) 3-(5,5-Bis(2-tert-butoxy-2-oxoethyl)-4,5-di-hydro-1,2-oxazol-3-yl)-4-(1-(3-tert-butoxy-3-oxo-propyl)piperidin-4-yl)phenyl 4-carbamimidamido-benzoate 4-Carbamimidamidobenzoyl chloride hydrochloride (23.57 mg) was added to a mixture of tert-butyl 3-(4-(2-(5,5-bis(2-tert-butoxy-2-oxoethyl)-4,5-dihydro-1,2-oxazol-3-yl)-4-hydroxyphenyl)piperidin-1-yl)propanoate (60.7 mg), pyridine (0.2 mL), and NMP (0.2 mL) at 50 C, and the obtained mixture was stirred at 50 C for 30 minutes. 4-Carbamimidamidobenzoyl chloride hydrochloride (23.57 mg) was further added thereto, and the obtained mixture was stirred at 50 C for 30 minutes. 4-Carbamimidamidobenzoyl chloride hydrochloride (23.57 mg) was further added thereto, and the obtained mixture was stirred at 50 C for 30 minutes. 4-Carbamimidamidobenzoyl chloride hydrochloride (23.57 mg) was further added thereto, and the obtained mixture was stirred overnight at 50 C. To the reaction mixture, acetonitrile was added. The precipitate was filtered off, and then, the filtrate was concentrated under reduced pressure. The residue was purified by silica gel column chromatography (NH, ethyl acetate/hexane, subsequently methanol/ethyl acetate) to obtain the title compound (42.7 mg).

MS: [M+H]$^+$ 764.4.

E) 3-(4-(2-(5,5-Bis(carboxymethyl)-4,5-dihydro-1,2-oxazol-3-yl)-4-((4-carbamimidamidobenzoyl)oxy) phenyl)piperidin-1-yl)propanoic acid ditrifluoroac-etate A mixture of 3-(5,5-bis(2-tert-butoxy-2-oxoethyl)-4,5-dihydro-1,2-oxazol-3-yl)-4-(1-(3-tert-butoxy-3-oxopropyl)piperidin-4-yl)phenyl 4-carbamimidamidobenzoate (42.7 mg) and TFA (1 mL) was stirred at 50 C for 1 hour. The reaction mixture was concentrated under reduced pressure, and then, the residue was washed with diethyl ether to obtain the title compound (35.6 mg).

$^1$H NMR (400 MHz, DMSO-d$_6$) delta 1.79-2.10 (4H, m), 2.79 (2H, t, J=7.1 Hz), 2.83-2.98 (4H, m), 3.00-3.13 (2H, m), 3.27-3.65 (8H, m), 7.33-7.54 (5H, m), 7.81 (4H, brs), 8.16 (2H, d, J=7.4 Hz), 10.22 (1H, brs), 12.22-13.03 (3H, m).

Example 25

2,2'-(3-(5-((4-Carbamimidamidobenzoyl)oxy)-2-(3-(1,1-dioxidothiomorpholin-4-yl)-3-oxopropyl)phe-nyl)-4,5-dihydro-1,2-oxazole-5,5-diyl)diacetic acid

A) Di-tert-butyl 2,2'-(3-(2-(3-(1,1-dioxidothiomor-pholin-4-yl)-3-oxopropyl)-5-hydroxyphenyl)-4,5-dihydro-1,2-oxazole-5,5-diyl)diacetate A mixture of 3-(2-(5,5-bis(2-tert-butoxy-2-oxoethyl)-4,5-dihydro-1,2-oxazol-3-yl)-4-hydroxyphenyl)propanoic acid (317 mg), thiomorpholine 1,1-dioxide (92 mg), WSC (106 mg), HOBt (92 mg), and DMF (3 mL) was stirred at room temperature for 7 hours. To the reaction mixture, 0.1 M hydrochloric acid was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (140 mg).

MS: [M+H]$^+$ 581.3.

B) 3-(5,5-Bis(2-tert-butoxy-2-oxoethyl)-4,5-di-hydro-1,2-oxazol-3-yl)-4-(3-(1,1-dioxidothiomor-pholin-4-yl)-3-oxopropyl)phenyl 4-carbamimidami-dobenzoate 4-Carbamimidamidobenzoyl chloride hydrochloride (56.4 mg) was added to a mixture of di-tert-butyl 2,2'-(3-(2-(3-(1,1-dioxidothiomorpholin-4-yl)-3-oxopropyl)-5-hy-droxyphenyl)-4,5-dihydro-1,2-oxazole-5,5-diyl)diacetate (140 mg), pyridine (0.2 mL), and NMP (0.2 mL) at 50 C, and the obtained mixture was stirred at 50 C for 30 minutes. 4-Carbamimidamidobenzoyl chloride hydrochloride (56.4 mg) was further added thereto, and the obtained mixture was stirred at 50 C for 30 minutes. 4-Carbamimidamidobenzoyl chloride hydrochloride (56.4 mg) was further added thereto, and the obtained mixture was stirred at 50 C for 3 hours. Pyridine (0.2 mL) and NMP (0.2 mL) were further added thereto, 4-carbamimidamidobenzoyl chloride hydrochloride (56.4 mg) was added thereto, and then, the obtained mixture was stirred at 50 C for 30 minutes. 4-Carbamimidamidobenzoyl chloride hydrochloride (56.4 mg) was further added thereto, and the obtained mixture was stirred at 50 C for 30 minutes. 4-carbamimidamidobenzoyl chloride hydrochloride (56.4 mg) was further added thereto, and the obtained mixture was stirred overnight at 50 C. To the reaction mixture, acetonitrile was added. The precipitate was filtered off, and then, the filtrate was concentrated under reduced pressure. The residue was fractionated by HPLC (C18, mobile phase: water/acetonitrile (system containing 0.1% TFA)). To the obtained fraction, a saturated aqueous solution of sodium bicarbonate was added, followed by extraction with ethyl acetate. The extract was dried over anhydrous magnesium sulfate, and the solvent was distilled off under reduced pressure to obtain the title compound (49.0 mg).

MS: [M+H]$^+$ 742.3.

C) 2,2'-(3-(5-((4-Carbamimidamidobenzoyl)oxy)-2-(3-(1,1-dioxidothiomorpholin-4-yl)-3-oxopropyl) phenyl)-4,5-dihydro-1,2-oxazole-5,5-diyl)diacetic acid A mixture of 3-(5,5-bis(2-tert-butoxy-2-oxoethyl)-4,5-di-hydro-1,2-oxazol-3-yl)-4-(3-(1,1-dioxidothiomorpholin-4-yl)-3-oxopropyl)phenyl 4-carbamimidamidobenzoate (49.0 mg) and TFA (1 mL) was stirred at room temperature for 2 hours. The reaction mixture was concentrated under reduced pressure, and then, the pH of the residue was adjusted to about 4 by the addition of water and subsequently a saturated aqueous solution of ammonium acetate. The obtained mixture was stirred at room temperature for 3 days, and then, the obtained solid was collected by filtration and washed with water and acetone to obtain the title compound (33.1 mg).

$^1$H NMR (400 MHz, DMSO-d$_6$) delta 2.57-2.80 (6H, m), 3.05-3.21 (6H, m), 3.42-3.56 (2H, m), 3.79-3.94 (4H, m), 7.20-7.40 (4H, m), 7.44 (1H, d, J=8.0 Hz), 7.78 (4H, brs), 8.10 (2H, d, J=7.5 Hz).

Example 33

1-(3-(2-(5,5-Bis(carboxymethyl)-4,5-dihydro-1,2-oxazol-3-yl)-4-((4-carbamimidamidobenzoyl)oxy)phenyl)propanoyl)piperidine-4-carboxylic acid

A) Benzyl (2E)-3-(4-(benzyloxy)-2-(5,5-bis(2-methoxy-2-oxoethyl)-4,5-dihydro-1,2-oxazol-3-yl)phenyl)acrylate A mixture of dimethyl 2,2'-(3-(5-(benzyloxy)-2-bromophenyl)-4,5-dihydro-1,2-oxazole-5,5-diyl)diacetate (1.00 g), benzyl acrylate (1.021 g), palladium acetate (II) (0.047 g), tris(2-methylphenyl)phosphine (0.128 g), triethylamine (0.878 mL), and DMA (7.5 mL) was stirred at 130 C for 2 hours under microwave irradiation under an argon atmosphere. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (0.770 g).
MS: [M+H]$^+$ 558.2.

B) 3-(2-(5,5-Bis(2-methoxy-2-oxoethyl)-4,5-dihydro-1,2-oxazol-3-yl)-4-hydroxyphenyl)propanoic acid A mixture of benzyl (2E)-3-(4-(benzyloxy)-2-(5,5-bis(2-methoxy-2-oxoethyl)-4,5-dihydro-1,2-oxazol-3-yl)phenyl)acrylate (2.47 g), 10% Pd/C (containing about 55% water, 250 mg), and THF (25 mL) was stirred at room temperature for 3 hours under a hydrogen atmosphere. The catalyst was filtered off, and then, the filtrate was concentrated under reduced pressure to obtain the title compound (1.680 g).
MS: [M+H]$^+$ 380.1.

C) Ethyl 1-(3-(2-(5,5-bis(2-methoxy-2-oxoethyl)-4,5-dihydro-1,2-oxazol-3-yl)-4-hydroxyphenyl)propanoyl)piperidine-4-carboxylate A mixture of 3-(2-(5,5-bis(2-methoxy-2-oxoethyl)-4,5-dihydro-1,2-oxazol-3-yl)-4-hydroxyphenyl)propanoic acid (820 mg), ethyl piperidine-4-carboxylate (0.366 mL), WSC (497 mg), HOBt (350 mg), triethylamine (0.362 mL), and DMF (8 mL) was stirred overnight at room temperature. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (760 mg).
MS: [M+H]$^+$ 519.3.

D) 1-(3-(2-(5,5-Bis(carboxymethyl)-4,5-dihydro-1,2-oxazol-3-yl)-4-hydroxyphenyl)propanoyl)piperidine-4-carboxylic acid A mixture of ethyl 1-(3-(2-(5,5-bis(2-methoxy-2-oxoethyl)-4,5-dihydro-1,2-oxazol-3-yl)-4-hydroxyphenyl)propanoyl)piperidine-4-carboxylate (760 mg), THF (8 mL), methanol (8 mL), and a 1 M aqueous sodium hydroxide solution (8 mL) was stirred at room temperature for 2 hours. The reaction mixture was rendered acidic using 6 M hydrochloric acid at 0 C, followed by extraction with ethyl acetate. The extract was washed with brine and dried over anhydrous magnesium sulfate, and then, the solvent was distilled off under reduced pressure to obtain the title compound (664 mg).
MS: [M+H]$^+$ 463.2.

E) Benzyl 1-(3-(2-(5,5-bis(2-(benzyloxy)-2-oxoethyl)-4,5-dihydro-1,2-oxazol-3-yl)-4-hydroxyphenyl)propanoyl)piperidine-4-carboxylate (Bromomethyl)benzene (0.564 mL) was added to a solution of 1-(3-(2-(5,5-bis(carboxymethyl)-4,5-dihydro-1,2-oxazol-3-yl)-4-hydroxyphenyl)propanoyl)piperidine-4-carboxylic acid (664 mg) and N,N-diisopropylethylamine (1.103 mL) in DMF (6 mL) at room temperature, and the obtained mixture was stirred at room temperature for 4 days. To the reaction mixture, water was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (800 mg).
MS: [M+H]$^+$ 733.3.

F) Benzyl 1-(3-(2-(5,5-bis(2-(benzyloxy)-2-oxoethyl)-4,5-dihydro-1,2-oxazol-3-yl)-4-((4-nitrobenzoyl)oxy)phenyl)propanoyl)piperidine-4-carboxylate 4-Nitrobenzoyl chloride (405 mg) was added in small portions to a solution of benzyl 1-(3-(2-(5,5-bis(2-(benzyloxy)-2-oxoethyl)-4,5-dihydro-1,2-oxazol-3-yl)-4-hydroxyphenyl)propanoyl)piperidine-4-carboxylate (800 mg) in pyridine (4 mL) at 0 C. The obtained mixture was stirred at room temperature for 45 minutes. To the reaction mixture, ethyl acetate and 1 M hydrochloric acid were added 0 C, followed by extraction with ethyl acetate. Combined organic layers were washed with diluted aqueous ammonia ((28% aqueous ammonia (0.5 mL)/water (25 mL))×2), 1 M hydrochloric acid, and brine and dried over anhydrous sodium sulfate, and then, the solvent was distilled off under reduced pressure to obtain the title compound (939 mg).
MS: [M+H]$^+$ 882.3.

G) 1-(3-(4-((4-Aminobenzoyl)oxy)-2-(5,5-bis(carboxymethyl)-4,5-dihydro-1,2-oxazol-3-yl)phenyl)propanoyl)piperidine-4-carboxylic acid A mixture of benzyl 1-(3-(2-(5,5-bis(2-(benzyloxy)-2-oxoethyl)-4,5-dihydro-1,2-oxazol-3-yl)-4-((4-nitrobenzoyl)oxy)phenyl)propanoyl)piperidine-4-carboxylate (939 mg), 10% Pd/C (containing about 55% water, 100 mg), and THF (10 mL) was stirred at room temperature for 4 hours under a hydrogen atmosphere. The catalyst was filtered off, and then, the filtrate was concentrated under reduced pressure to obtain the title compound (716 mg).
MS: [M+H]$^+$ 582.3.

H) 1-(3-(2-(5,5-Bis(carboxymethyl)-4,5-dihydro-1,2-oxazol-3-yl)-4-((4-carbamimidamidobenzoyl)oxy)phenyl)propanoyl)piperidine-4-carboxylic acid A 4 M hydrogen chloride/cyclopropyl methyl ether solution (0.923 mL) was added to a mixture of 1-(3-(4-((4- aminobenzoyl)oxy)-2-(5,5-bis(carboxymethyl)-4,5-dihydro-1,2-oxazol-3-yl)phenyl)propanoyl)piperidine-4-carboxylic acid (716 mg), cyanamide (155 mg), and tert-butyl alcohol (14 mL) at room temperature. The obtained mixture was stirred overnight at 50 C and then concentrated under reduced pressure. A mixture of the obtained residue and water (7 mL) was added dropwise to an aqueous solution prepared from ammonium acetate (285 mg) and water (7 mL) at room temperature. To the obtained suspension, water (7 mL) was added, and the mixture was stirred overnight at room temperature. The solid was collected by filtration and washed with water and acetone to obtain a crude product (600 mg).

The crude product (100 mg) obtained by the above-mentioned method was fractionated by HPLC (C18, mobile phase: water/acetonitrile (system containing 0.1% TFA)), and the obtained fraction was concentrated under reduced pressure. The pH of the obtained residue was adjusted to about 4 by the addition of water and subsequently an aqueous ammonium acetate solution. The obtained mixture was stirred overnight at room temperature, and then, the obtained solid was collected by filtration and washed with water and acetone to obtain the title compound (67.4 mg).

$^1$H NMR (400 MHz, DMSO-$d_6$) delta 1.30-1.48 (2H, m), 1.77 (2H, d, J=11.3 Hz), 2.37-2.81 (8H, m), 2.97-3.14 (3H, m), 3.51 (2H, brs), 3.78 (1H, d, J=13.1 Hz), 4.19 (1H, d, J=12.8 Hz), 7.24 (1H, dd, J=8.5, 2.1 Hz), 7.29-7.39 (3H, m), 7.42 (1H, d, J=8.5 Hz), 7.55-8.51 (6H, m), 12.91 (2H, brs).

Example 34

2,2'-(3-(5-((4-Carbamimidamidobenzoyl)oxy)-2-(3-oxo-3-((2-sulfoethyl)amino)propyl)phenyl)-4,5-dihydro-1,2-oxazole-5,5-diyl)diacetic acid A) Benzyl 3-(2-(5,5-bis(2-tert-butoxy-2-oxoethyl)-4,5-dihydro-1,2-oxazol-3-yl)-4-hydroxyphenyl)propanoate A mixture of 3-(2-(5,5-bis(2-tert-butoxy-2-oxoethyl)-4,5-dihydro-1,2-oxazol-3-yl)-4-hydroxyphenyl)propanoic acid (413 mg), (bromomethyl)benzene (0.117 mL), N,N-diisopropylethylamine (0.342 mL), and DMF (4 mL) was stirred overnight at room temperature. To the reaction mixture, 0.1 M hydrochloric acid was added, followed by extraction with ethyl acetate. The extract was washed with brine and dried over anhydrous magnesium sulfate, and then, the solvent was distilled off under reduced pressure. The residue was purified by silica gel column chromatography (ethyl acetate/hexane) to obtain the title compound (227 mg).

MS: [M+H]$^+$ 554.3.

B) 4-(3-(Benzyloxy)-3-oxopropyl)-3-(5,5-bis(2-tert-butoxy-2-oxoethyl)-4,5-dihydro-1,2-oxazol-3-yl) phenyl 4-carbamimidamidobenzoate 4-Carbamimidamidobenzoyl chloride hydrochloride (96 mg) was added to a mixture of benzyl 3-(2-(5,5-bis(2-tert-butoxy-2-oxoethyl)-4,5-dihydro-1,2-oxazol-3-yl)-4-hydroxyphenyl)propanoate (227 mg), pyridine (0.2 mL), and NMP (0.2 mL) at 50 C, and the obtained mixture was stirred at 50 C for 30 minutes. 4-Carbamimidamidobenzoyl chloride hydrochloride (96 mg) was further added thereto, and the obtained mixture was stirred overnight at 50 C. To the reaction mixture, acetonitrile was added. The precipitate was filtered off, and then, the filtrate was concentrated under reduced pressure. The residue was purified by silica gel column chromatography (NH, ethyl acetate/hexane, subsequently methanol/ethyl acetate) to obtain the title compound (163 mg).

MS: [M+H]$^+$ 715.4.

C) 3-(2-(5,5-Bis(2-tert-butoxy-2-oxoethyl)-4,5-dihydro-1,2-oxazol-3-yl)-4-((4-carbamimidamidobenzoyl)oxy)phenyl)propanoic acid trifluoroacetate A mixture of 4-(3-(benzyloxy)-3-oxopropyl)-3-(5,5-bis(2-tert-butoxy-2-oxoethyl)-4,5-dihydro-1,2-oxazol-3-yl) phenyl 4-carbamimidamidobenzoate (163 mg), 10% Pd/C (containing about 55% water, 20 mg), THF (1.8 mL), and acetic acid (0.2 mL) was stirred at room temperature for 4 hours under a hydrogen atmosphere. The catalyst was filtered and washed with THF, and then, the filtrate was concentrated under reduced pressure. The residue was fractionated by HPLC (C18, mobile phase: water/acetonitrile (system containing 0.1% TFA)), and the obtained fraction was concentrated under reduced pressure to obtain the title compound (160 mg).

MS: [M+H]$^+$ 625.4.

D) 2,2'-(3-(5-((4-Carbamimidamidobenzoyl)oxy)-2-(3-oxo-3-((2-sulfoethyl)amino)propyl)phenyl)-4,5-dihydro-1,2-oxazole-5,5-diyl)diacetic acid A mixture of 3-(2-(5,5-bis(2-tert-butoxy-2-oxoethyl)-4,5-dihydro-1,2-oxazol-3-yl)-4-((4-carbamimidamidobenzoyl)oxy)phenyl)propanoic acid trifluoroacetate (160 mg), taurine (32.5 mg), WSC (50.4 mg), HOBt (43.9 mg), N,N-diisopropylethylamine (0.057 mL), and DMF (5 mL) was stirred overnight at room temperature. The reaction mixture was fractionated by HPLC (C18, mobile phase: water/acetonitrile (system containing 0.1% TFA)). The obtained fraction was concentrated under reduced pressure. To the obtained residue, TFA (4 mL) was added, and the obtained mixture was stirred at room temperature for 2 hours. The reaction mixture was concentrated under reduced pressure, and then, the pH of the residue was adjusted to about 4 by the addition of an aqueous ammonium acetate solution. The mixture was stirred at room temperature for 2 hours, and then, the obtained solid was collected by filtration and washed with water and acetone to obtain the title compound (40.3 mg).

$^1$H NMR (400 MHz, DMSO-$d_6$) delta 2.35 (2H, t, J=7.5 Hz), 2.45-2.56 (2H, m), 2.78-2.95 (4H, m), 3.07 (2H, t, J=7.3 Hz), 3.26-3.38 (2H, m), 3.56 (2H, s), 7.20-7.28 (1H, m), 7.32-7.45 (4H, m), 7.58-7.81 (5H, m), 8.17 (2H, d, J=8.5 Hz), 12.49 (2H, brs).

In Examples 2, 4, 9, 10, 12, 13, 15 to 17, 19 to 21, 23 to 24 and 26 to 32, compounds were produced according to the above-mentioned methods or methods equivalent thereto. The compounds of Examples are shown in tables below. MS in the tables are indicated by actual measurement value.

TABLE 1

| EXAMPLE | IUPACNAME | Structure | Salt | MS |
|---|---|---|---|---|
| 1 | (5R)-3-(3-((4-carbamimidamidobenzoyl)oxy)phenyl)-5-(carboxymethyl)-4,5-dihydro-1,2-oxazole-5-carboxylic acid | 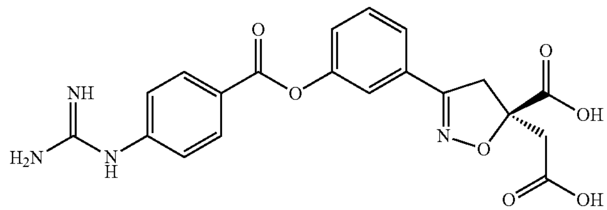 [SMILES: N=C(N)Nc1ccc(C(=O)Oc2cccc(C3=NO[C@](CC(=O)O)(C(=O)O)C3)c2)cc1] | | 426.9 |
| 2 | 3-(4-((4-carbamimidamidobenzoyl)oxy)phenyl)-5-(carboxymethyl)-4,5-dihydro-1,2-oxazole-5-carboxylic acid | 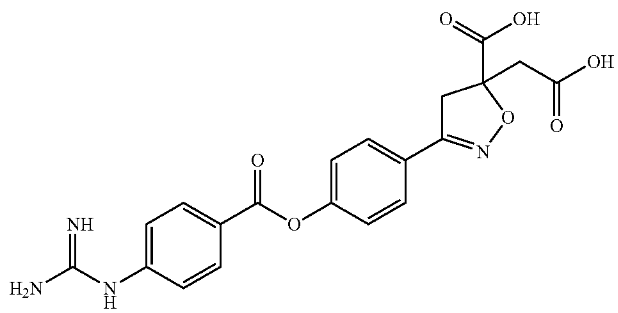 [SMILES: N=C(N)Nc1ccc(C(=O)Oc2ccc(C3=NOC(CC(=O)O)(C(=O)O)C3)cc2)cc1] | $CF_3COOH$ | 427.0 |
| 3 | 3-(5-((4-carbamimidamidobenzoyl)oxy)-2-methylphenyl)-5-(carboxymethyl)-4,5-dihydro-1,2-oxazole-5-carboxylic acid | 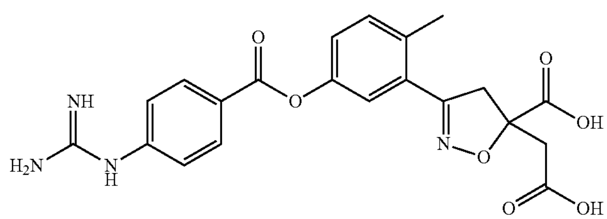 [SMILES: Cc1ccc(OC(=O)c2ccc(NC(=N)N)cc2)cc1C1=NOC(CC(=O)O)(C(=O)O)C1] | $CF_3COOH$ | 441.1 |
| 4 | 3,3'-(3-(3-((4-carbamimidamidobenzoyl)oxy)phenyl)-4,5-dihydro-1,2-oxazole-5,5-diyl)dipropanoic acid | 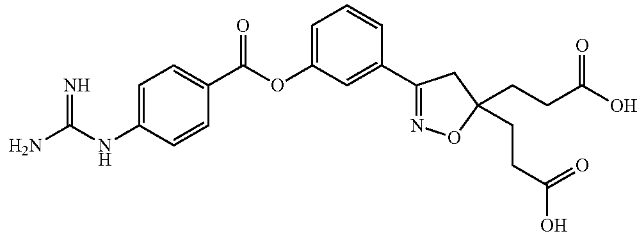 [SMILES: N=C(N)Nc1ccc(C(=O)Oc2cccc(C3=NOC(CCC(=O)O)(CCC(=O)O)C3)c2)cc1] | $CF_3COOH$ | 469.1 |
| 5 | (5S)-3-(3-((4-carbamimidamidobenzoyl)oxy)phenyl)-5-(carboxymethyl)-4,5-dihydro-1,2-oxazole-5-carboxylic acid | 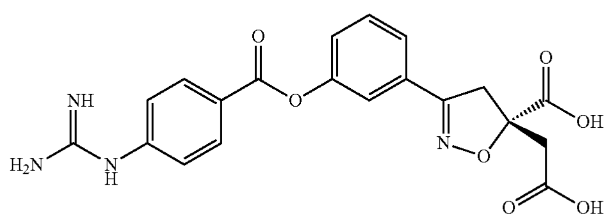 [SMILES: N=C(N)Nc1ccc(C(=O)Oc2cccc(C3=NO[C@@](CC(=O)O)(C(=O)O)C3)c2)cc1] | | 427.0 |
| 6 | 2,2'-(3-(3-((4-carbamimidamidobenzoyl)oxy)phenyl)-4,5-dihydro-1,2-oxazole-5,5-diyl)diacetic acid | 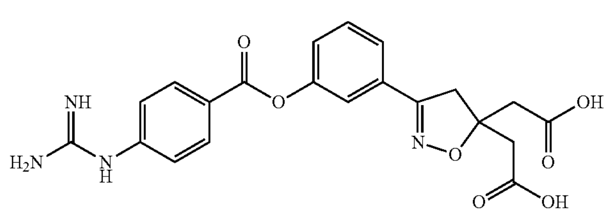 [SMILES: N=C(N)Nc1ccc(C(=O)Oc2cccc(C3=NOC(CC(=O)O)(CC(=O)O)C3)c2)cc1] | | 439.1 |

TABLE 1-continued

| EXAMPLE | IUPACNAME | Structure | Salt | MS |
|---|---|---|---|---|
| 7 | 4-(4-(2-(5,5-bis(carboxymethyl)-4,5-dihydro-1,2-oxazol-3-yl)-4-((4-carbamimidamidobenzoyl)oxy)phenyl)piperidin-1-yl)-4-oxobutanoic acid | 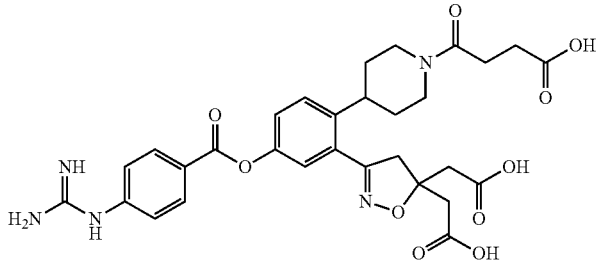 [SMILES: N=C(N)Nc1ccc(C(=O)Oc2ccc(C3CCN(C(=O)CCC(=O)O)CC3)c(C3=NOC(CC(=O)O)(CC(=O)O)C3)c2)cc1] | CF$_3$COOH | 624.2 |
| 8 | 3-(5-((4-carbamimidamidobenzoyl)oxy)-2-cyclohexylphenyl)-5-(carboxymethyl)-4,5-dihydro-1,2-oxazole-5-carboxylic acid | 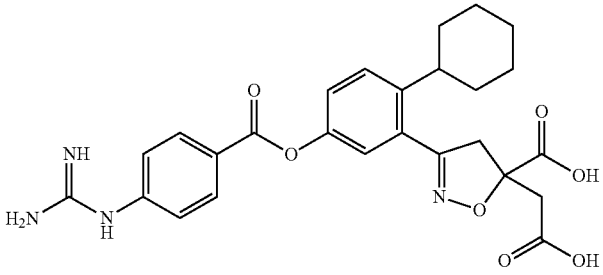 [SMILES: N=C(N)Nc1ccc(C(=O)Oc2ccc(C3CCCCC3)c(C3=NOC(CC(=O)O)(C(=O)O)C3)c2)cc1] | CF$_3$COOH | 509.1 |
| 9 | 3-(4-((4-carbamimidamidobenzoyl)oxy)biphenyl-2-yl)-5-(carboxymethyl)-4,5-dihydro-1,2-oxazole-5-carboxylic acid | 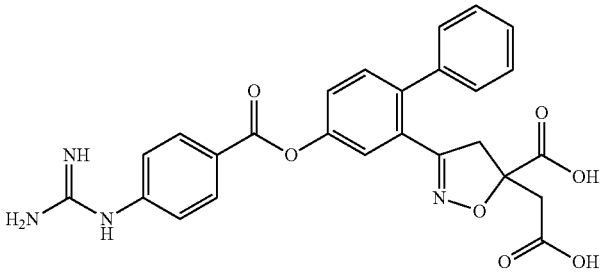 [SMILES: N=C(N)Nc1ccc(C(=O)Oc2ccc(-c3ccccc3)c(C3=NOC(CC(=O)O)(C(=O)O)C3)c2)cc1] | CF$_3$COOH | 503.0 |
| 10 | 3-(2-(4-tert-butylcyclohexyl)-5-((4-carbamimidamidobenzoyl)oxy)phenyl)-5-(carboxymethyl)-4,5-dihydro-1,2-oxazole-5-carboxylic acid | 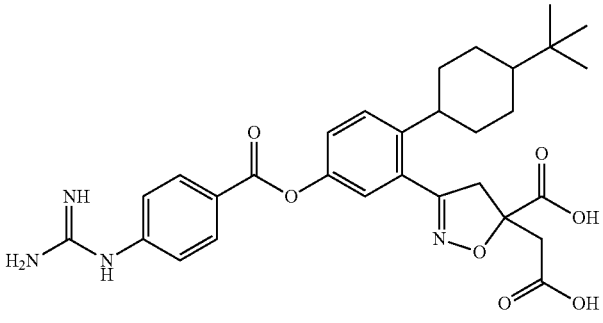 [SMILES: CC(C)(C)C1CCC(c2ccc(OC(=O)c3ccc(NC(=N)N)cc3)cc2C2=NOC(CC(=O)O)(C(=O)O)C2)CC1] | CF$_3$COOH | 565.1 |
| 11 | 3-(3-((4-carbamimidamidobenzoyl)oxy)-5-methylphenyl)-5-(carboxymethyl)-4,5-dihydro-1,2-oxazole-5-carboxylic acid | 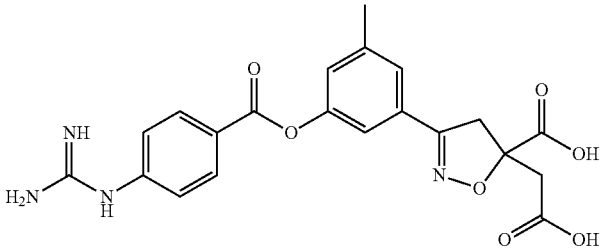 [SMILES: Cc1cc(OC(=O)c2ccc(NC(=N)N)cc2)cc(C2=NOC(CC(=O)O)(C(=O)O)C2)c1] | CF$_3$COOH | 441.0 |

TABLE 1-continued

| EXAMPLE | IUPACNAME | Structure | Salt | MS |
|---|---|---|---|---|
| 12 | 3-(3-(4-tert-butylcyclohexyl)-5-((4-carbamimidamidobenzoyl)oxy)phenyl)-5-(carboxymethyl)-4,5-dihydro-1,2-oxazole-5-carboxylic acid (trans or cis form) | 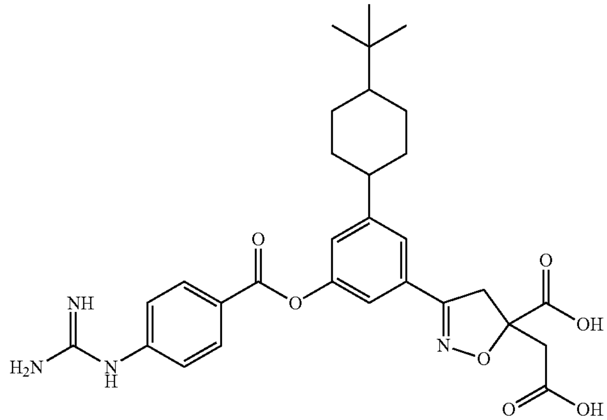 [SMILES: CC(C)(C)C1CCC(c2cc(OC(=O)c3ccc(NC(=N)N)cc3)cc(C3=NOC(CC(=O)O)(C(=O)O)C3)c2)CC1] | CF₃COOH | 565.1 |
| 13 | 3-(3-(4-tert-butylcyclohexyl)-5-((4-carbamimidamidobenzoyl)oxy)phenyl)-5-(carboxymethyl)-4,5-dihydro-1,2-oxazole-5-carboxylic acid (cis or trans form) | 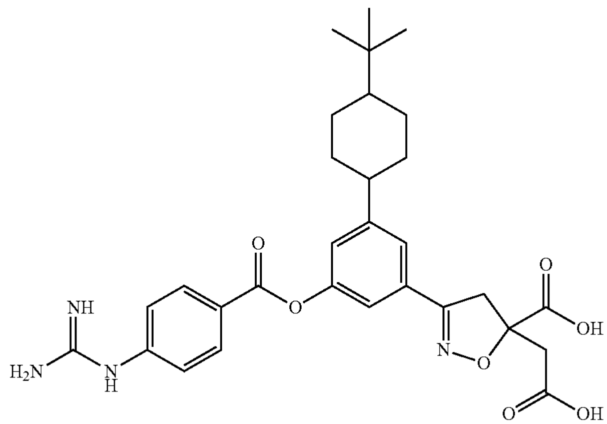 [SMILES: CC(C)(C)C1CCC(c2cc(OC(=O)c3ccc(NC(=N)N)cc3)cc(C3=NOC(CC(=O)O)(C(=O)O)C3)c2)CC1] | CF₃COOH | 565.1 |
| 14 | 3-(3-((4-carbamimidamidobenzoyl)oxy)-5-(2-carboxyethyl)phenyl)-5-(carboxymethyl)-4,5-dihydro-1,2-oxazole-5-carboxylic acid | 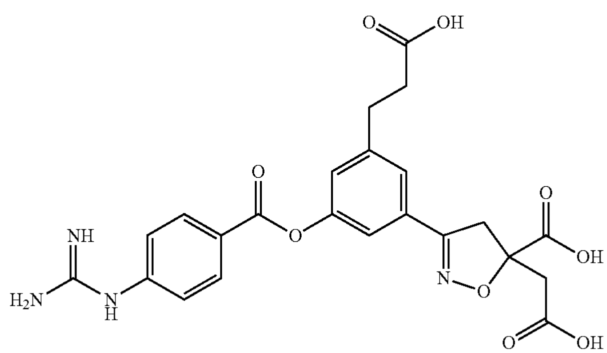 [SMILES: N=C(N)Nc1ccc(C(=O)Oc2cc(CCC(=O)O)cc(C3=NOC(CC(=O)O)(C(=O)O)C3)c2)cc1] | CF₃COOH | 499.0 |
| 15 | 3-(5-((4-carbamimidamidobenzoyl)oxy)-2-(2-carboxyethyl)phenyl)-5-(carboxymethyl)-4,5-dihydro-1,2-oxazole-5-carboxylic acid | 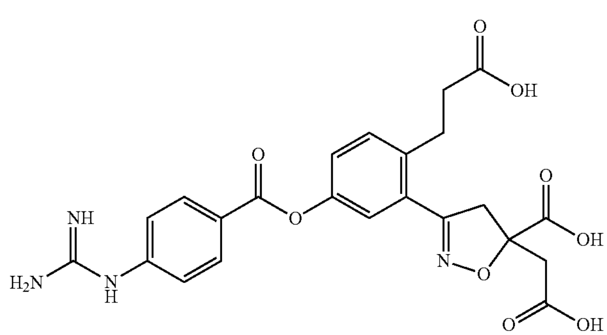 [SMILES: N=C(N)Nc1ccc(C(=O)Oc2ccc(CCC(=O)O)c(C3=NOC(CC(=O)O)(C(=O)O)C3)c2)cc1] | CF₃COOH | 499.0 |

TABLE 1-continued

| EXAMPLE | IUPACNAME | Structure | Salt | MS |
|---|---|---|---|---|
| 16 | 3-(3-((4-carbamimidamidobenzoyl)oxy)-2-methylphenyl)-5-(carboxymethyl)-4,5-dihydro-1,2-oxazole-5-carboxylic acid | 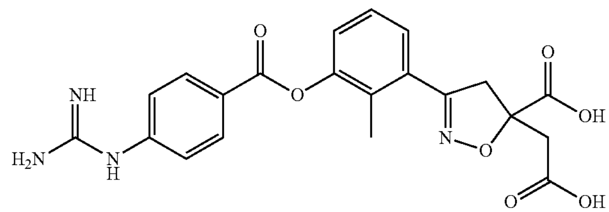 [SMILES: Cc1c(OC(=O)c2ccc(NC(=N)N)cc2)cccc1C1=NOC(CC(=O)O)(C(=O)O)C1] | CF₃COOH | 441.1 |
| 17 | 3-(3-((4-carbamimidamidobenzoyl)oxy)-4-methylphenyl)-5-(carboxymethyl)-4,5-dihydro-1,2-oxazole-5-carboxylic acid | 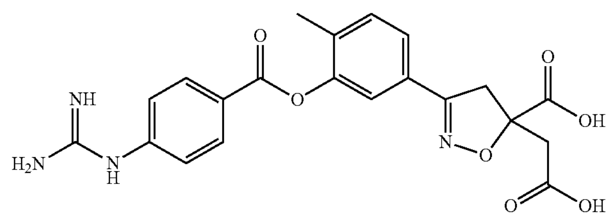 [SMILES: Cc1ccc(C2=NOC(CC(=O)O)(C(=O)O)C2)cc1OC(=O)c1ccc(NC(=N)N)cc1] | CF₃COOH | 441.1 |
| 18 | N-(3-(4-((4-carbamimidamidobenzoyl)oxy)-2-(5-carboxy-5-(carboxymethyl)-4,5-dihydro-1,2-oxazol-3-yl)phenyl)propanoyl)-L-aspartic acid | 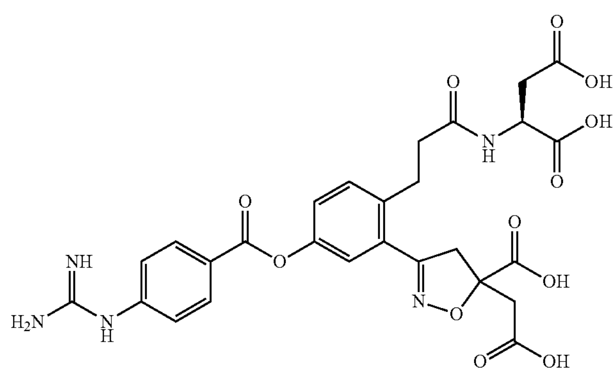 [SMILES: N=C(N)Nc1ccc(C(=O)Oc2ccc(CCC(=O)N[C@@H](CC(=O)O)C(=O)O)c(C3=NOC(CC(=O)O)(C(=O)O)C3)c2)cc1] | CF₃COOH | 614.2 |
| 19 | N-(3-(3-((4-carbamimidamidobenzoyl)oxy)-5-(5-carboxy-5-(carboxymethyl)-4,5-dihydro-1,2-oxazol-3-yl)phenyl)propanoyl)-L-aspartic acid | 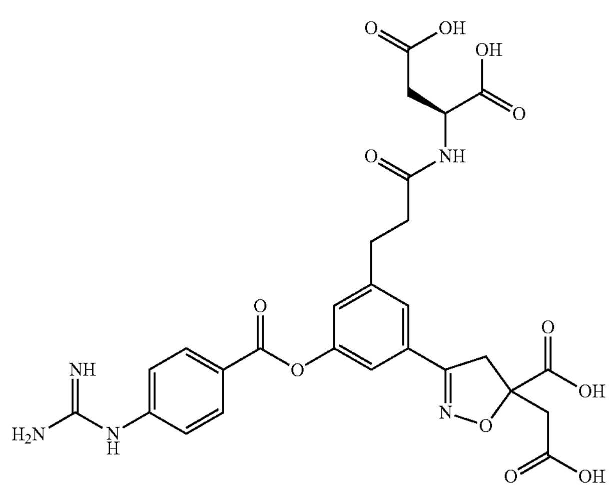 [SMILES: N=C(N)Nc1ccc(C(=O)Oc2cc(CCC(=O)N[C@@H](CC(=O)O)C(=O)O)cc(C3=NOC(CC(=O)O)(C(=O)O)C3)c2)cc1] | CF₃COOH | 614.1 |

TABLE 1-continued

| EXAMPLE | IUPACNAME | Structure | Salt | MS |
|---|---|---|---|---|
| 20 | N-(3-(2-(5,5-bis(carboxymethyl)-4,5-dihydro-1,2-oxazol-3-yl)-4-((4-carbamimidamidobenzoyl)oxy)phenyl)propanoyl)-L-aspartic acid | 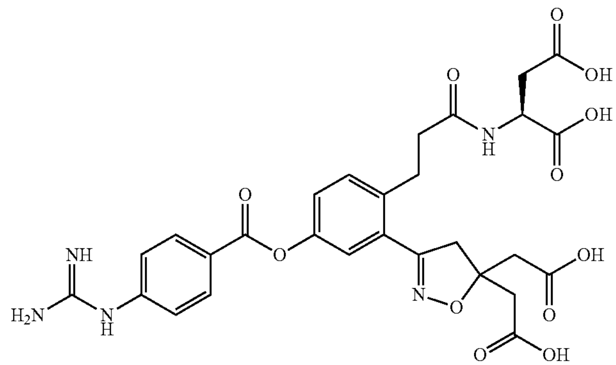 [SMILES: N=C(N)Nc1ccc(C(=O)Oc2ccc(CCC(=O)N[C@@H](CC(=O)O)C(=O)O)c(C3=NOC(CC(=O)O)(CC(=O)O)C3)c2)cc1] | CF₃COOH | 628.0 |
| 21 | N-(4-(4-(2-(5,5-bis(carboxymethyl)-4,5-dihydro-1,2-oxazol-3-yl)-4-((4-carbamimidamidobenzoyl)oxy)phenyl)piperidin-1-yl)-4-oxobutanoyl)-L-aspartic acid | 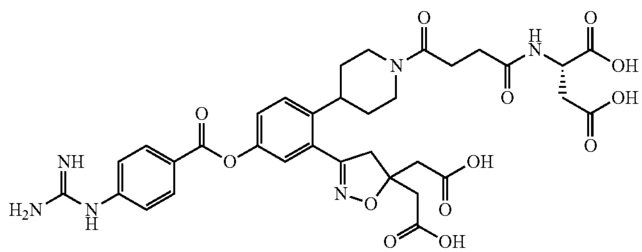 [SMILES: N=C(N)Nc1ccc(C(=O)Oc2ccc(C3CCN(C(=O)CCC(=O)N[C@@H](CC(=O)O)C(=O)O)CC3)c(C3=NOC(CC(=O)O)(CC(=O)O)C3)c2)cc1] | CF₃COOH | 739.2 |
| 22 | 3-(4-(2-(5,5-bis(carboxymethyl)-4,5-dihydro-1,2-oxazol-3-yl)-4-((4-carbamimidamidobenzoyl)oxy)phenyl)piperidin-1-yl)propanoic acid | 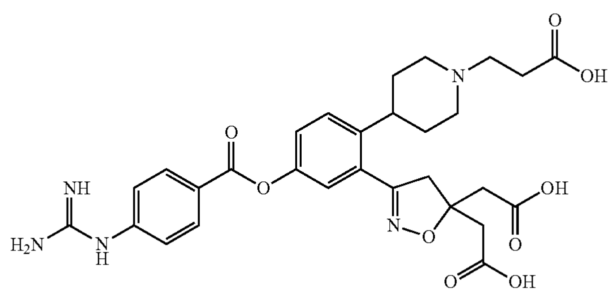 [SMILES: N=C(N)Nc1ccc(C(=O)Oc2ccc(C3CCN(CCC(=O)O)CC3)c(C3=NOC(CC(=O)O)(CC(=O)O)C3)c2)cc1] | 2CF₃COOH | 596.2 |
| 23 | N-(3-(3-(5,5-bis(carboxymethyl)-4,5-dihydro-1,2-oxazol-3-yl)-5-((4-carbamimidamidobenzoyl)oxy)phenyl)propanoyl)-L-aspartic acid | 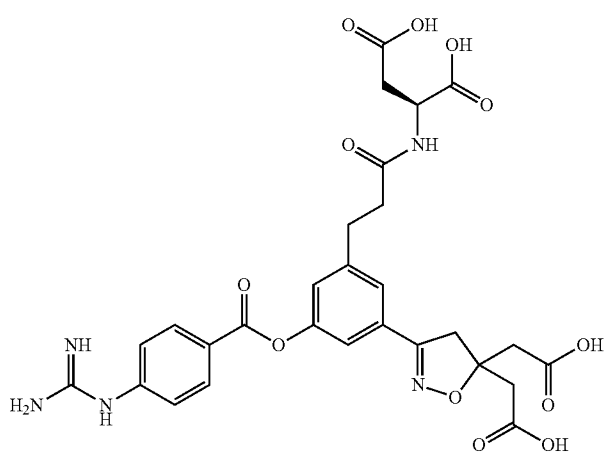 [SMILES: N=C(N)Nc1ccc(C(=O)Oc2cc(CCC(=O)N[C@@H](CC(=O)O)C(=O)O)cc(C3=NOC(CC(=O)O)(CC(=O)O)C3)c2)cc1] | CF₃COOH | 628.0 |

TABLE 1-continued

| EXAMPLE | IUPACNAME | Structure | Salt | MS |
|---|---|---|---|---|
| 24 | 3-(2-(5,5-bis(carboxymethyl)-4,5-dihydro-1,2-oxazol-3-yl)-4-((4-carbamimidamidobenzoyl)oxy)phenyl)propanoic acid | 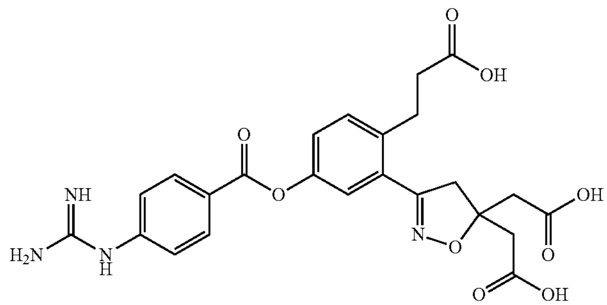 [SMILES: N=C(N)Nc1ccc(C(=O)Oc2ccc(CCC(=O)O)c(C3=NOC(CC(=O)O)(CC(=O)O)C3)c2)cc1] | | 513.1 |
| 25 | 2,2'-(3-(5-((4-carbamimidamidobenzoyl)oxy)-2-(3-(1,1-dioxidothiomorpholin-4-yl)-3-oxopropyl)phenyl)-4,5-dihydro-1,2-oxazole-5,5-diyl)diacetic acid | 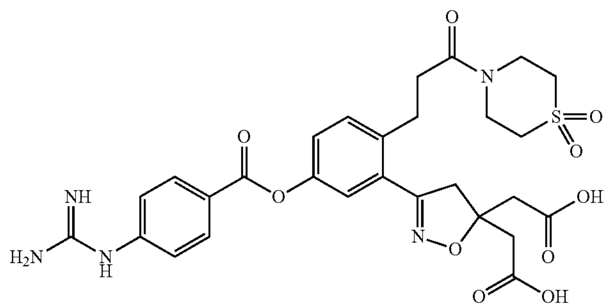 [SMILES: N=C(N)Nc1ccc(C(=O)Oc2ccc(CCC(=O)N3CCS(=O)(=O)CC3)c(C3=NOC(CC(=O)O)(CC(=O)O)C3)c2)cc1] | | 630.2 |
| 26 | 2,2'-(3-(5-((4-carbamimidamidobenzoyl)oxy)-2-(3-(morpholin-4-yl)-3-oxopropyl)phenyl)-4,5-dihydro-1,2-oxazole-5,5-diyl)diacetic acid | 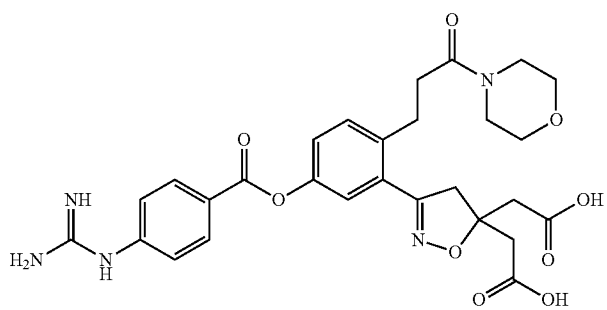 [SMILES: N=C(N)Nc1ccc(C(=O)Oc2ccc(CCC(=O)N3CCOCC3)c(C3=NOC(CC(=O)O)(CC(=O)O)C3)c2)cc1] | | 582.2 |
| 27 | 2,2'-(3-(5-((4-carbamimidamidobenzoyl)oxy)-2-(3-((2-(methylsulfonyl)ethyl)amino)-3-oxopropyl)phenyl)-4,5-dihydro-1,2-oxazole-5,5-diyl)diacetic acid | 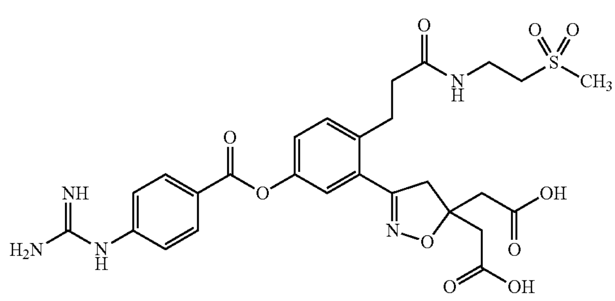 [SMILES: CS(=O)(=O)CCNC(=O)CCc1ccc(OC(=O)c2ccc(NC(=N)N)cc2)cc1C1=NOC(CC(=O)O)(CC(=O)O)C1] | CF$_3$COOH | 616.2 |

TABLE 1-continued

| EXAMPLE | IUPAC NAME | Structure | Salt | MS |
|---|---|---|---|---|
| 28 | N²-(3-(2-(5,5-bis(carboxymethyl)-4,5-dihydro-1,2-oxazol-3-yl)-4-((4-carbamimidamidobenzoyl)oxy)phenyl)propanoyl)-L-asparagine | 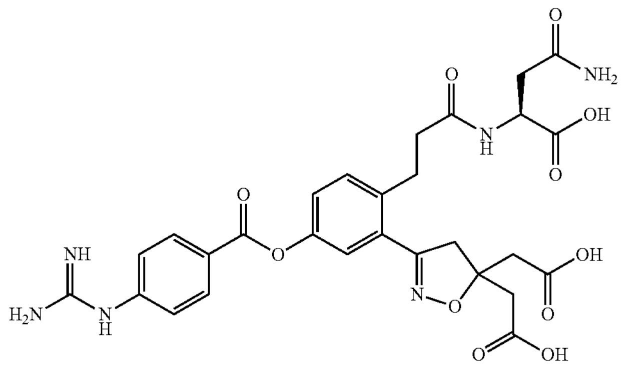 [SMILES: N=C(N)Nc1ccc(C(=O)Oc2ccc(CCC(=O)N[C@@H](CC(N)=O)C(=O)O)c(C3=NOC(CC(=O)O)(CC(=O)O)C3)c2)cc1] | CF₃COOH | 627.2 |
| 29 | N²-(3-(2-(5,5-bis(carboxymethyl)-4,5-dihydro-1,2-oxazol-3-yl)-4-((4-carbamimidamidobenzoyl)oxy)phenyl)propanoyl)-L-glutamine | 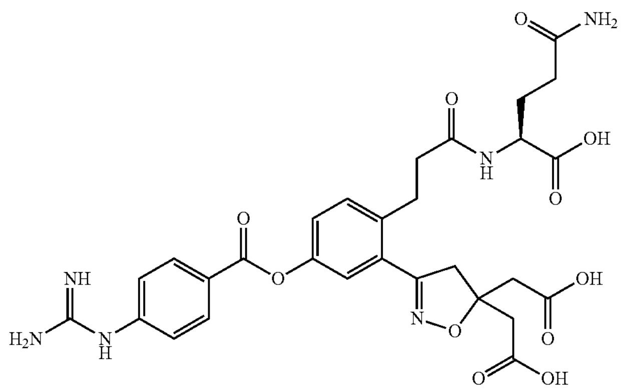 [SMILES: N=C(N)Nc1ccc(C(=O)Oc2ccc(CCC(=O)N[C@@H](CCC(N)=O)C(=O)O)c(C3=NOC(CC(=O)O)(CC(=O)O)C3)c2)cc1] | CF₃COOH | 641.2 |
| 30 | N-(3-(2-(5,5-bis(carboxymethyl)-4,5-dihydro-1,2-oxazol-3-yl)-4-((4-carbamimidamidobenzoyl)oxy)phenyl)propanoyl)glycine | 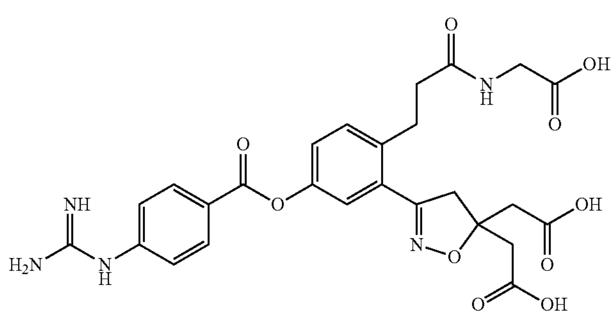 [SMILES: N=C(N)Nc1ccc(C(=O)Oc2ccc(CCC(=O)NCC(=O)O)c(C3=NOC(CC(=O)O)(CC(=O)O)C3)c2)cc1] | | 568.1 |
| 31 | N-(3-(2-(5,5-bis(carboxymethyl)-4,5-dihydro-1,2-oxazol-3-yl)-4-((4-carbamimidamidobenzoyl)oxy)phenyl)propanoyl)-N-methylglycine | 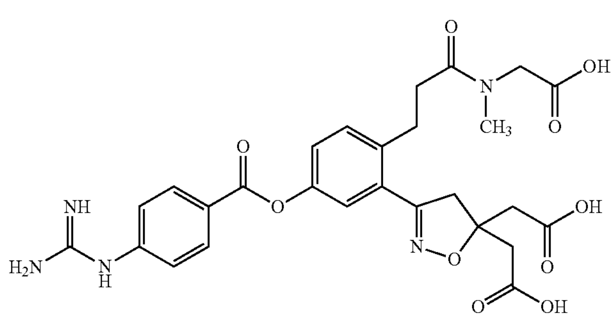 [SMILES: CN(CC(=O)O)C(=O)CCc1ccc(OC(=O)c2ccc(NC(=N)N)cc2)cc1C1=NOC(CC(=O)O)(CC(=O)O)C1] | CF₃COOH | 584.2 |

TABLE 1-continued

| EXAMPLE | IUPACNAME | Structure | Salt | MS |
|---|---|---|---|---|
| 32 | N-(3-(2-(5,5-bis(carboxymethyl)-4,5-dihydro-1,2-oxazol-3-yl)-4-((4-carbamimidamidobenzoyl)oxy)phenyl)propanoyl)-beta-alanine | 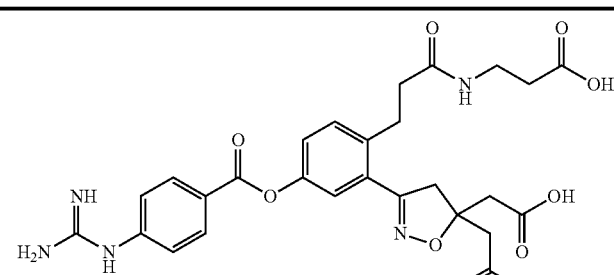 | | 584.2 |
| 33 | 1-(3-(2-(5,5-bis(carboxymethyl)-4,5-dihydro-1,2-oxazol-3-yl)-4-((4-carbamimidamidobenzoyl)oxy)phenyl)propanoyl)piperidine-4-carboxylic acid | 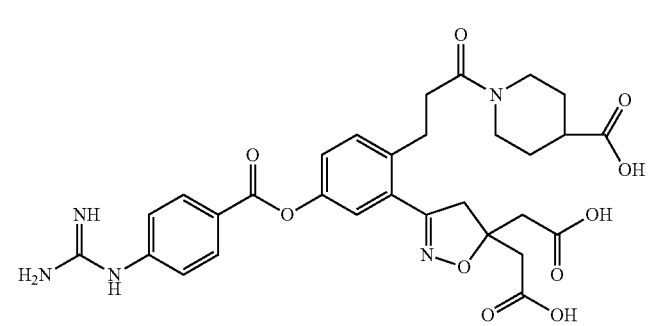 [SMILES: N=C(N)Nc1ccc(C(=O)Oc2ccc(CCC(=O)N3CCC(C(=O)O)CC3)c(C3=NOC(CC(=O)O)(CC(=O)O)C3)c2)cc1] | | 624.2 |
| 34 | 2,2'-(3-(5-((4-carbamimidamidobenzoyl)oxy)-2-(3-oxo-3-((2-sulfoethyl)amino)propyl)phenyl)-4,5-dihydro-1,2-oxazole-5,5-diyl)diacetic acid | 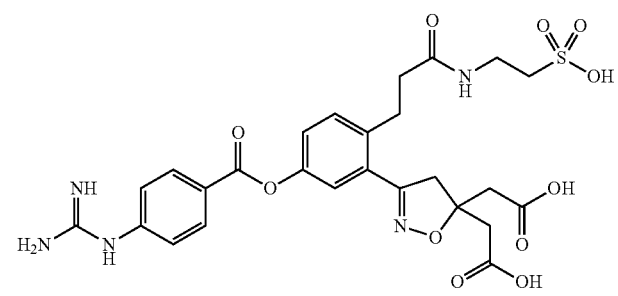 [SMILES: N=C(N)Nc1ccc(C(=O)Oc2ccc(CCC(=O)NCCS(=O)(=O)O)c(C3=NOC(CC(=O)O)(CC(=O)O)C3)c2)cc1] | | 620.1 |

Test Example 1

Human Enteropeptidase Inhibitory Activity

Human recombinant enteropeptidase (#REN-260, ITSI-Biosciences, LLC) was diluted with an assay buffer (50 mM Tricine (pH 8.0), 0.01 (w/v) % Tween 20, 10 mM $CaCl_2$) to prepare a 24 mU/mL enzyme solution. Subsequently, 5FAM-Abu-Gly-Asp-Asp-Asp-Lys-Ile-Val-Gly-Gly-Lys (CPQ2)-Lys-Lys-NH2 (purity: 97.2%, CPC Scientific, Inc.) produced according to a synthesis method known per se was diluted with an assay buffer to prepare a 2.1 uM ("u" represents "micro") substrate solution. Each test compound was dissolved in DMSO to prepare a 1 mM solution, which was then diluted 100-fold with an assay buffer to prepare a compound solution. The compound solution (5 uL/well) and the substrate solution (5 uL/well) were added to a 384-well black plate (#784076, Greiner Bio-One) and mixed. Then, the enzyme solution (5 uL/well) was added to the plate and mixed to start reaction. The fluorescence intensity was measured at an excitation wavelength of 485 nm and a fluorescence wavelength of 535 nm using a fluorescence plate reader EnVision (PerkinElmer Inc.). Also, the same reaction as above was performed except that the test compound was not added (test compound non-supplemented group). In addition, the same reaction as above was performed except that neither the test compound nor the enzyme was added (control group). The inhibition rate was calculated from the fluorescence intensity 2 hours after the start of the reaction according to the following equation:

Inhibition rate (%)=(1−(Fluorescence intensity of the test compound supplemented group−Fluorescence intensity of the control group)/(Fluorescence intensity of the test compound non-supplemented group−Fluorescence intensity of the control group))×100

The results are shown in Table 2.

TABLE 2

| Test compound (Example No.) | Inhibition rate at 3.3 uM (%) |
|---|---|
| 1 | 101 |
| 2 | 101 |
| 3 | 101 |
| 4 | 101 |
| 5 | 101 |
| 6 | 100 |
| 7 | 101 |
| 8 | 101 |
| 9 | 101 |
| 10 | 101 |
| 11 | 100 |
| 12 | 101 |
| 13 | 100 |

TABLE 2-continued

| Test compound (Example No.) | Inhibition rate at 3.3 uM (%) |
|---|---|
| 14 | 100 |
| 15 | 101 |
| 16 | 100 |
| 17 | 87 |
| 18 | 100 |
| 19 | 101 |
| 20 | 100 |
| 21 | 100 |
| 22 | 101 |
| 23 | 100 |
| 24 | 100 |
| 25 | 100 |
| 26 | 100 |
| 27 | 100 |
| 28 | 100 |
| 29 | 100 |
| 30 | 100 |
| 31 | 100 |
| 32 | 100 |
| 33 | 100 |
| 34 | 101 |

As mentioned above, the compound of the present invention has a superior enteropeptidase inhibitory action.

Test Example 2

Test on Elevation of Protein Concentration in Feces Using HFD-Fed Mouse

A 0.5% methylcellulose suspension (test compound administered group, 5 mice per group) containing each test compound (10 mg/kg) or a 0.5% methylcellulose suspension (test compound non-administered group (vehicle), 5 mice per group) was orally administered to each high fat diet-fed (HFD-fed) mouse (D12079B diet, male, 15 weeks old), and the whole feces were recovered at day 1 of administration. The dry feces were dissolved in a 0.5 N aqueous sodium hydroxide solution. After centrifugation at 12,000 rpm, a protein concentration was quantified (Lowry method) using the supernatant to calculate a protein concentration (mg/g feces) in 1 g of feces. The mean and standard deviation of each group are shown below.

TABLE 3

| Test compound | Dosage of compound (mg/kg) | Protein concentration in feces (mg/g) |
|---|---|---|
| vehicle | 0 | 75.2 ± 8.9 |
| Example 1 | 10 | 151.5 ± 22.8 |
| Example 5 | 10 | 144.5 ± 26.6 |

As mentioned above, the compound of the present invention has an action of elevating a protein concentration in feces by an enteropeptidase inhibitory action.

Test Example 3

Test on Antiobesity Action Using DIO Mouse

A 0.5% methylcellulose suspension (test compound administered group, 5 or 6 mice per group) containing each test compound (20 or 60 mg/kg) or a 0.5% methylcellulose suspension (test compound non-administered group (vehicle), 6 mice per group) was orally administered to each diet-induced obesity (DIO) mouse (D12079B diet, male, 46 weeks old) once a day for 4 weeks. The means of body weights and standard deviations at the start of administration and after 4-week continuous administration are shown below.

The results are shown in the table.

TABLE 4

| | Dosage of compound (mg/kg) | Body weight (g) | |
|---|---|---|---|
| Test compound | | At start of administration | After 4-week continuous administration |
| vehicle | 0 | 48.9 ± 2.8 | 48.0 ± 2.2 |
| Example 1 | 20 | 48.9 ± 2.0 | 43.1 ± 3.5 |
| Example 1 | 60 | 48.9 ± 2.5 | 40.2 ± 2.1 |

As mentioned above, the compound of the present invention exhibits a dose-dependent body weight lowering action and has an antiobesity action based on an enteropeptidase inhibitory action.

Formulation Example 1

Production of Capsule

| 1) Compound of Example 1 | 30 mg |
|---|---|
| 2) Fine cellulose powder | 10 mg |
| 3) Lactose | 19 mg |
| 4) Magnesium stearate | 1 mg |
| Total: | 60 mg |

Ingredients 1), 2), 3), and 4) are mixed and filled in a gelatin capsule shell.

Formulation Example 2

Production of Tablet

| 1) Compound of Example 1 | 30 g |
|---|---|
| 2) Lactose | 50 g |
| 3) Corn starch | 15 g |
| 4) Carboxymethylcellulose calcium | 44 g |
| 5) Magnesium stearate | 1 g |
| Total of 1000 tablets: | 140 g |

The whole amounts of ingredients 1), 2), and 3) and 30 g of ingredient 4) are kneaded with water and granulated after vacuum drying. The granulated powders are mixed with 14 g of ingredient 4) and 1 g of ingredient 5). The mixture is compressed using a tableting machine. In this way, 1000 tablets each containing 30 mg of the compound of Example 1 are obtained.

INDUSTRIAL APPLICABILITY

The compound of the present invention has superior enteropeptidase inhibitory action and is useful in the treatment or prophylaxis of obesity, diabetes mellitus, and the like.

All the publications, patents, and the patent applications cited herein are incorporated herein by reference in their entireties.

[Sequence Listing]

The invention claimed is:

1. A compound which is (5R)-3-(3-((4-Carbamimidamidobenzoyl)oxy)phenyl)-5-(carboxymethyl)-4, 5-dihydro-1, 2-oxazole-5-carboxylic acid or a salt thereof.

2. A compound which is (5S)-3-(3-((4-Carbamimidamidobenzoyl)oxy)phenyl)-5-(carboxymethyl)-4, 5-dihydro-1, 2-oxazole-5-carboxylic acid or a salt thereof.

3. A compound which is 2,2'-(3-(3-((4-Carbamimidamidobenzoyl)oxy)phenyl)-4,5-dihydro-1,2-oxazole-5,5-diyl) diacetic acid or a salt thereof.

* * * * *

```
                            SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa stands for Abu (2-Aminobutyric acid)
<220> FEATURE:
<221> NAME/KEY: MOD_RES
<222> LOCATION: (1)..(1)
<223> OTHER INFORMATION: modified with 5FAM
<220> FEATURE:
<221> NAME/KEY: MOD_RES
<222> LOCATION: (11)..(11)
<223> OTHER INFORMATION: modified with CPQ2

<400> SEQUENCE: 1

Xaa Gly Asp Asp Asp Lys Ile Val Gly Gly Lys Lys Lys
1               5                   10
```